US007504222B2

(12) United States Patent
Ayers et al.

(10) Patent No.: US 7,504,222 B2
(45) Date of Patent: Mar. 17, 2009

(54) COMPOSITIONS, KITS, AND METHODS FOR IDENTIFICATION, ASSESSMENT, PREVENTION, AND THERAPY OF BREAST CANCER

(75) Inventors: Mark D. Ayers, Pennington, NJ (US); Jim Stec, Plymouth, MA (US); Andrew Damokosh, West Hartford, CT (US); Edwin Clark, Pennington, NJ (US); Kenneth R. Hess, Houston, TX (US); Gabriel N. Hortobagyi, Bellaire, TX (US); Lajos Pusztai, Houston, TX (US); W. Fraser Symmans, Houston, TX (US); Robert C. Bast, Jr., Houston, TX (US)

(73) Assignees: Millennium Pharmaceuticals, Inc., Cambridge, MA (US); Board of Regents, The University of Texas, Austin, TX (US)

( * ) Notice: Subject to any disclaimer, the term of this patent is extended or adjusted under 35 U.S.C. 154(b) by 773 days.

(21) Appl. No.: 10/285,393

(22) Filed: Oct. 31, 2002

(65) Prior Publication Data
US 2003/0219767 A1 Nov. 27, 2003

Related U.S. Application Data

(60) Provisional application No. 60/335,981, filed on Nov. 2, 2001, provisional application No. 60/334,994, filed on Oct. 31, 2001.

(51) Int. Cl.
*G01N 33/53* (2006.01)
(52) U.S. Cl. .................. 435/7.1; 435/7.23
(58) Field of Classification Search .............. None
See application file for complete search history.

(56) References Cited

U.S. PATENT DOCUMENTS

| 5,976,837 | A | 11/1999 | Jacobs et al. |
| 6,033,869 | A | 3/2000 | Goli et al. |
| 6,682,888 | B1 | 1/2004 | Loring et al. |
| 6,974,667 | B2 | 12/2005 | Horne et al. |
| 2002/0039764 | A1 | 4/2002 | Rosen et al. |
| 2002/0142981 | A1 | 10/2002 | Home et al. |
| 2003/0054421 | A1 | 3/2003 | Rosen et al. |
| 2003/0134280 | A1 | 7/2003 | Munger et al. |
| 2003/0134324 | A1 | 7/2003 | Munger et al. |
| 2004/0101874 | A1 | 5/2004 | Ghosh et al. |
| 2004/0115625 | A1 | 6/2004 | Ebner |
| 2005/0019858 | A1 | 1/2005 | Goli et al. |
| 2005/0033018 | A1 | 2/2005 | Lal et al. |
| 2005/0064454 | A1 | 3/2005 | Young et al. |
| 2005/0074842 | A1 | 4/2005 | Kato et al. |
| 2005/0130171 | A1 | 6/2005 | Loring et al. |

FOREIGN PATENT DOCUMENTS

| DE | 19627237 | A1 | 1/1998 |
| EP | 1035204 | A1 | 9/2000 |
| JP | 2001-501300 | | 1/2001 |
| JP | 2001-517944 | | 10/2001 |
| JP | 2001-527392 | | 12/2001 |
| JP | 2002-512524 | | 4/2002 |
| JP | 2003-512815 | | 4/2003 |
| JP | 2004-507206 | | 3/2004 |
| WO | WO-98/10291 | A1 | 3/1998 |
| WO | WO-98/40486 | A2 | 9/1998 |
| WO | WO-98/41538 | A2 | 9/1998 |
| WO | WO-98/55508 | A2 | 12/1998 |
| WO | WO-99/24568 | A1 | 5/1999 |
| WO | WO-00/55173 | A1 | 9/2000 |
| WO | WO-01/32927 | A2 | 5/2001 |
| WO | WO-01/88088 | A2 | 11/2001 |
| WO | WO-01/94629 | A2 | 12/2001 |
| WO | WO-02/12440 | A2 | 2/2002 |
| WO | WO-02/29103 | A2 | 4/2002 |
| WO | WO-02/068579 | A2 | 9/2002 |
| WO | WO-02/078524 | A2 | 10/2002 |
| WO | WO-03/016475 | A2 | 2/2003 |

OTHER PUBLICATIONS

Greenbaum et al., Genome Biology, vol. 4, Issue 9, pp. 117.1-117.8, 2003.*
Crudden, Gerard et al., "Overexpression of the Cytochrome P450 Activator Hpr6 (Heme-1 Domain Protein/Human Progesterone Receptor) in Tumors," *TumorBiology*, vol. 26:142-146 (2005).
Crudden, Gerard et al., "Hpr6 (Heme-1 Domain Protein) Regulates the Susceptibility of Cancer Cells to Chemotherapeutic Drugs," *The Journal of Pharmacology and Therapeutics*, vol. 316(1):448-455 (2006).
GenBank Accession No. AA166645 [Hillier L. et al., "WashU-NCI human EST Project"] Mar. 12, 1998.
GenBank Accession No. CN356045, [Brandenberger, R. et al., "Transcriptome characterization elucidates signaling networks that control human ES cell growth and differentiation," *Nat. Biotechnol.*, vol. 22(6):707-716 (2004)] May 16, 2004.
GenBank Accession No. NM_006667, [Crudden, G. et al., "Hpr6 (heme-1 domain protein) regulates the susceptibility of cancer cells to chemotherapeutic drugs," *J. Pharmacol. Exp. Ther.*, vol. 316(1):448-455 (2006)] Nov. 17, 2006.
GenBank Accession No. R59281, [Hillier, L. et al., "The WashU-Merck EST Project,"] May 24, 1995.
Mallory, Julia C. et al., "A Novel Group of Genes Regulates Susceptibility to Antineoplastic Drugs in Highly Tumorigenic Breast Cancer Cells," *Molecular Pharmacology*, vol. 68(6):1747-1756 (2005).

* cited by examiner

*Primary Examiner*—Misook Yu
*Assistant Examiner*—Mark Halvorson
(74) *Attorney, Agent, or Firm*—Lahive & Cockfield, LLP; Maria Laccotripe Zacharakis

(57) ABSTRACT

The invention relates to compositions, kits, and methods for detecting, characterizing, preventing, and treating human breast cancers. A variety of newly identified markers are provided, wherein changes in the levels of expression of one or more of the markers is correlated with the presence of breast cancer.

15 Claims, No Drawings

SEQUENCE LISTING

```
<160> NUMBER OF SEQ ID NOS: 2

<210> SEQ ID NO 1
<211> LENGTH: 1890
<212> TYPE: DNA
<213> ORGANISM: Homo sapiens

<400> SEQUENCE: 1
gacccacgcg tccggggagg agaaagtggc gagttccgga tccctgccta gcgcggccca      60
acctttactc cagagatcat ggctgccgag gatgtggtgg cgactggcgc cgacccaagc     120
gatctggaga gcggcgggct gctgcatgag attttcacgt cgccgctcaa cctgctgctg     180
cttggcctct gcatcttcct gctctacaag atcgtgcgcg gggaccagcc ggcggccagc     240
ggcgacagcg acgacgacga gccgcccct ctgccccgcc tcaagcggcg cgacttcacc     300
cccgccgagc tgcggcgctt cgacggcgtc caggaccgc gcatactcat ggccatcaac     360
ggcaaggtgt tcgatgtgac caaaggccgc aaattctacg ggcccgaggg gccgtatggg     420
gtctttgctg gaagagatgc atccaggggc cttgccacat tttgcctgga taaggaagca     480
ctgaaggatg agtacgatga cctttctgac ctcactgctg cccagcagga gactctgagt     540
gactgggagt ctcagttcac tttcaagtat catcacgtgg gcaaactgct gaaggagggg     600
gaggagccca ctgtgtactc agatgaggaa gaaccaaaag atgagagtgc ccggaaaaat     660
gattaaagca ttcagtggaa gtatatctat ttttgtattt tgcaaaatca tttgtaacag     720
tccactctgt ctttaaaaca tagtgattac aatatttaga aagttttgag cacttgctat     780
```

-continued

```
aagtttttta attaacatca ctagtgacac taataaaatt aacttcttag aatgcatgat   840
gtgtttgtgt gtcacaaatc cagaaagtga actgcagtgc tgtaatacac atgttaatac   900
tgtttttctt ctatctgtag ttagtacagg atgaatttaa atgtgttttt cctgagagac   960
aaggaagact tgggtatttc ccaaaacagg taaaaatctt aaatgtgcac caagagcaaa  1020
ggatcaactt ttagtcatga tgttctgtaa agacaacaaa tcccttttt tttctcaatt   1080
gacttaactg catgatttct gttttatcta cctctaaagc aaatctgcag tgttccaaag  1140
actttggtat ggattaagcg ctgtccagta acaaaatgaa atctcaaaac agagctcagc  1200
tgcaaaaaag catattttct gtgtttctgg actgcactgt tgtccttgcc ctcacataga  1260
cactcagaca ccctcacaaa cacagtagtc tatagttagg attaaaatag gatctgaaca  1320
ttcaaaagaa agctttggaa aaaaagagct ggctggccta aaaacctaaa tatatgatga  1380
agattgtagg actgtcttcc caagccccat gttcatggtg gggcaatggt tatttggtta  1440
ttttactcaa ttggttactc tcatttgaaa tgagggaggg acatacagaa taggaacagg  1500
tgtttgctct cctaagagcc ttcatgcaca cccctgaacc acgaggaaac agtacagtcg  1560
ctagtcaagt ggttttttaaa gtaaagtata ttcataaggt aacagttatt ctgttgttat  1620
aaaactatac ccactgcaaa agtagtagtc aagtgtctag gtctttgata ttgctctttt  1680
ggttaacact aagcttaagt agactataca gttgtatgaa tttgtaaaag tatatgaaca  1740
cctagtgaga tttcaaactt gtaattgtgg ttaaatagtc attgtatttt cttgtgaact  1800
gtgtttatg attttacctc aaatcagaaa acaaaatgat gtgctttggt cagttaataa   1860
aaatggtttt acccactaaa aaaaaaaaaa                                    1890
```

<210> SEQ ID NO 2
<211> LENGTH: 195
<212> TYPE: PRT
<213> ORGANISM: Homo sapiens

<400> SEQUENCE: 2

```
Met Ala Ala Glu Asp Val Val Ala Thr Gly Ala Asp Pro Ser Asp Leu
 1               5                  10                  15

Glu Ser Gly Gly Leu Leu His Glu Ile Phe Thr Ser Pro Leu Asn Leu
             20                  25                  30

Leu Leu Leu Gly Leu Cys Ile Phe Leu Leu Tyr Lys Ile Val Arg Gly
         35                  40                  45

Asp Gln Pro Ala Ala Ser Gly Asp Ser Asp Asp Glu Pro Pro Pro
     50                  55                  60

Leu Pro Arg Leu Lys Arg Arg Asp Phe Thr Pro Ala Glu Leu Arg Arg
 65                  70                  75                  80

Phe Asp Gly Val Gln Asp Pro Arg Ile Leu Met Ala Ile Asn Gly Lys
                 85                  90                  95

Val Phe Asp Val Thr Lys Gly Arg Lys Phe Tyr Gly Pro Glu Gly Pro
            100                 105                 110

Tyr Gly Val Phe Ala Gly Arg Asp Ala Ser Arg Gly Leu Ala Thr Phe
        115                 120                 125

Cys Leu Asp Lys Glu Ala Leu Lys Asp Glu Tyr Asp Asp Leu Ser Asp
    130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175
```

```
-continued
Pro Thr Val Tyr Ser Asp Glu Glu Pro Lys Asp Glu Ser Ala Arg
            180                 185                 190
Lys Asn Asp
        195
```

COMPOSITIONS, KITS, AND METHODS FOR IDENTIFICATION, ASSESSMENT, PREVENTION, AND THERAPY OF BREAST CANCER

PRIORITY INFORMATION

The present application claims priority from U.S. provisional patent application Ser. No. 60/334,994, filed on Oct. 31, 2001, and from U.S. provisional patent application Ser. No. 60/335,981, filed on Nov. 2, 2001. All of the above applications are expressly incorporated by reference.

FIELD OF THE INVENTION

The field of the invention is breast cancer, including diagnosis, characterization, management, and therapy of breast cancer.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al, 1997, *CA Cancer J. Clin.* 47:5-27; Chu et al, 1996, *J. Nat. Cancer Inst.* 88:1571-1579). While the pathogenesis of breast cancer is unclear, transformation of normal breast epithelium to a malignant phenotype may be the result of genetic factors, especially in women under 30 (Miki et al., 1994, *Science*, 266:66-71). The discovery and characterization of BRCA1 and BRCA2 has recently expanded our knowledge of genetic factors that can contribute to familial breast cancer. Germline mutations within these two loci are associated with a 50 to 85% lifetime risk of breast and/or ovarian cancer (Casey, 1997, *Curr. Opin. Oncol.* 9:88-93; Marcus et al., 1996, *Cancer* 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, *Am. J. Surg.* 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

Human breast tumors are diverse in their natural history and in the responsiveness to treatments. Variation in transcriptional programs accounts for much of the biological diversity of human cells and tumors. In each cell, signal transduction and regulatory systems transduce information from the cell's identity to its environmental status, thereby controlling the level of expression of every gene in the genome. (Perou, C. et al., (2000) *Nature* 406:747-752).

Human breast tumors are histologically complex tissues, containing a variety of cell types in addition to the carcinoma cells. Two distinct types of epithelial cell are found in the human mammary gland: basal (and/or myoepithelial) cells and luminal epithelial cells. These two cell types are conveniently distinguished immunohistochemically; basal epithelial cells can be stained with antibodies to keratin 5/6, whereas luminal epithelial cells stain with antibodies against keratins 8/18. (Perou et al., supra)

Gene expression information generated by DNA microarray analysis of human tumors can provide molecular phenotyping that can identify distinct tumor classifications not evident by traditional histopathological methods. (West, M. et al., (2001) *PNAS* 2001 98: 11462-11467). The analysis of gene expression represents an indirect measure of the genetic alterations in tumors because, in most instances, these alterations affect gene regulatory pathways. Given the tremendous complexity that can be scored by measuring gene expression with DNA microarrays, together with the absence of bias in assumptions as to what type of pathway might be affected in a particular tumor, the analysis of gene expression profiles offers the potential to impact clinical decision-making based on more precise determinations of tumor cell phenotypes. (West et al., supra).

Currently, about 100 critical genes in growth stimulatory pathways have been identified as potential targets for development as therapeutic agents. Human epidermal growth factor receptor-2 ("HER2") is a member of a class of molecules in this pathway, called growth factor receptors. Following discovery of the HER2 probe in 1987, it was determined that 25% to 30% of women with breast cancer have amplification of this gene. Although expression does not always follow gene amplification, HER2 expression was found to directly correlate to its degree of amplification, such that amplification results in overexpression in 95% of cases. When HER2 overexpression occurs, at some point between premalignant and preinvasive disease, it affects both the biologic life of the tumor and the prognosis of the patient. The HER2 alteration does not appear to change over time. When it is amplified in the primary tumor, the degree of amplification seems to hold steady throughout the course of disease and is similarly amplified in subsequent metastases.

Moreover, the presence of multiple copies of the HER-2 gene, and the corresponding over-expression of its protein, plays a pivotal role in the rapid growth of tumor cells in 25-30 percent of breast cancer patients. HER2, thus, has a profound significance on breast cancer characterization and management. In a state of overexpression, its impact extends from its tumorigenicity, metastatic potential, effects on hormone dependence, and effects on response to tamoxifen and chemotherapy. Determination of HER-2 status is therefore a critical tool for selecting appropriate therapeutic options. The detection of amplification of the HER2 gene, as a measure of patient disease status and survivability, is further described in U.S. Pat. No. 4,968,603, incorporated herein by reference. In addition, a HER2 inhibitor, "Herceptin" has been developed by Genentech (South San Francisco, Calif.).

Other molecular differences in breast tissue have also been found to be significant in the diagnosis, characterization, management, and therapy of breast cancer. For example, the large scale molecular differences between estrogen receptor ("ER") negative and ER positive tumors are particularly interesting in the light of clinical observations which indicate that the natural history and biological behavior of ER positive and ER negative tumors are distinct even in the absence of hormonal therapy. For example, ER negative cancers tend to recur sooner and show a different rate of recurrence in distant organ sites compared to ER positive tumors. The clinical observations and the molecular profiling data emerging from several laboratories, now strongly suggest that ER negative and ER positive breast cancers are two distinct disease entities rather than phenotypic variations of the same disease. (Pusztai, L. et al., in publication).

If the clinically significant determination is the status of the ER pathways, not just the status of the ER itself, then measurements of gene expression profiles that reflect activity of the pathway could also provide an important advance in understanding the behavior of breast cancers. Genes that encode proteins that synergize with ER, such as HNF3 antibody and androgen receptor, may also provide significant information regarding breast cancers.

SUMMARY OF THE INVENTION

The invention relates to markers associated with breast cancer as well as methods of assessing whether a patient is afflicted with breast cancer and methods of characterizing and treating breast cancer. The markers of the present invention are identified in Table 1 as n1-n736, and are over-expressed in breast cancer cells compared to normal (i.e. non cancerous) cells. The markers of Table 1 have further been identified in Tables 2 (n1-n302) and Tables 3 (n303-n736) as estrogen receptor ("ER") positive markers and ER negative markers, respectfully. In particular, the markers of Table 2 are over-expressed in ER positive breast tumor cells compared to ER negative breast tumor cells and the markers of Table 3 are over-expressed in ER negative breast tumor cells compared to ER positive breast tumor cells. The present invention therefore provides methods and reagents for the diagnosis, characterization, prognosis, monitoring, and treatment of breast cancer, including the identification of ER positive and ER negative breast tumors.

The methods of the present invention comprise the step of comparing the level of expression of a marker in a patient sample, wherein the marker is listed in Table 1 and the normal level or control level of expression of the marker. A significant difference between the level of expression of the marker in the patient sample and the normal or control level is an indication that the patient is afflicted with breast cancer. A "normal" level of expression refers to the expression level of the marker in a sample from a patient without breast cancer, e.g. non-cancerous human breast tissue. A "control" level of expression refers to the expression level of the marker in an identified source, e.g. identified by phenotypic and/or genotypic analysis, e.g. clinical status. For example, the methods of the present invention comprise the step of comparing the level of expression of a marker of Table 2 (ER positive marker) in a patient sample and the level of expression of the marker in an ER negative breast tumor sample, wherein a significant difference between the level of expression of the marker in the patient sample and the ER negative breast tumor sample is an indication that the patient is afflicted with ER positive breast cancer. The level of expression of the marker in the ER negative breast tumor sample is therefore the "control."

Likewise, the methods of the present invention comprise the step of comparing the level of expression of a marker of Table 3 (ER negative marker) in a patient sample and the level of expression of a marker in an ER positive breast tumor sample, wherein a significant difference between the level of expression of the marker in the patient sample and the ER positive breast tumor sample is an indication that the patient is afflicted with ER negative breast cancer. The level of expression of the marker in the ER positive breast tumor sample is therefore the "control." Alternatively, and particularly as further information becomes available as a result of routine performance of the methods described herein, population-average values for expression of the markers of the invention may be used as the "control".

The level of expression of a marker of the present invention may thus be utilized to: (1) determine if a tumor can be treated by an agent or combination of agents; (2) determine if a tumor is responding to treatment with an agent or combination of agents; (3) select an appropriate agent or combination of agents for treating a tumor; (4) monitor the effectiveness of an ongoing treatment; and (5) identify new treatments (either single agent or combination of agents). In particular, the identified markers may be utilized to determine appropriate therapy, to monitor clinical therapy and human trials of a drug being tested for efficacy, and to develop new agents and therapeutic combinations.

In one method, the marker(s) are preferably selected such that the positive predictive value of the method is at least about 10%. Also preferred are embodiments of the method wherein the marker is over- or under-expressed by at least two-fold in at least about 20% of stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients.

In one embodiment of the methods of the present invention, the patient sample is a breast tissue-associated body fluid. Such fluids include, for example, blood fluids, lymph and cystic fluids, as well as nipple aspirates. In another embodiment, the sample comprises cells obtained from the patient. In another embodiment, the patient sample is in vivo.

In accordance with the methods of the present invention, the level of expression of the marker in a sample can be assessed, for example, by detecting the presence in the sample of:

a protein or a fragment of the protein corresponding to the marker (e.g. using a reagent, such as an antibody, an antibody derivative, or an antibody fragment, which binds specifically with the protein or a fragment of the protein)

a metabolite which is produced directly (i.e., catalyzed) or indirectly by a protein corresponding to the marker a transcribed polynucleotide (e.g. an mRNA or a cDNA), or fragment thereof, having at least a portion with which the marker is substantially homologous (e.g. by contacting a mixture of transcribed polynucleotides obtained from the sample with a substrate having one or more of the markers listed in Table 1 fixed thereto at selected positions)

a transcribed polynucleotide or fragment thereof, wherein the polynucleotide anneals with the marker under stringent hybridization conditions.

The methods of the present invention are particularly useful for patients with an identified breast mass or symptoms associated with breast cancer. The methods of the present invention can also be of particular use with patients having an enhanced risk of developing breast cancer (e.g., patients having a familial history of breast cancer, patients identified as having a mutant oncogene, and patients at least about 50 years of age). The methods of the present invention may further be of particular use in monitoring the efficacy of treatment of a breast cancer patient (e.g. the efficacy of chemotherapy).

The methods of the present invention may be performed using a plurality (e.g. 2, 3, 5, or 10 or more) of markers. According to a method involving a plurality of markers, the level of expression in the sample of each of a plurality of markers independently selected from the markers listed in Table 1 is compared with the normal or control level of expression of each of the plurality of markers. A significantly enhanced level of expression of one or more of the markers listed in Table 1 in the sample, relative to the corresponding normal levels is an indication that the patient is afflicted with breast cancer. The markers of Table 1 may also be used in combination with known breast cancer markers in the methods of the present invention.

According to an additional method involving a plurality of markers, the level of expression of each of a plurality of markers independently selected from the markers listed in Tables 2 and/or 3 is compared with the level of expression of each of the plurality of markers in a control (e.g. ER negative and/or ER positive breast cancer sample). A significantly altered level of expression of one or more of the markers listed in Tables 2 and/or 3, relative to the corresponding level in a control, is an indication that the patient is afflicted with ER positive or ER negative breast cancer. The markers of Tables 2 and/or 3 may also be used in combination with known breast cancer markers in the methods of the present invention.

In a preferred method of assessing whether a patient is afflicted with breast cancer (e.g., new detection ("screening"), detection of recurrence, reflex testing), the method comprises comparing:
   a) the level of expression of a marker in a patient sample, wherein at least one marker is selected from the markers of Table 1, and
   b) the normal level of expression of the marker in a normal sample.

A significant difference between the level of expression of the marker in the patient sample and the normal level is an indication that the patient is afflicted with breast cancer.

The methods of the present invention further include a method of assessing the efficacy of a test compound for inhibiting breast cancer in a patient. This method comprises comparing:
   a) expression of a marker in a first sample obtained from the patient and maintained in the presence of the test compound, wherein the marker is selected from the group consisting of the markers listed in Table 1, and
   b) expression of the marker in a second sample obtained from the patient and maintained in the absence of the test compound.

A significantly lower level of expression of the marker in the first sample, relative to the second sample, is an indication that the test compound is efficacious for inhibiting breast cancer in the patient. For example, the first and second samples can be portions of a single sample obtained from the patient or portions of pooled samples obtained from the patient.

The invention further relates to a method of assessing the efficacy of a therapy for inhibiting breast cancer in a patient. This method comprises comparing:
   a) expression of a marker in a first sample obtained from the patient prior to providing at least a portion of the therapy to the patient, wherein the marker is selected from the group consisting of the markers listed in Table 1, and
   b) expression of the marker in a second sample obtained from the patient following provision of the portion of the therapy.

A significantly lower level of expression of the marker in the second sample, relative to the first sample, is an indication that the therapy is efficacious for inhibiting breast cancer in the patient.

It will be appreciated that in these methods the "therapy" may be any therapy for treating breast cancer including, but not limited to, chemotherapy, radiation therapy and surgical removal of tissue, e.g., a breast tumor. Thus, the methods of the invention may be used to evaluate a patient before, during and after therapy, for example, to evaluate the reduction in tumor burden. It will also be appreciated that in these methods, the markers may be selected from Tables 2 or 3 and therefore the effect of the test compound or therapy may specifically be assessed for ER positive and ER negative breast cancers.

The present invention therefore further comprises a method for monitoring the progression of breast cancer (and specifically ER positive or ER negative breast cancer cells) in a patient, the method comprising:
   a) detecting in a patient sample at a first time point, the expression of a marker, wherein the marker is selected from the group consisting of the markers listed in Table 1;
   b) repeating step a) at a subsequent time point; and
   c) comparing the level of expression detected in steps a) and b), and therefrom monitoring the progression of breast cancer in the patient.

The invention also includes a method of selecting a composition for inhibiting breast cancer (and specifically ER positive or ER negative breast cancer cells) in a patient. This method comprises the steps of:
   a) obtaining a sample comprising cancer cells from the patient;
   b) separately maintaining aliquots of the sample in the presence of a plurality of test compositions;
   c) comparing expression of a marker listed in Table 1 in each of the aliquots; and
   d) selecting one of the test compositions which induces a lower level of expression of the marker in the aliquot containing that test composition, relative to other test compositions.

In addition, the invention includes a method of inhibiting breast cancer (and specifically ER positive or ER negative breast cancer cells) in a patient. This method comprises the steps of:
   a) obtaining a sample comprising cancer cells from the patient;
   b) separately maintaining aliquots of the sample in the presence of a plurality of test compositions;
   c) comparing expression of a marker listed in Table 1 in each of the aliquots; and d) administering to the patient at least one of the test compositions which induces a lower level of expression of the marker in the aliquot containing that test composition, relative to other test compositions.

The invention also includes a kit for assessing whether a patient is afflicted with breast cancer (and specifically ER positive or ER negative breast cancer). This kit comprises reagents for assessing expression of a marker listed in Table 1.

In another aspect, the invention relates to a kit for assessing the suitability of each of a plurality of compounds for inhibiting breast cancer (and specifically ER positive or ER negative breast cancer) in a patient. The kit comprises a reagent for assessing expression of a marker listed in Table 1, and may also comprise a plurality of compounds.

In another aspect, the invention relates to a kit for assessing the presence of breast cancer cells (and specifically ER positive or ER negative breast cancer cells). This kit comprises an antibody, wherein the antibody binds specifically with a protein corresponding to a marker listed in Table 1. The kit may also comprise a plurality of antibodies, wherein the plurality binds specifically with a protein corresponding to a different marker which is also listed in Table 1.

The invention also includes a kit for assessing the presence of breast cancer cells (and specifically ER positive or ER negative breast cancer cells), wherein the kit comprises a nucleic acid probe. The probe binds specifically with a transcribed polynucleotide corresponding to a marker listed in Table 1. The kit may also comprise a plurality of probes, wherein each of the probes binds specifically with a transcribed polynucleotide corresponding to a different marker listed in Table 1.

The invention further relates to a method of making an isolated hybridoma which produces an antibody useful for assessing whether a patient is afflicted with breast cancer (and specifically ER positive or ER negative breast cancer). The method comprises isolating a protein or protein fragment corresponding to a marker listed in Table 1, immunizing a mammal using the isolated protein or protein fragment, isolating splenocytes from the immunized mammal, fusing the isolated splenocytes with an immortalized cell line to form hybridomas, and screening individual hybridomas for production of an antibody which specifically binds with the protein or protein fragment to isolate the hybridoma. The invention also includes an antibody produced by this method.

The invention further includes a method of assessing the breast carcinogenic or irregular growth promoting potential of a test compound. This method comprises the steps of:
 a) maintaining separate aliquots of breast cells in the presence and absence of the test compound; and
 b) comparing expression of a marker in each of the aliquots.

The marker is selected from those listed in Table 1. A significantly enhanced level of expression of the marker in the aliquot maintained in the presence of (or exposed to) the test compound, relative to the aliquot maintained in the absence of the test compound, is an indication that the test compound possesses breast carcinogenic or irregular growth promoting potential.

Additionally, the invention includes a kit for assessing the breast carcinogenic potential of a test compound. The kit comprises breast cells and a reagent for assessing expression of a marker in each of the aliquots. The marker is selected from those listed in Table 1.

The invention further includes a method of treating a patient afflicted with breast cancer, comprising providing to cells of the patient an antisense oligonucleotide complementary to a polynucleotide corresponding to a marker listed in Table 1.

The invention includes a method of inhibiting breast cancer in a patient at risk for developing breast cancer. This method comprises inhibiting expression or overexpression of a marker listed in Table 1.

The present invention further provides methods for determining whether an agent, e.g., a chemotherapeutic agent, can be used to reduce the growth rate of a tumor comprising the steps of:
 a) obtaining a sample of tumor cells;
 b) determining whether the tumor cells express one or more markers identified in Table 1; and
 c) identifying that an agent is or is not appropriate to treat the tumor based on the expression level of one or more markers identified in Table 1.

Accordingly, the present invention also provides methods for determining whether an agent, e.g., a chemotherapeutic agent, can be used to reduce the growth rate of an ER positive breast tumor comprising the steps of:
 a) obtaining a sample of tumor cells;
 b) determining whether the tumor cells express one or more markers identified in Table 2; and
 c) identifying that an agent is or is not appropriate to treat the tumor based on the expression level of one or more markers identified in Table 2.

The present invention further provides methods for determining whether an agent, e.g., a chemotherapeutic agent, can be used to reduce the growth rate of an ER negative breast tumor comprising the steps of:
 a) obtaining a sample of tumor cells;
 b) determining whether the tumor cells express one or more markers identified in Table 3; and
 c) identifying that an agent is or is not appropriate to treat the tumor based on the expression level of one or more markers identified in Table 3.

In another embodiment, the invention provides a method for determining whether an agent can be used to reduce the growth of a tumor, comprising the steps of:
 a) obtaining a sample of tumor cells;
 b) exposing some of the tumor cells to one or more test agents;
 c) determining the level of expression of one or more markers identified in Table 1 both in tumor cells exposed to the agent and in tumor cells that have not been exposed to the agent; and
 d) identifying that an agent is appropriate to treat the tumor when the expression of the markers identified in Table 1 is decreased in the presence of the agent.

Alternatively, in step (d), an agent can be identified as not being appropriate to treat the tumor when the expression of the markers identified in Table 1 is increased in the presence of the agent.

In another embodiment, the invention provides a method for determining whether an agent can be used to reduce the growth of an ER positive breast tumor, comprising the steps of:
 a) obtaining a sample of tumor cells;
 b) exposing some of the tumor cells to one or more test agents;
 c) determining the level of expression of one or more markers identified in Table 2 both in tumor cells exposed to the agent and in tumor cells that have not been exposed to the agent; and d) identifying that an agent is appropriate to treat the tumor when the expression of the markers identified in Table 2 is decreased in the presence of the agent.

Alternatively, in step (d), an agent can be identified as not being appropriate to treat the tumor when the expression of the markers identified in Table 2 is increased in the presence of the agent.

In another embodiment, the invention provides a method for determining whether an agent can be used to reduce the growth of an ER negative breast tumor, comprising the steps of:
a) obtaining a sample of tumor cells;
b) exposing some of the tumor cells to one or more test agents;
c) determining the level of expression of one or more markers identified in Table 3 both in tumor cells exposed to the agent and in tumor cells that have not been exposed to the agent; and
d) identifying that an agent is appropriate to treat the tumor when the expression of the markers identified in Table 3 is decreased in the presence of the agent.

Alternatively, in step (d), an agent can be identified as not being appropriate to treat the tumor when the expression of the markers identified in Table 3 is increased in the presence of the agent.

In another embodiment, the invention provides a method for determining whether treatment with an anti-cancer agent should be continued in a cancer patient, comprising the steps of:
a) obtaining two or more samples of breast cells from a patient at different times during the course of anti-cancer agent treatment;
b) determining the level of expression in the breast cells of one or more markers identified in Table 1 in the two or more samples; and
c) continuing the treatment when the expression level of the markers identified in Table 1 does not increase during the course of treatment.

Alternatively, in step (c), the treatment is discontinued when the expression level of the markers identified in Table 1 is increased during the course of treatment.

In another embodiment, the present invention also provides methods for detecting a patient sample containing tumor cells, comprising the steps of:
a) obtaining a sample of cells;
b) determining whether the cells express one or more markers identified in Table 1.

In another embodiment, the present invention provides methods for detecting a patient sample containing ER positive breast tumor cells, comprising the steps of:
a) obtaining a sample of cells;
b) determining whether the cells express one or more markers identified in Table 2.

The present invention further provides methods for detecting a patient sample containing ER negative breast tumor cells, comprising the steps of:
a) obtaining a sample of cells;
b) determining whether the cells express one or more markers identified in Table 3.

In another embodiment, the invention provides a method for determining whether treatment with an anti-cancer agent should be continued in a cancer patient identified as having an ER positive breast tumor, comprising the steps of:
a) obtaining two or more samples of breast cells from a patient at different times during the course of anti-cancer agent treatment;
b) determining the level of expression in the cells of one or more genes which correspond to markers identified in Table 2 in the two or more samples; and
c) continuing the treatment when the expression level of the markers identified in Table 2 does not increase during the course of treatment.

Alternatively, in step (c), the treatment is discontinued when the expression level of the markers identified in Table 2 is increased during the course of treatment.

In another embodiment, the invention provides a method for determining whether treatment with an anti-cancer agent should be continued in a cancer patient identified as having an ER negative breast tumor, comprising the steps of:
a) obtaining two or more samples of breast cells from a patient at different times during the course of anti-cancer agent treatment;
b) determining the level of expression in the cells of one or more markers identified in Table 3 in the two or more samples; and
c) continuing the treatment when the expression level of the markers identified in Table 3 does not increase during the course of treatment.

Alternatively, in step (c), the treatment is discontinued when the expression level of the markers identified in Table 3 is increased during the course of treatment.

The present invention further provides a method for identifying an appropriate course of treatment for a patient, comprising the steps of:
a) obtaining a sample of breast cells from the patient;
b) determining whether the cells express one or more markers identified in Table 2; and
c) identifying that a therapy effective for treating ER positive breast cancer should be administered to the patient when one or more markers identified in Table 2 is expressed.

Alternatively, in step (c), a therapy can be identified as not being appropriate when one or more markers identified in Table 2 are not expressed.

The present invention further provides a method of therapy for identifying an appropriate course of treatment for a patient comprising the steps of:
a) obtaining a sample of breast cells from the patient;
b) determining whether the cells express one or more markers identified in Table 3; and
c) identifying that a therapy effective for treating ER negative breast cancer should be administered to the patient when one or more markers identified in Table 3 is expressed.

Alternatively, in step (c), a therapy can be identified as not being appropriate when one or more markers identified in Table 3 are not expressed.

It will be appreciated that the methods described herein may be combined with other methods for determining tumor cell phenotype (e.g. growth factor and hormone receptor status) for further detecting, characterizing, managing, and treating breast cancer. For example, the methods of the present invention may be combined with methods for determining the expression of levels of BRCA1, BRCA2 and/or HER-2, as well as methods for identifying whether a breast tumor is a luminal or epithelial type of tumor. The level of expression of these additional breast cancer-related genes may be determined by routine immunohistochemistry (IHC) and transcriptional profiling, as discussed in West et al. (2001) *PNAS* 2001 98:11462-11467 and U.S. Pat. No. 4,968,603 incorporated herein by reference.

In another embodiment, the invention provides a method of treating a patient for breast cancer by administering to the patient an agent which has been identified as being effective by the methods of the present invention. As used herein, the term "agent" is defined broadly as anything that cancer cells, including tumor cells, may be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., inblastine and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. The term "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases.

DETAILED DESCRIPTION OF THE INVENTION

The invention relates to newly discovered correlations between expression of certain markers and the cancerous state of breast cells. It has been discovered that the level of expression of individual markers and combinations of markers described herein correlates with the presence of breast cancer tumors in a patient. Methods are provided for detecting the presence of breast cancer in a sample, the absence of breast cancer in a sample, the stage of breast cancer, the type of breast cancer, and other characteristics of breast cancer that are relevant to prevention, diagnosis, characterization, and therapy of breast cancer in a patient.

Table 1, markers n1-n736, lists all of the markers of the invention (and comprises markers listed in Tables 2 and 3), which are over-expressed in breast cancer cells compared to normal (i.e., non-cancerous) cells. Table 2, markers n1-n302, lists markers which are over-expressed in estrogen receptor positive breast tumors ("ER positive markers") as compared to estrogen receptor negative breast tumors. Table 3, markers n303-n736, lists markers which are over-expressed in estrogen receptor negative breast tumors ("ER negative markers") as compared to estrogen receptor positive breast tumors. All tables include a marker identification number ("Marker"), the gene corresponding to the marker ("Gene Name"), the Image Clone ID ("Image Clone ID"), the Image Clone Accession Number ("Image Clone Accession #"), the Image Clone GI Number ("Image Clone GI #"), and the Genebank or Reference Sequence Nucleic Accession Number ("Genebank or RefSeq nuc accession #").

TABLE 1

| Marker | Gene Name | Image Clone ID | Image Clone Accession # | Image Clone GI # | Genebank or RefSeq nuc accession # |
|---|---|---|---|---|---|
| n1 | CGI-49 protein | 123255 | R00275 | 750011 | NM_016002 |
|  |  |  | T99925 | 749662 |  |
| n2 | Unamed | 490965 | AA120865 | 1678196 |  |
|  |  |  | AA120866 | 1678197 |  |
| n3 | Laminin, beta 2 | 502518 | AA156802 | 1728435 | NM_002292 |
|  |  |  | AA156926 | 1728541 |  |
| n4 | Unamed | 279837 | N38839 | 1162046 |  |
| n5 | Synaptotagmin-like 2 | 487932 | AA045284 | 1523712 | NM_032379 |
|  |  | 826194 | AA046565 | 1524462 | NM_032943 |
|  |  |  | AA521439 | 2261982 |  |
| n6 | Unamed | 29967 | R14766 | 769039 |  |
|  |  |  | R42536 | 817298 |  |
| n7 | Unamed | 841621 | AI732756 | 2217632 |  |
|  |  |  | AI734150 | 2217847 |  |
|  |  |  | AA487683 |  |  |
|  |  |  | AA487468 |  |  |
| n8 | Plasminogen activator | 813841 | AA447797 | 2161467 | NM_000930 |
|  |  |  | AA453728 | 2167397 | NM_000931 |
|  |  |  |  |  | NM_033011 |
| n9 | GDNF family receptor alpha 1 | 1641451 | AI024284 | 3239897 | NM_005264 |
| n10 | Estrogen receptor 1 | 725321 | AA291749 | 1939868 | NM_000125 |
|  |  |  | AA291702 | 1939745 |  |
| n11 | Suppressor of *S. cerevisiae* gcr2 | 25154 | T80582 | 796389 | NM_007265 |
|  |  |  | R38933 | 699091 |  |
| n12 | *Homo sapiens* clone 25194 mRNA sequence | 155227 | AI732288 | 843038 |  |
|  |  |  | R69521 | 843039 |  |
|  |  |  | R69522 |  |  |
| n13 | *Homo sapiens* cDNA FLJ10561 | 1554430 | AA931491 | 3085877 |  |
| n14 | Unamed | 392630 | AA708301 | 2718219 |  |
| n15 | Reticulon 1 | 858450 | AA773983 | 2825872 | NM_021136 |
| n16 | Unamed | 25194 | R39044 | 796500 |  |
| n17 | netrin 4 | 143661 | R76613 | 851262 | NM_021229 |
|  |  |  | R76614 | 851263 |  |
| n18 | non-metastatic cells 3, protein expressed in | 726658 | AA398218 | 2051345 | NM_002513 |
|  |  |  | AA399289 | 2053042 |  |
| n19 | Unamed | 784282 | AA447486 | 2161155 |  |
|  |  |  |  | 2161156 |  |
| n20 | trefoil factor 3 | 298417 | N74131 | 1231416 | NM_003226 |
| n21 | *Homo sapiens* mRNA; cDNA DKFZp434E082 | 44387 | H06525 | 870057 |  |
|  |  |  | H06580 | 870112 |  |
| n22 | *Homo sapiens* mRNA; cDNA DKFZp434N2412 | 772890 | AA479888 | 2112474 |  |
|  |  |  |  | 2204370 |  |

TABLE 1-continued

| Marker | Gene Name | Image Clone ID | Image Clone Accession # | Image Clone GI # | Genebank or RefSeq nuc accession # |
|---|---|---|---|---|---|
| n23 | LIV-1 protein, estrogen regulated | 52933 | H29315 | 900225 | NM_012319 |
|  |  |  | H29407 | 900317 |  |
| n24 | Unamed | 51700 | H22853 | 891548 |  |
|  |  |  | H22854 | 891549 |  |
| n25 | Unamed | 52021 | H24419 | 891261 |  |
|  |  |  | H22566 | 893114 |  |
| n26 | GATA-binding protein 3 | 214068 | H72474 | 1044290 | NM_002051 |
|  |  | 365681 | H72875 | 1044691 | NM_032742 |
|  |  |  | AA025380 | 1490899 |  |
|  |  |  | AA025379 | 1490900 |  |
| n27 | UDP-glucose ceramide glucosyltransferase | 739123 | AA421691 | 2100508 | NM_003358 |
|  |  |  | AA421692 | 2100509 |  |
| n28 | Homo sapiens, clone MGC 17687 IMAGE 3865868 | 214205 | H77627 | 1055716 |  |
|  |  |  |  | 1055886 |  |
| n29 | UDP-glucose ceramide glucosyltransferase | 302540 | W38595 | 1443531 | NM_003358 |
|  |  |  | N90204 | 1320257 |  |
| n30 | vav 3 oncogene | 46827 | H10098 | 874867 | NM_006113 |
|  |  | 415229 | H10045 | 874920 |  |
|  |  |  | W91879 | 1424261 |  |
|  |  |  | W91952 | 1424313 |  |
| n31 | CEGP1 protein | 346321 | W79647 | 1384330 | NM_020974 |
|  |  | 242778 | W74079 | 1390075 |  |
|  |  |  | H93602 | 1099930 |  |
|  |  |  | H93603 | 1099931 |  |
| n32 | solute carrier family 2, member 10 | 429263 | AA007343 | 1463347 | NM_030777 |
|  |  | 758347 | AA007344 | 1463348 |  |
|  |  |  | AA403072 | 2055616 |  |
|  |  |  | AA404352 | 2059077 |  |
| n33 | Homo sapiens mRNA; cDNA DKFZp727C191 | 785703 | AA449591 | 2163183 |  |
|  |  |  | AA449334 | 2163341 |  |
| n34 | Unamed | 279838 | N38836 | 1162043 |  |
| n35 | Unamed | 282980 | N45139 | 1186305 |  |
| n36 | Unamed | 33985 | R44918 | 823185 |  |
| n37 | Homo sapiens mRNA; cDNA DKFZp564F053 | 78041 | T61343 | 663537 |  |
|  |  |  | T60500 | 664380 |  |
| n38 | Unamed | 49567 | H15113 | 879933 |  |
|  |  |  | H15114 | 879934 |  |
| n39 | LIM and SH3 protein 1 | 392093 | AI003699 | 3204033 | NM_006148 |
| n40 | Hypothetical protein FLJ12910 | 785795 | AA449754 | 2163058 | NM_024573 |
|  |  |  | AA449038 | 2163504 |  |
| n41 | Unamed | 291462 | N72847 | 1229951 |  |
|  |  |  | W03066 | 1275044 |  |
| n42 | GLI-Kruppel family member GLI3 | 767495 | AA418036 | 2079847 | NM_000168 |
|  |  |  | AA418190 | 2080009 |  |
| n43 | Unamed | 882467 | AA676408 | 2656930 |  |
| n44 | Homo sapiens mRNA; cDNA DKFZp586G0321 | 504959 | AA149050 | 1719458 |  |
|  |  |  | AA149051 | 1719459 |  |
| n45 | v-myb avian myeloblastosis viral oncogene homolog | 243549 | N49526 | 1190450 | NM_005375 |
|  |  |  | N49284 | 1190692 |  |
| n46 | Chondroadherin | 1507713 | AA937215 | 3095326 | NM_001267 |
| n47 | KIAA0100 gene product | 1631355 | AI024502 | 3240115 | NM_014680 |
| n48 | Duodenal cytochrome b | 244310 | N75713 | 1196108 | NM_024843 |
|  |  | 838446 | N54788 | 1238291 |  |
|  |  |  | AA457501 | 2180221 |  |
|  |  |  | AA457594 | 2180314 |  |
| n49 | Cbp p300-interacting transactivator, with Glu | 491565 | AA115076 | 1670339 | NM_006079 |
| n50 | Unamed | 812041 | AA455976 | 2178752 |  |
| n51 | Dachshund (Drosophila) homolog | 132326 | R25458 | 781593 | NM_004392 |
|  |  |  | R26283 | 782418 |  |
| n52 | Neuropeptide Y receptor Y1 | 33045 | R43817 | 773088 | NM_000909 |
|  |  | 143332 | R19478 | 821697 |  |
|  |  |  | R74183 | 848553 |  |
|  |  |  | R74269 | 848639 |  |
| n53 | Unamed | 1031791 | AA609651 | 2458079 |  |
| n54 | Homo sapiens mRNA; cDNA DKFZp434E2321 | 590310 | AA157456 | 1727904 |  |
|  |  |  | AA156269 | 1729063 |  |
| n55 | Unamed | 282564 | N52073 | 1193239 |  |
| n56 | protein tyrosine phosphatase, receptor type, T | 41647 | R52793 | 814695 | NM_007050 |
|  |  |  | R52794 | 814696 |  |
| n57 | Anterior gradient 2 (Xenepus laevis) homolog | 510576 | AA055768 | 1548168 | NM_006408 |
|  |  |  | AA055880 | 1548218 |  |
| n58 | X-box binding protein 1 | 417867 | W90224 | 1406118 | NM_005080 |
|  |  |  | W90128 | 1406214 |  |

TABLE 1-continued

| Marker | Gene Name | Image Clone ID | Image Clone Accession # | Image Clone GI # | Genebank or RefSeq nuc accession # |
|---|---|---|---|---|---|
| n59 | Interleukin 6 signal transducer | 2018581 | AI360116 | 4111737 | NM_002184 |
| | | 753743 | AA406546 | 2064660 | |
| | | | | 2069400 | |
| n60 | RNB6 | 26294 | R20625 | 766580 | NM_016337 |
| | | | R13504 | 775406 | |
| n61 | Unamed | 365665 | AA025386 | 1491525 | |
| | | | AA026030 | 1491449 | |
| n62 | HMBA-inducible | 897722 | AA598983 | 2432023 | NM_006460 |
| n63 | Cysteine-rich protein 1 | 1323448 | AA873604 | 2969726 | NM_001311 |
| n64 | Unamed | 399463 | AA732944 | 2754303 | |
| n65 | Carboxypeptidase B1 | 2063284 | AI382830 | 4195611 | NM_001871 |
| n66 | Unamed | 39577 | R51889 | 813791 | |
| | | | R54279 | 816181 | |
| n67 | nuclear receptor subfamily 5, group A, member 2 | 128457 | R10138 | 762094 | NM_003822 |
| | | | | 762501 | |
| n68 | Unamed | 260170 | N32072 | 1152471 | |
| | | | N45384 | 1186550 | |
| n69 | solute carrier family 12 (sodium potassium | 685801 | AA255695 | 1892633 | NM_001046 |
| | | | AA262080 | 1898204 | |
| n70 | Phosphorylase, glycogen; liver | 241705 | H91680 | 1087258 | NM_002863 |
| | | | H91776 | 1087354 | |
| n71 | Androgen induced protein | 66977 | T69554 | 678706 | NM_016108 |
| | | | T67558 | 680702 | |
| n72 | Hypothetical protein CAB56184 | 502349 | AA135715 | 1697220 | NM_032520 |
| | | | AA156935 | 1728550 | |
| n73 | Purinergic receptor P2X, ligand-gated ion channel, 4 | 42118 | R60722 | 831417 | NM_002560 |
| | | | R60723 | 831418 | |
| n74 | Homo sapiens cDNA FLJ12425 | 51103 | H19216 | 885456 | |
| | | | H19217 | 885457 | |
| n75 | N-acetyltransferase 1 | 195525 | R91802 | 959342 | NM_000662 |
| | | 66599 | R91803 | 959343 | |
| | | | T67129 | 676568 | |
| | | | | 676569 | |
| n76 | DEME-6 protein | 1492468 | AA886199 | 3001307 | |
| n77 | lectin, galactoside-binding, soluble, 8 | 197903 | R96336 | 981996 | NM_006499 |
| | | | R96337 | 981997 | |
| n78 | SH3 domain binding glutamic acid-rich protein like | 1603583 | AA996131 | 3182620 | NM_003022 |
| n79 | Receptor activity modifying protein 3 | 345663 | W76411 | 1382349 | NM_005856 |
| | | | W72393 | 1386655 | |
| n80 | leucine zipper transcription factor-like 1 | 754033 | AA479063 | 2207619 | NM_020347 |
| | | | AA480036 | 2208187 | |
| n81 | Transcription elongation factor A (SII)-like 1 | 786607 | AA478480 | 2165638 | NM_004780 |
| | | | AA451969 | 2207114 | |
| n82 | Hypothetical protein FLJ12890 | 292270 | N79195 | 1210304 | NM_015442 |
| | | | N62475 | 1241896 | |
| n83 | Hypothetical protein FLJ12650 | 41569 | R67272 | 814803 | NM_024522 |
| | | | R52900 | 839910 | |
| | | | R52901 | | |
| n84 | G protein-coupled receptor | 246786 | N53172 | 1194338 | |
| | | | | 1202499 | |
| n85 | RAB31 | 785701 | AA449590 | 2163182 | NM_006868 |
| | | 120881 | AA449333 | 2163340 | |
| | | | T96082 | 734706 | |
| | | | T96083 | 734707 | |
| n86 | Unamed | 377987 | AA788874 | 2848994 | |
| n87 | Stanniocalcin 1 | 547247 | AA085318 | 1627385 | NM_003155 |
| | | | AA085319 | 1627386 | |
| n88 | Secretory carrier membrane protein 1 | 824025 | AA490945 | 2220118 | NM_004866 |
| n89 | Unamed | 669359 | AA236793 | 1860813 | |
| | | | AA236840 | 1860870 | |
| n90 | Unamed | 742596 | AA400080 | 2053883 | |
| | | | | 2054012 | |
| n91 | acyl-Coenzyme A oxidase 2, branched chain | 85450 | T71782 | 686234 | NM_003500 |
| | | | T71713 | 686303 | |
| n92 | serine proteinase inhibitor, clade A, member 5 | 416567 | W86431 | 1400197 | NM_000624 |
| | | | | 1400198 | |
| n93 | Hypothetical gene BC008967 | 782497 | AA431770 | 2115478 | |
| | | | AA432023 | 2115731 | |
| n94 | Unamed | 33821 | R45924 | 774460 | |
| | | | R19826 | 824257 | |
| n95 | Stanniocalcin 2 | 823578 | AA497118 | 2230361 | NM_003714 |
| | | 130057 | AA497040 | 2230439 | |
| | | | R20886 | 775560 | |
| | | | R20779 | 775667 | |

TABLE 1-continued

| Marker | Gene Name | Image Clone ID | Image Clone Accession # | Image Clone GI # | Genebank or RefSeq nuc accession # |
|---|---|---|---|---|---|
| n96 | *Homo sapiens* clone 24566 mRNA sequence | 165807 | R86667 | 945518 945478 | |
| n97 | gap junction protein, alpha 1, 43 kD | 839101 | AA487623 | 2217787 | NM_000165 |
| n98 | Unamed | 726580 | AA394105 AA398134 | 2047093 2051243 | |
| n99 | normal mucosa of esophagus specific 1 | 1056172 | AA620995 | 2524934 | NM_032413 |
| n100 | Unamed | 155072 | AI732325 R71393 AI820748 | 5439827 844910 | |
| n101 | Unamed | 33076 | R18933 R44048 | 772543 821916 | |
| n102 | Fibroblast growth factor receptor 1 | 154472 | R54610 R54846 | 819042 818968 | NM_000604 NM_023105 NM_023106 NM_023107 NM_023108 NM_023109 NM_023110 NM_023111 NM_015850 |
| n103 | *Homo sapiens* genomic DNA, chromosome 21q, section 4 | 461284 | AA699859 | 2702822 | |
| n104 | Hypothetical protein FLJ11026 | 249784 | H84010 H84011 | 1062681 1062682 | NM_018303 |
| n105 | Chitinase 1 | 119384 | T94272 T94579 | 727760 728067 | NM_003465 |
| n106 | Unamed | 854831 | AA630241 | 2552852 | |
| n107 | Unamed | 795907 | AA460346 AA460775 | 2185559 2185895 | |
| n108 | Unamed | 42415 | R60981 R61649 | 831676 832344 | |
| n109 | Hypothetical protein FLJ13110 | 782306 | AA431233 AA432253 | 2114941 2114641 | NM_022912 |
| n110 | RAB38, member RAS oncogene family | 263047 | N20045 | 1124712 | NM_022337 |
| n111 | pre-B-cell leukemia transcription factor 1 | 2018074 741880 | AI364369 AA403031 AA401304 | 4124058 2053547 2056768 | NM_002585 |
| n112 | 5'–3' exoribonuclease 2 | 364840 | AA035728 AA028164 | 1494289 1507565 | NM_012255 |
| n113 | Coxsackie virus and adenovirus receptor | 276712 | N46621 N34895 | 1156037 1187787 | NM_001338 |
| n114 | *Homo sapiens* cDNA FLJ12993 fis, clone NT2RP3000197 | 950410 | AA599064 | 2432689 | |
| n115 | Polymerase (DNA-directed), delta 4 | 810734 | AA480820 AA457710 | 2180430 2210372 | NM_021173 |
| n116 | *Homo sapiens* cDNA FLJ11685 | 796152 | AA461390 AA461078 | 2186198 2185254 | |
| n117 | WW domain-containing protein 1 | 141959 | R67561 R67562 | 840199 840200 | NM_007013 |
| n118 | Unamed | 813168 | AA456306 AA456704 | 2179516 2179280 | |
| n119 | Pregnancy specific beta-1-glycoprotein 1 | 199635 | R96522 R96568 | 982182 982228 | NM_006905 |
| n120 | Programmed cell death 9 | 270558 | N33236 | 1153635 | NM_016640 |
| n121 | Synaptotagmin XIII | 23443 | R38678 T75313 | 796134 692075 | |
| n122 | Unamed | 754260 | AA479272 | 2207828 2207924 | |
| n123 | Hypothetical protein FLJ21213 | 1572710 | AA969799 | 3145312 | NM_022900 |
| n124 | Hypothetical protein FLJ22724 | 772944 | AA425184 | 2105976 2204462 | NM_024532 |
| n125 | Glypican 3 | 878564 | AA775872 | 2835206 | NM_004484 |
| n126 | Hypothetical protein similar to small G proteins, especially RAP-2A | 487929 | AA045481 AA046513 | 1523717 1524468 | NM_021183 |
| n127 | Unamed | 48642 | H14677 H14583 | 879403 879497 | |
| n128 | N-acylsphingosine amidohydrolase | 855487 | AA664155 | 2618146 | NM_004315 |
| n129 | Amphiregulin | 1410444 | AA857163 | 2945465 | NM_001657 |
| n130 | KIAA0942 protein | 666451 731240 | AA232926 AA232939 AA417363 AA416817 | 1856039 1855931 2077776 2077673 | NM_015310 |
| n131 | Unamed | 450327 | AA703619 | 2713537 | |

TABLE 1-continued

| Marker | Gene Name | Image Clone ID | Image Clone Accession # | Image Clone GI # | Genebank or RefSeq nuc accession # |
|---|---|---|---|---|---|
| n132 | Unamed | 824995 | AA489100 | 2218702 | |
| | | | AA489185 | 2218787 | |
| n133 | Ribosomal protein S23 | 868308 | AA634008 | 2557222 | NM_001025 |
| n134 | Duodenal cytochrome b | 491415 | AA150422 | 1721935 | NM_024843 |
| | | | AA156591 | 1728233 | |
| n135 | Unamed | 767706 | AA417956 | 2079775 | |
| | | | AA418061 | 2079935 | |
| n136 | *Homo sapiens* cDNA FLJ11663 fis, clone HEMBA 1004631 | 1291971 | AA707477 | 2717395 | |
| n137 | Parathyroid hormone-like hormone | 1404774 | AA845432 | 2933191 | NM_002820 |
| n138 | C-type lectin, superfamily member 1 | 726645 | AA399390 | 2051339 | NM_005752 |
| | | | AA398015 | 2053135 | |
| n139 | CD44 antigen | 328868 | W40475 | 1324428 | NM_000610 |
| | | 713145 | W45275 | 1329588 | |
| | | | AA283090 | 1925839 | |
| | | | AA282906 | 1926015 | |
| n140 | Unamed | 855634 | AA664105 | 2618096 | |
| n141 | Attractin | 47626 | H11351 | 876145 | NM_012070 |
| | | | H11325 | 876171 | |
| n142 | PDZ domain protein | 428338 | AA005153 | 1447808 | NM_005799 |
| | | | AA005420 | 1447902 | |
| n143 | Unamed | 32092 | R17347 | 770957 | |
| | | | R42695 | 819640 | |
| n144 | Programmed cell death 4 (neoplastic transformation inhibitor) | 294487 | N71003 | 1227583 | NM_014456 |
| | | | | 1273516 | |
| n145 | *Homo sapiens* cDNA FLJ13603 fis, | 506128 | AA708864 | 2718782 | |
| n146 | Glutamate receptor, ionotropic, AMPA 2 | 364141 | AA021212 | 1484937 | NM_000826 |
| | | 282958 | AA021343 | 1485032 | |
| | | 49987 | N45132 | 1186298 | |
| | | | H28734 | 899688 | |
| | | | H28864 | 899774 | |
| n147 | DKFZP564K247 protein | 84613 | T74479 | 690780 | NM_014056 |
| | | | T74105 | 691154 | |
| n148 | Hypothetical protein MGC2771 | 1558642 | AA976544 | 3153990 | NM_024101 |
| n149 | Parathyroid hormone | 322051 | W37305 | 1319036 | NM_000315 |
| | | | W37306 | 1319037 | |
| n150 | Unamed | 810235 | AA464707 | 2189591 | |
| n151 | *Homo sapiens*, Similar to clone FLB3816, | 130835 | R22198 | 776979 | |
| | | | R22252 | 777033 | |
| n152 | Pregnancy specific beta-1-glycoprotein 11 | 143287 | R74004 | 848279 | NM_002785 |
| | | | R73909 | 848374 | |
| n153 | Hypothetical protein FLJ22087 | 510575 | AA057741 | 1550400 | NM_022070 |
| | | | AA057742 | 1550401 | |
| n154 | Eukaryotic translation initiation factor 2C, 1 | 813850 | AA453723 | 2161461 | NM_012199 |
| | | | AA447791 | 2167392 | |
| n155 | Pregnancy specific beta-1-glycoprotein 9 | 141677 | R69567 | 843084 | NM_002784 |
| | | | R69649 | 843166 | |
| n156 | Glutathione S-transferase M3 | 137940 | R63106 | 834944 | NM_000849 |
| | | | R63065 | 834985 | |
| n157 | Hypothetical protein PRO2975 | 684073 | AA251288 | 1886198 | |
| | | | AA251217 | 1886269 | |
| n158 | KIAA0728 protein | 51708 | H24092 | 891609 | |
| | | | H22914 | 892787 | |
| n159 | Meis homolog 3 | 450152 | AA703449 | 2713367 | |
| n160 | bone morphogenetic protein 4 | 797048 | AA463225 | 2188108 | NM_001202 |
| | | | AA463224 | 2188109 | |
| n161 | Unamed | 1292170 | AA705819 | 2715737 | |
| n162 | low density lipoprotein-related protein 2 | 143846 | R75977 | 850659 | NM_004525 |
| | | | R76808 | 851440 | |
| n163 | Unamed | 252830 | H88261 | 1069629 | |
| | | | | 1069840 | |
| n164 | Ectonucleoside triphosphate diphosphohydrolase 5 | 1635701 | AI017442 | 3231778 | NM_001249 |
| n165 | Ectonucleotide pyrophosphatase | 322461 | W15305 | 1289705 | NM_021572 |
| | | 82991 | T70503 | 680598 | |
| | | 281737 | T69450 | 681651 | |
| | | | N51740 | 1192906 | |
| n166 | Hypothetical protein | 594600 | AA171951 | 1750797 | NM_019049 |
| | | | AA171739 | 1751010 | |
| n167 | Unamed | 275372 | R85509 | 943915 | |
| n168 | Glutathione S-transferase M5 | 377731 | AA056231 | 1548568 | NM_000851 |
| | | | AA056232 | 1548569 | |
| n169 | Cytochrome P450, subfamily IVB, polypeptide 1 | 724888 | AA404692 | 1939505 | NM_000779 |
| | | | AA291484 | 2058871 | |

TABLE 1-continued

| Marker | Gene Name | Image Clone ID | Image Clone Accession # | Image Clone GI # | Genebank or RefSeq nuc accession # |
|---|---|---|---|---|---|
| n170 | serine proteinase inhibitor, clade A (alpha-1 antiproteinase, antitrypsin), member 6 | 240518 | H90764<br>H90815 | 1081194<br>1081245 | NM_001756 |
| n171 | amylo-1,6-glucosidase, 4-alpha-glucanotransferase | 853687 | AA668425 | 2629924 | NM_000028<br>NM_000642<br>NM_000643<br>NM_000644<br>NM_000645<br>NM_000646 |
| n172 | Collagen, type IV, alpha 5 | 470001 | AA029107<br>AA029997 | 1496528<br>1496428 | NM_000495 |
| n173 | Corticotropin releasing hormone-binding protein | 266336 | N35660<br>N26546 | 1140894<br>1156802 | NM_001882 |
| n174 | KIAA0040 gene product | 814054 | AA465478<br>AA465479 | 2191645<br>2191646 | NM_014656 |
| n175 | Stathmin-like 3 | 1631253 | AA994305 | 3180850 | NM_015894 |
| n176 | Hypothetical protein FLJ10261 | 742679 | AA400086<br>AA401376 | 2053906<br>2053584 | NM_018043 |
| n177 | Unamed | 49919 | H29088<br>H28983 | 899893<br>899998 | |
| n178 | Pleiotrophin | 361974 | AA001449 | 1436914<br>1436950 | NM_002825 |
| n179 | sodium channel, voltage gated, type VIII, alpha polypeptide | 361668 | W96187<br>W96278 | 1426093<br>1426185 | NM_014191 |
| n180 | Hypothetical protein DKFZp566I133 | 824908 | AA489012<br>AA489105 | 2218614<br>2218707 | NM_030938 |
| n181 | tumor necrosis factorsuperfamily, member 13 | 771240 | AA443577 | 2156252 | NM_003808 |
| n182 | Ortholog of mouse integral membrane glycoprotein LIG-1 | 878094 | AA775396 | 2834730 | |
| n183 | Glutamate dehydrogenase 1 | 361565 | AA017175<br>AA018372 | 1479340<br>1481628 | NM_005271 |
| n184 | Hypothetical protein DKFZp434P0116 | 417863<br>264609 | W89179<br>W88781<br>N20237<br>N29303 | 1404472<br>1404471<br>1125192<br>1147539 | NM_017593 |
| n185 | Unamed | 324236 | AA284185<br>W47507<br>W47508 | 1928530<br>1332158 | |
| n186 | sema domain, immunoglobulin domain (Ig), short basic domain, secreted, 3C | 486591 | AA043044<br>AA042990 | 1522505<br>1522624 | NM_006379 |
| n187 | Hypothetical protein FLJ10374 | 897159 | AA676962 | 2657484 | NM_018074 |
| n188 | NK homeobox, family 3, A | 757435 | AA437224<br>AA442287 | 2142138<br>2154165 | NM_006167 |
| n189 | Epiregulin | 271744 | N42596<br>N31585 | 1151984<br>1167026 | NM_001432 |
| n190 | acyl-Coenzyme A dehydrogenase, short | 243100 | H95792<br>H96140 | 1108934<br>1109282 | NM_001609 |
| n191 | Activated RNA polymerase II transcription cofactor 4 | 280465 | N51590<br>N50375 | 1191541<br>1192756 | NM_006713 |
| n192 | Unamed | 24855 | R38952 | 796408<br>698810 | |
| n193 | IK cytokine, down-regulator of HLA II | 453230 | AA704849 | 2714767 | NM_006083 |
| n194 | zinc finger protein 254 | 646891 | AA205649 | 1803746<br>1803775 | NM_004876 |
| n195 | Unamed | 549558 | AA129284<br>AA129249 | 1689033<br>1689067 | |
| n196 | Unamed | 1030726 | AA620287 | 2524226 | |
| n197 | Programmed cell death 6-interacting protein | 377245 | AA055248<br>AA055218 | 1547556<br>1547648 | NM_013374 |
| n198 | Hypothetical protein, estradiol-induced | 757462 | AA442301<br>AA437236 | 2142150<br>2154179 | NM_014367 |
| n199 | *Homo sapiens* cDNA FLJ11027 fis, clone PLACE1004114 | 141453 | R68996<br>R68997 | 842513<br>842514 | |
| n200 | Unamed | 172817 | H19803<br>H19804 | 888498<br>888499 | |
| n201 | Unamed | 344073 | W73414<br>W73738 | 1383858<br>1383883 | |
| n202 | Unamed | 42120 | R59618<br>R59678 | 830313<br>830373 | |
| n203 | Unamed | 431733 | AA677803 | 2658325 | |
| n204 | ELL-RELATED RNA POLYMERASE II, ELONGATION FACTOR | 767988 | AA418818<br>AA418943 | 2080619<br>2080744 | NM_012081 |
| n205 | Cadherin 18, type 2 | 1469249 | AA865745 | 2958021 | NM_004934 |

TABLE 1-continued

| Marker | Gene Name | Image Clone ID | Image Clone Accession # | Image Clone GI # | Genebank or RefSeq nuc accession # |
|---|---|---|---|---|---|
| n206 | fragile histidine triad gene | 681948 | AA256122<br>AA256123 | 1891875<br>1891876 | NM_002012 |
| n207 | Complement component 6 | 246246 | N77085<br>N59396 | 1203286<br>1239663 | NM_000065 |
| n208 | Adrenergic, alpha-2A-, receptor | 69935 | T48691<br>T48692 | 650551<br>650552 | NM_000681 |
| n209 | Unamed | 436463 | AA699656 | 2703803 | |
| n210 | mucin 2, intestinal | 1435339 | AA857748 | 2946050 | NM_002457 |
| n211 | Unamed | 214996 | H73239<br>AI820827<br>AI821460 | 5440539<br>1047387 | |
| n212 | KIAA1189 protein | 36462 | R62449<br>R25705 | 781840<br>834328 | |
| n213 | pre-B-cell leukemia transcription factor 3 | 448386 | AA778198 | 2836913 | NM_006195 |
| n214 | Unamed | 361653 | W96347 | 1426262<br>1426263 | |
| n215 | Unamed | 345635 | W72062<br>W76255 | 1382332<br>1386637 | |
| n216 | Unamed | 503520 | AA131325<br>AA131275 | 1692800<br>1693012 | |
| n217 | distal-less homeo box 2 | 1486752 | AA912071 | 3051463 | NM_004405 |
| n218 | Hypothetical protein FLJ21212 | 502625 | AA134576 | 1695573 | NM_024642 |
| n219 | Jumping translocation breakpoint | 1636072 | AI015527 | 3229863 | NM_006694 |
| n220 | CGI-109 protein | 260628 | H97565 | 1118450 | |
| n221 | Unamed | 360357 | AA013354<br>AA013355 | 1474460<br>1474461 | |
| n222 | Unamed | 1622424 | AI016151 | 3230487 | |
| n223 | KIAA1223 protein | 726599 | AA394303<br>AA397920 | 2047298<br>2051261 | |
| n224 | Organic cation transporter | 1456155 | AA862473 | 2954952 | NM_020372 |
| n225 | Adenylyl cyclase-associated protein 2 | 487297 | AA040613<br>AA045508 | 1516909<br>1523744 | NM_006366 |
| n226 | Uncharacterized hypothalamus protein HTMP | 1628069 | AA993905 | 3180450 | NM_018475 |
| n227 | ATPase, Cu++ transporting, beta polypeptide | 266312 | N26536<br>N35647 | 1140884<br>1156789 | NM_000053 |
| n228 | T-box 3 (ulnar mammary syndrome) | 70500 | T48941<br>T48942 | 650801<br>650802 | NM_005996<br>NM_016569 |
| n229 | serine proteinase inhibitor, clade A member 1 | 207735<br>294578 | H58973<br>H58926<br>N71049<br>W01726 | 1011758<br>1011805<br>1227629<br>1273926 | NM_000295 |
| n230 | Inositol 1,4,5-triphosphate receptor, type 1 | 683569<br>471725 | AA215397<br>AA035450<br>AA035477 | 1815142<br>1507136<br>1507248 | NM_002222 |
| n231 | Transforming, acidic coiled-coil containing protein 1 | 193182<br>813188<br>898098 | H47413<br>H47327<br>AA456316<br>AA456713<br>AA598796 | 923379<br>923465<br>2179526<br>2179289<br>2432468 | NM_006283 |
| n232 | Inhibitor of kappa light polypeptide gene enhancer in B-cells, kinase beta | 309563 | N94412 | 1266721 | |
| n233 | CDC2-related protein kinase 7 | 823771<br>858567<br>731231 | AA490255<br>AA490355<br>AA774159<br>AA421065<br>AA420967 | 2219428<br>2219455<br>826048<br>099818<br>099880 | NM_016507 |
| n234 | Hydroxyacid oxidase 2 | 1535106 | AA919149 | 3057172 | NM_016527 |
| n235 | Mannosidase, alpha, class 1A, member 1 | 112629 | T91261 | 714050<br>723174 | NM_005907 |
| n236 | KIAA0523 protein | 50939 | H18630<br>H18715 | 884870<br>884955 | |
| n237 | *Homo sapiens* cDNA FLJ12935 fis, clone NT2RP2004982 | 32962 | R18800<br>R43910 | 772410<br>793661 | |
| n238 | Unamed | 436431 | AA699632 | 2703779 | |
| n239 | RNA binding motif protein 3 | 380797 | AA054287<br>AA054406 | 1545230<br>1545332 | NM_006743 |
| n240 | Unamed | 826109 | AA521327 | 2261870 | |
| n241 | KIAA0367 protein | 813828 | AA447773 | 2161443 | |
| n242 | Unamed | 289534 | N59251 | 1203141<br>1239297 | |
| n243 | Unamed | 1030936 | AA620340 | 2524279 | |
| n244 | Unamed | 1627636 | AI014709 | 3229090 | |
| n245 | Unamed | 363026 | AA018872<br>AA019181 | 1482472<br>1482571 | |

TABLE 1-continued

| Marker | Gene Name | Image Clone ID | Image Clone Accession # | Image Clone GI # | Genebank or RefSeq nuc accession # |
|---|---|---|---|---|---|
| n246 | Hypothetical protein DKFZp434C0328 | 744939 | AA625897 | 2538284 | NM_017577 |
| n247 | Chromosome 11 open reading frame 14 | 726860 | AA293782 | 1941840 | NM_020645 |
|  |  | 279963 | AA398356 | 2051465 |  |
|  |  |  | N57557 | 1201447 |  |
| n248 | Annexin A9 | 239568 | H81304 | 1059393 | NM_003568 |
|  |  |  | H81359 | 1059448 |  |
| n249 | Chromosome 8 open reading frame 2 | 269923 | N36315 | 1139044 | NM_007175 |
|  |  | 432227 | N24894 | 1157457 |  |
|  |  |  | AA679448 | 2659970 |  |
| n250 | Unamed | 205023 | H57374 | 1010206 |  |
|  |  |  | H57423 | 1010255 |  |
| n251 | myosin 5C | 665405 | AA195002 | 1784818 | NM_018728 |
|  |  |  | AA194815 | 1784704 |  |
| n252 | Hypothetical protein FLJ11155 | 288770 | N79400 | 1210328 | NM_018342 |
|  |  |  | N62499 | 1242101 |  |
| n253 | Adipose specific 2 | 740941 | AA478298 | 2206932 | NM_006829 |
| n254 | sorting nexin 9 | 142139 | R69277 | 842680 | NM_016224 |
|  |  |  | R69163 | 842794 |  |
| n255 | Unamed | 731035 | AA421468 | 2100293 |  |
|  |  |  | AA421499 | 2100324 |  |
| n256 | Unamed | 549101 | AA083577 | 1625546 |  |
|  |  |  | AA083485 | 1625637 |  |
| n257 | Cadherin, EGF LAG seven-pass G-type receptor 2, flamingo (*Drosophila*) homolog | 175103 | H39187 | 908686 | NM_001408 |
| n258 | Unamed | 416280 | W86100 | 1398607 |  |
|  |  |  | W86133 | 1398563 |  |
| n259 | Unamed | 32925 | R43646 | 774939 |  |
|  |  |  | R20305 | 821563 |  |
| n260 | Unamed | 298162 | W01408 | 1227371 |  |
|  |  |  | N70791 | 1273407 |  |
| n261 | solute carrier family 16, member 6 | 266389 | N21654 | 1126824 | NM_004694 |
| n262 | Mitogen-activated protein kinase 3 | 809939 | AA454819 | 2177595 |  |
|  |  |  | AA454894 | 2177670 |  |
| n263 | Unamed | 241475 | H90421 | 1080851 |  |
|  |  |  | H90477 | 1080907 |  |
| n264 | KIAA1041 protein | 744388 | AA621197 | 2525136 | NM_014947 |
| n265 | *Homo sapiens* clone TCCCTA00151 mRNA sequence | 767345 | AA418633 | 2080365 |  |
|  |  | 296679 | AA418564 | 2080443 |  |
|  |  |  | N74018 | 1231303 |  |
|  |  |  | W02256 | 1274254 |  |
| n266 | *Homo sapiens* mRNA; cDNA DKFZp761E13121 | 845037 | AA773304 | 2824875 |  |
| n267 | KIAA0712 gene product | 1650304 | AI022613 | 3237854 | NM_014715 |
| n268 | Unamed | 486626 | AA044353 | 1522091 |  |
|  |  |  | AA044031 | 1522209 |  |
| n269 | thyroid hormone receptor-associated protein, 240 kDa subunit | 613070 | AA181646 | 1765080 | NM_005121 |
|  |  | 837892 | AA434084 | 1765113 |  |
|  |  | 490748 | AA434356 | 2138998 |  |
|  |  | 810948 | AA122297 | 2139270 |  |
|  |  | 138477 | AA122265 | 1678504 |  |
|  |  |  | AA459383 | 1678553 |  |
|  |  |  | R68631 | 2184290 |  |
|  |  |  |  | 842147 |  |
|  |  |  |  | 842148 |  |
| n270 | Melanoma antigen recognized by T cells 2 | 359855 | AA010728 | 1471982 | NM_018194 |
|  |  |  | AA011335 | 1472382 |  |
| n271 | Hypothetical protein FLJ13322 | 221890 | H85020 | 1064722 | NM_024722 |
| n272 | Docking protein 1, 62 kD | 504673 | AA150646 | 1712321 | NM_001381 |
|  |  |  | AA142943 | 1722158 |  |
| n273 | inhibin, beta A | 269815 | N40099 | 1141507 | NM_002192 |
|  |  |  | N27159 | 1163644 |  |
| n274 | protein tyrosine phosphatase, receptor type, R | 52079 | H23202 | 891897 | NM_002849 |
|  |  |  | H23315 | 892010 |  |
| n275 | tumor-associated calcium signal transducer 2 | 809938 | AA454810 | 2177586 | NM_002353 |
|  |  |  | AA454884 | 2177660 |  |
| n276 | proline synthetase co-transcribed | 611373 | AA176668 | 1757987 | NM_007198 |
|  |  | 416202 | AA176833 | 1757965 |  |
|  |  | 418094 | W86106 | 1398536 |  |
|  |  |  | W90036 | 1406076 |  |
|  |  |  | W90184 | 1406174 |  |
| n277 | Prohibitin | 276519 | N48458 | 1162308 | NM_002634 |
|  |  | 510464 | N39101 | 1189624 |  |
|  |  |  | AA055656 | 1547995 |  |
|  |  |  | AA055712 | 1548050 |  |

TABLE 1-continued

| Marker | Gene Name | Image Clone ID | Image Clone Accession # | Image Clone GI # | Genebank or RefSeq nuc accession # |
|---|---|---|---|---|---|
| n278 | Unamed | 272879 | N33012 | 1153411 | |
| n279 | Unamed | 1641664 | AI016387 | 3230723 | |
| n280 | Glypican 4 | 358217 | W95635 | 1425544 | NM_001448 |
| | | | W95636 | 1425545 | |
| n281 | Unamed | 1475881 | AA872153 | 2968331 | |
| n282 | keratin 18 | 855521 | AA664179 | 2618170 | NM_000224 |
| n283 | CCR4-NOT transcription complex, subunit 2 | 144042 868590 | R77125 R77126 AA664363 | 851757 851758 2618354 | NM_014515 |
| n284 | Cystatin C | 949938 | AA599177 | 2432802 | NM_000099 |
| n285 | Prohibitin | 42313 | R60946 R61067 | 831641 831762 | NM_002634 |
| n286 | Desmoplakin | 135975 | R33557 R33456 | 789314 789415 | NM_004415 |
| n287 | HSPC041 protein | 549911 | AA082742 AA101072 | 1624800 1647653 | NM_016099 |
| n288 | KIAA0590 gene product | 810773 | AA481751 AA481015 | 2210567 2211303 | NM_014714 |
| n289 | Hypothetical protein MGC11321 | 590298 | AA147837 AA147874 | 1717209 1717264 | NM_032351 |
| n290 | CGI-06 protein | 198960 | H83225 H82992 | 1061662 1061895 | NM_015937 |
| n291 | Hypothetical protein FLJ10466 | 795229 | AA453607 AA454139 | 2167276 2167808 | NM_018100 |
| n292 | Hypothetical protein FLJ14299 | 788087 | AA453170 | 2166839 | NM_025069 |
| n293 | Unamed | 884662 | AA629903 | 2552514 | |
| n294 | nuclear mitotic apparatus protein 1 | 897901 | AA598659 | 2432242 | NM_006185 |
| n295 | zinc finger protein 161 | 666377 | AA232647 | 1855649 | NM_007146 |
| n296 | homeo box B6 | 773296 | AA610066 | 2458494 | NM_018952 |
| n297 | Unamed | 810331 | AA464152 AA464217 | 2189036 2189101 | |
| n298 | CGI-119 protein | 743749 | H78462 H78365 | 1056551 1056454 | NM_016056 |
| n299 | Carbonic anhydrase XII | 594633 | AA171913 AA171613 | 1751034 1750817 | NM_001218 |
| n300 | *Homo sapiens* cDNA FLJ12900 | 212542 | H68663 H68664 | 1030125 1030126 | |
| n301 | Unamed | 1032056 | AA610043 | 2458471 | |
| n302 | *Homo sapiens* cDNA FLJ12900 | 200656 | R98407 | 985119 | |
| n303 | *Homo sapiens* mRNA; cDNA DKFZp564A026 | 950479 | AA599122 | 2432747 | |
| n304 | Hypothetical protein from EUROIMAGE 363668 | 743829 | AA634385 | 2557599 | |
| n305 | ataxia-telangiectasia group D-associated protein | 377275 | AA055485 AA055486 | 1547824 1547825 | NM_012101 |
| n306 | fatty acid desaturase 2 | 878174 | AA775443 | 2834777 | NM_004265 |
| n307 | Moesin | 131362 | R23083 R22977 | 777865 777971 | NM_002444 |
| n308 | Interleukin-1 receptor-associated kinase 1 | 379200 | AA683550 | 2670148 | NM_001569 |
| n309 | Triosephosphate isomerase 1 | 855749 | AA663983 | 2617974 | NM_000365 |
| n310 | KIAA0179 protein | 845602 | AA644334 | 2569552 | |
| n311 | Hypothetical protein FLJ20005 | 51275 | H18864 H18865 | 885104 885105 | NM_017617 |
| n312 | Guanylate binding protein 1 | 841008 | AA486850 AA486849 | 2217013 2217014 | NM_002053 |
| n313 | G protein-coupled receptor, family C, group 5, member B | 321580 | W35153 W32884 | 1314939 1317257 | NM_016235 |
| n314 | Neurocalcin delta | 838478 | AA457611 AA457517 | 2180237 2180331 | NM_032041 |
| n315 | Preferentially expressed antigen in melanoma | 897956 | AA598817 | 2432489 | NM_006115 |
| n316 | ADP-ribosyltransferase 3 | 1468263 | AA884935 | 2994916 | NM_001179 |
| n317 | CCAAT enhancer binding protein, beta | 161993 | H26183 H26184 | 898339 | NM_005194 |
| n318 | Crystallin, alpha B | 839736 | AA504943 AA504891 | 2241051 2241103 | NM_001885 |
| n319 | nudix -type motif 5 | 824421 | AA490236 AA490510 | 2219418 2219683 | NM_014142 |
| n320 | Prominin (mouse)-like 1 | 27544 | R40057 | 822750 | NM_006017 |
| n321 | Unamed | 1031919 | AA609749 | 2458177 | |
| n322 | keratin 17 | 1048993 | AA778645 | 2837976 | NM_000422 |
| n323 | Forkhead box M1 | 564803 | AA129552 AA136566 | 1689317 1697776 | NM_021953 |
| n324 | kangai 1 | 1474284 | AA922309 | 3069618 | NM_002231 |

TABLE 1-continued

| Marker | Gene Name | Image Clone ID | Image Clone Accession # | Image Clone GI # | Genebank or RefSeq nuc accession # |
|---|---|---|---|---|---|
| n325 | Interferon, gamma-inducible protein 16 | 824602 | AA491191 AA490996 | 2220169 2220364 | NM_005531 |
| n326 | Argininosuccinate synthetase | 882522 882461 | AA676466 AA676405 | 2656988 2656927 | NM_000050 |
| n327 | profilin 2 | 486110 | AA040703 AA043167 | 1517193 1521021 | NM_002628 |
| n328 | Unamed | 449112 | AA777488 | 2836967 | |
| n329 | Adenylate kinase 2 | 45464 | H09730 H10488 | 874552 875310 | NM_001625 NM_013411 |
| n330 | Chitinase 3-like 2 | 854338 815214 | AA668821 AA481250 AA481565 | 2630320 2210802 2211117 | NM_004000 |
| n331 | Nuclease sensitive element binding protein 1 | 949932 | AA599175 | 2432800 | NM_004559 |
| n332 | Hypothetical protein FLJ22530 | 745495 | AA625991 | 2538378 | |
| n333 | gamma-aminobutyric acid A receptor, pi | 563598 | AA102670 AA101225 | 1647924 1648004 | NM_014211 |
| n334 | Tryptophanyl-tRNA synthetase | 855786 | AA664040 | 2618031 | NM_004184 |
| n335 | Unamed | 487371 | AA046488 AA046700 | 1524481 1524597 | |
| n336 | Inositol(myo)-1(or 4)-monophosphatase 2 | 32299 | R42685 R17337 | 770947 819630 | NM_014214 |
| n337 | Glutaminase | 624811 | AA188081 AA182001 | 1765502 1774274 | NM_014905 |
| n338 | Spi-B transcription factor | 295093 | W01642 N71628 | 1228340 1273641 | NM_003121 |
| n339 | Lymphocyte antigen 6 complex, locus E | 1470048 | AA865464 | 2957740 | NM_002346 |
| n340 | NGFI-A binding protein 2 | 770868 | AA434487 AA434391 | 2139305 2139401 | NM_005967 |
| n341 | N-myc downstream-regulated gene 2 | 897252 | AA677640 | 2658162 | NM_016250 |
| n342 | Huntingtin-associated protein interacting protein | 971279 | AA682905 | 2668796 | NM_003947 |
| n343 | Unamed | 825207 | AA504379 AA504120 | 2240280 2240539 | |
| n344 | Guanylate binding protein 1, interferon-inducible, 67 kD | 712292 | AA280278 AA280279 | 1921952 1921953 | NM_002053 |
| n345 | early development regulator | 898328 | AA598840 | 2432512 | NM_004427 |
| n346 | type I intermediate filament cytokeratin | 454970 | AA676625 | 2657147 | NM_015515 |
| n347 | PH domain containing protein in retina 1 | 731469 447416 | AA412417 AA702335 | 2071023 2705448 | NM_021200 |
| n348 | Secreted frizzled-related protein 1 | 82225 | T68892 T68966 | 680040 680114 | NM_003012 |
| n349 | DKFZP586K0524 protein | 785744 | AA448941 AA449667 | 2162961 2163417 | |
| n350 | Carbohydrate sulfotransferase 2 | 431301 | AA682637 | 2669918 | NM_004267 |
| n351 | Immunoglobulin heavy constant mu | 214441 | H73590 H73816 | 1046649 1046750 | |
| n352 | Biphenyl hydrolase-like | 877772 | AA626777 | 2539164 | NM_004332 |
| n353 | Complement component 1, s subcomponent | 85634 | T62048 | 665291 665355 | NM_001734 |
| n354 | Phosphoribosyl pyrophosphate synthetase-associated protein 1 | 33949 | R20005 | 774639 824198 | NM_002766 |
| n355 | ATPase, Na+ | 136722 | R35218 R35219 | 792119 792120 | NM_001679 |
| n356 | Unamed | 1626508 | AA995233 | 3181722 | |
| n357 | small inducible cytokine subfamily A, member 19 | 430465 | AA680186 | 2656653 | NM_006274 |
| n358 | 28 kD interferon responsive protein | 268385 | N35187 N23400 | 1137550 1156329 | NM_022147 |
| n359 | Homo sapiens cDNA FLJ20201 | 281597 | N53906 N51612 | 1192778 1195072 | |
| n360 | actin-related protein 3-beta | 726582 | AA394106 AA398135 | 2047094 2051244 | NM_020445 |
| n361 | Tyrosine 3-monooxygenase | 868396 | AA634164 | 2557378 | NM_003405 |
| n362 | lamin B receptor | 489489 | AA099192 AA099136 | 1645023 1645080 | NM_002296 |
| n363 | NADH ubiquinone oxidoreductase MLRQ subunit homolog | 415814 | W84778 W84825 | 1395898 1395955 | NM_020142 |
| n364 | KIAA0173 gene product | 450453 | AA682815 | 2669498 | NM_014640 |
| n365 | tumor necrosis factor (ligand) superfamily, member 13b | 593690 | AA166695 | 1745159 | NM_006573 |
| n366 | Unamed | 969843 | AA663831 | 2617822 | |
| n367 | Unamed | 758309 | AA404269 AA401230 | 2055119 2058993 | |

TABLE 1-continued

| Marker | Gene Name | Image Clone ID | Image Clone Accession # | Image Clone GI # | Genebank or RefSeq nuc accession # |
|---|---|---|---|---|---|
| n368 | Hypothetical protein FLJ20940 | 277173 | N44209<br>N34316 | 1155458<br>1182737 | NM_032192 |
| n369 | Hypothetical protein FLJ10430 | 815556 | AA456821 | 2179541 | NM_018092 |
| n370 | Unamed | 970391 | AA776087 | 2835421 | |
| n371 | nuclear factor I | 416959 | W87528<br>W87611 | 1401583<br>1401675 | NM_005596 |
| n372 | ATP-binding cassette, sub-family B | 813256 | AA456377<br>AA455911 | 2178687<br>2178953 | NM_000927 |
| n373 | natural killer cell transcript 4 | 810859 | AA459180<br>AA458965 | 2183872<br>2184087 | NM_004221 |
| n374 | Unamed | 266135 | N21633 | 1126803<br>1147109 | |
| n375 | Frizzled (*Drosophila*) homolog 8 | 810459 | AA457138 | 2179858 | NM_031866 |
| n376 | high-mobility group protein isoforms I and Y | 782811 | AA448261 | 2161931 | NM_002131 |
| n377 | Ubiquitin specific protease 1 | 489595 | AA099033<br>AA099034 | 1645474<br>1645475 | NM_003368 |
| n378 | Unamed | 786657 | AA451886 | 2165555 | |
| n379 | Complement component 1, r subcomponent | 83549 | T69603<br>T69675 | 680751<br>680823 | NM_001733 |
| n380 | Unamed | 430709 | AA678092 | 2658614 | |
| n381 | Calreticulin | 772913 | AA479920<br>AA428508 | 2112505<br>2204402 | NM_004343 |
| n382 | Cytochrome P450, subfamily I, polypeptide 1 | 782760 | AA448157 | 2161827 | NM_000104 |
| n383 | Peptidylprolyl isomerase B | 756600 | AA481464<br>AA481699 | 2211016<br>2211251 | NM_000942 |
| n384 | Angiopoietin-like 4 | 69002 | T53705<br>T54298 | 655566<br>656159 | NM_016109 |
| n385 | Proteasome subunit, beta type, 9 | 1456118 | AA862434 | 2954913 | NM_002800 |
| n386 | Unamed | 285207 | N66273 | 1218398 | |
| n387 | ataxin-1 ubiquitin-like interacting protein | 767180 | AA424661<br>AA424564 | 2103534<br>2103614 | NM_020131 |
| n388 | Integral membrane protein 2A | 245277 | N72450<br>N53447 | 1194613<br>1229554 | NM_004867 |
| n389 | FYN-binding protein | 293325 | N64862<br>N92106 | 1212691<br>1264415 | NM_001465 |
| n390 | Ribosomal protein L44 | 51078 | H17242<br>H17135 | 883375<br>883482 | NM_021029 |
| n391 | Unamed | 399577 | AA733090 | 2754449 | |
| n392 | fibulin 5 | 50483 | H17615<br>H17726 | 883855<br>883966 | NM_006329 |
| n393 | Phosphodiesterase 7A | 1671124<br>68340 | AI075273<br>T56982<br>T56983 | 3401864<br>658843<br>658844 | |
| n394 | Unamed | 1626808 | AI018277 | 3232796 | |
| n395 | small inducible cytokine subfamily B (Cys-X-Cys), member 10 | 1493160 | AA878880 | 2987845 | NM_001565 |
| n396 | CDC20 | 898062 | AA598776 | 2432448 | NM_001255 |
| n397 | Unamed | 1048601 | AA608870 | 2457298 | |
| n398 | Potassium intermediate | 756708 | AA443903 | 2156578 | NM_002250 |
| n399 | keratin 6B | 366481 | AA026495<br>AA026418 | 1492319<br>1492377 | NM_005555 |
| n400 | Aldehyde dehydrogenase 1 family, member A3 | 814798 | AA455235<br>AA465614 | 2178011<br>2191781 | NM_000693 |
| n401 | Homolog of mouse quaking QKI | 843385 | AA489386<br>AA489445 | 2218988<br>2219047 | |
| n402 | Suppression of tumorigenicity 14 | 825085 | AA489246 | 2218848<br>2240477 | NM_021978 |
| n403 | Coatomer protein complex, subunit beta 2 | 278687 | W01400<br>N62924 | 1210753<br>1273380 | NM_004766 |
| n404 | Decidual protein induced by progesterone | 137554<br>245774<br>135811 | R39563<br>R39621<br>N55269<br>N76878<br>R33362<br>R33363 | 797076<br>797077<br>1198148<br>1239456<br>789220<br>789221 | NM_007021 |
| n405 | BTG family, member 3 | 246304 | N52496<br>N74741 | 1193662<br>1232026 | NM_006806 |
| n406 | KIAA1866 protein | 754126 | AA478623<br>AA478880 | 2207257<br>2207514 | |
| n407 | Hypothetical protein MGC10986 | 344937 | W75960<br>W72885 | 1383020<br>1386334 | NM_030576 |
| n408 | Tetranectin | 345553 | W76174<br>W73889 | 1382284<br>1386418 | NM_003278 |

TABLE 1-continued

| Marker | Gene Name | Image Clone ID | Image Clone Accession # | Image Clone GI # | Genebank or RefSeq nuc accession # |
|---|---|---|---|---|---|
| n409 | Unamed | 1639103 | AI016824 | 3231160 | |
| n410 | T cell receptor beta locus | 306841 | N91921 | 1264230 | |
| n411 | Hypothetical protein FLJ12770 | 813815 | AA447727 | 2161397 | NM_032174 |
|  |  |  | AA447889 | 2161559 |  |
| n412 | Hypothetical protein FLJ21841 | 347268 | W80898 | 1391809 | NM_024609 |
|  |  | 1470278 | W80791 | 1391922 |  |
|  |  |  | AA866029 | 2958305 |  |
| n413 | keratin 5 | 592540 | AA160595 | 1735874 | NM_000424 |
|  |  |  | AA160507 | 1735963 |  |
| n414 | Potassium channel modulatory factor | 752813 | AA436378 | 2141292 | NM_020122 |
|  |  |  | AA481311 | 2210863 |  |
| n415 | pellino (*Drosophila*) homolog 1 | 416676 | W86504 | 1400251 | NM_020651 |
| n416 | T cell receptor alpha locus | 770014 | AA427667 | 2111387 |  |
|  |  |  | AA427491 | 2111484 |  |
| n417 | CD48 antigen | 125134 | R05415 | 756035 | NM_001778 |
|  |  |  |  | 756036 |  |
| n418 | Unamed | 345416 | W76022 | 1382143 |  |
|  |  |  | W72466 | 1386266 |  |
| n419 | Interleukin enhancer binding factor 2, 45 kD | 242952 | H95712 | 1108780 | NM_004515 |
|  |  |  | H95638 | 1108854 |  |
| n420 | cDNA for differentially expressed CO16 gene | 782575 | AA447522 | 2161192 |  |
|  |  |  | AA448505 | 2162175 |  |
| n421 | Thymopoietin | 454083 | AA676998 | 2657520 | NM_003276 |
| n422 | DKFZP564D0764 protein | 796767 | AA460732 | 2185852 |  |
|  |  |  | AA460904 | 2186024 |  |
| n423 | MAD2 (mitotic arrest deficient, yeast, homolog)-like 1 | 814701 | AA481076 | 2210628 | NM_002358 |
| n424 | AD037 protein | 1572070 | AA933056 | 3086989 | NM_032023 |
| n425 | *Homo sapiens* mRNA; cDNA DKFZp434B0425 | 430186 | AA010188 | 1471215 |  |
| n426 | DEK oncogene | 133136 | R28400 | 781512 | NM_003472 |
|  |  |  | R25377 | 784535 |  |
| n427 | c-Cbl-interacting protein | 1604005 | AA989257 | 3173879 | NM_031892 |
| n428 | uridine monophosphate kinase | 344243 | W69906 | 1379374 | NM_012474 |
|  |  |  | W70171 | 1379432 |  |
| n429 | Progesterone receptor membrane component 1 | 41698 | R59281 | 829916 | NM_006667 |
|  |  |  | R59221 | 829976 |  |
| n430 | Diubiquitin | 243741 | N49629 | 1154320 | NM_006398 |
|  |  |  | N33920 | 1190795 |  |
| n431 | Transcription factor 19 | 416075 | W85878 | 1398307 | NM_007109 |
|  |  |  | W85962 | 1398390 |  |
| n432 | KIAA1089 protein | 770709 | AA476305 | 2138741 |  |
|  |  |  | AA433827 | 2204516 |  |
| n433 | D123 gene product | 784830 | AA448289 | 2161959 | NM_006023 |
| n434 | Macrophage receptor with collagenous structure | 840466 | AA485867 | 2215086 | NM_006770 |
|  |  |  | AA487769 | 2215200 |  |
| n435 | Hypothetical protein FLJ20624 | 784016 | AA443698 | 2115617 | NM_017906 |
|  |  |  |  | 2156373 |  |
| n436 | matrix metalloproteinase 7 | 470393 | AA031514 | 1501467 | NM_002423 |
|  |  |  | AA031513 | 1501468 |  |
| n437 | scrapie responsive protein 1 | 796148 | AA460975 | 2186095 | NM_007281 |
| n438 | Carboxypeptidase, vitellogenic-like | 39833 | R53455 | 815357 | NM_031311 |
| n439 | Integral membrane protein 3 | 471196 | AA034213 | 1506023 | NM_030926 |
| n440 | Sialyltransferase 1 | 897906 | AA598652 | 2432235 | NM_003032 |
| n441 | Ectonucleotide pyrophosphatase | 430968 | AA678335 | 2658857 | NM_005021 |
| n442 | Interleukin 16 | 809776 | AA454784 | 2177508 | NM_004513 |
|  |  |  | AA454732 | 2177560 |  |
| n443 | Unamed | 80186 | T64192 | 668057 |  |
|  |  |  | T64380 | 668245 |  |
| n444 | CD3D antigen | 377560 | AA055945 | 1548284 | NM_000732 |
|  |  |  | AA055946 | 1548285 |  |
| n445 | major histocompatibility complex, class II, DR alpha | 153411 | R48091 | 810005 | NM_019111 |
|  |  |  | R47979 | 810117 |  |
| n446 | Lymphotoxin beta | 1946534 | AI351740 | 4088946 | NM_002341 |
|  |  |  |  |  | NM_009588 |
| n447 | KIAA0535 gene product | 1910316 | AI350226 | 4087432 | NM_014682 |
| n448 | TATA box binding protein | 280735 | N50603 | 1191715 | NM_003194 |
|  |  |  | N50549 | 1191769 |  |
| n449 | Hypothetical protein MGC5363 | 502910 | AA128571 | 1688423 | NM_024064 |
|  |  |  | AA128274 | 1688524 |  |
| n450 | Wingless-type MMTV integration site family, member 6 | 687972 | AA236986 | 1860367 |  |
|  |  |  | AA235928 | 1861014 |  |
| n451 | Mitogen-activated protein kinase kinase 6 | 45578 | H07920 | 872742 | NM_002758 |
|  |  |  | H08016 | 872838 | NM_031988 |

TABLE 1-continued

| Marker | Gene Name | Image Clone ID | Image Clone Accession # | Image Clone GI # | Genebank or RefSeq nuc accession # |
|---|---|---|---|---|---|
| n452 | Microfibrillar-associated protein 2 | 291880 | W03413 | 1219612 | NM_002403 |
|  |  |  | N67487 | 1275326 | NM_017459 |
| n453 | Unamed | 503051 | AA151535 | 1719966 |  |
|  |  |  | AA149250 | 1720022 |  |
| n454 | Adipose differentiation-related protein | 435036 | AA700054 | 2703017 | NM_001122 |
| n455 | Unamed | 825654 | AA505050 | 2241210 |  |
|  |  |  |  | 2241211 |  |
| n456 | Chitinase 3-like 1 | 770212 | AA434048 | 2138962 | NM_001276 |
|  |  |  | AA434115 | 2139029 |  |
| n457 | fatty-acid-Coenzyme A ligase, long-chain 2 | 2014138 | AI361530 | 4113151 | NM_021122 |
|  |  | 82734 | T73651 | 690231 |  |
|  |  |  | T73556 | 690326 |  |
| n458 | tumor necrosis factor receptor superfamily, member 7 | 34637 | R45026 | 779904 | NM_001242 |
|  |  |  |  | 823385 |  |
| n459 | Unamed | 399421 | AA733177 | 2754536 |  |
| n460 | zinc finger protein, subfamily 1A, 1 | 447171 | AA702985 | 2706098 | NM_006060 |
| n461 | Ceruloplasmin | 223350 | H86642 | 1068133 | NM_000096 |
|  |  |  | H86554 | 1068221 |  |
| n462 | Transcription factor-like 1 | 757165 | AA444129 | 2156625 | NM_005997 |
|  |  |  | AA443950 | 2156804 |  |
| n463 | CD37 antigen | 824384 | AA489700 | 2219302 | NM_001774 |
| n464 | RNA helicase | 511633 | AA126958 | 1686410 | NM_014314 |
|  |  |  | AA127167 | 1686512 |  |
| n465 | Thrombopoietin | 754034 | AA480029 | 2207614 | NM_000460 |
|  |  |  | AA479058 | 2208180 |  |
| n466 | Unamed | 342740 | W68630 | 1377498 |  |
|  |  |  | W68629 | 1377499 |  |
| n467 | RNA binding motif protein, X chromosome | 133236 | R26929 | 782841 | NM_002139 |
|  |  |  | R26706 | 783064 |  |
| n468 | ets variant gene 6 | 1590021 | AA983191 | 3161716 | NM_001987 |
| n469 | CD79B antigen | 155717 | R72079 | 846111 | NM_000626 |
|  |  |  | R72128 | 846160 | NM_021602 |
| n470 | Chromosome 1 open reading frame 2 | 47665 | H11464 | 876284 | NM_006589 |
|  |  |  | H11572 | 876392 |  |
| n471 | Trinucleotide repeat containing 3 | 199367 | R95691 | 981351 | NM_005878 |
| n472 | Melanoma antigen, family A, 3 | 1631546 | AA995045 | 3181534 | NM_005362 |
| n473 | Retinoic acid receptor responder 1 | 2028617 | AI261360 | 3869563 | NM_002888 |
|  |  | 309583 | W30772 | 1266733 |  |
|  |  |  | N94424 | 1311763 |  |
| n474 | Hypothetical protein DKFZp762N0610 | 1635186 | AI005042 | 3214552 |  |
|  |  | 202919 | H54093 | 994240 |  |
|  |  |  | H54094 | 994241 |  |
| n475 | Isopentenyl-diphosphate delta isomerase | 267176 | N31862 | 1138111 | NM_004508 |
|  |  |  | N23961 | 1152261 |  |
| n476 | 3-hydroxy-3-methylglutaryl-Coenzyme A synthase 2 | 757222 | AA496148 | 2229469 | NM_005518 |
|  |  |  | AA496149 | 2229470 |  |
| n477 | Lipopolysaccharide-binding protein | 66437 | R16098 | 767979 | NM_004139 |
|  |  |  | R15731 | 767907 |  |
| n478 | jun D proto-oncogene | 491403 | AA156585 | 1721929 | NM_005354 |
|  |  |  | AA150416 | 1728227 |  |
| n479 | Src-like-adapter | 815774 | AA485141 | 2214360 | NM_006748 |
| n480 | Sjogren syndrome antigen A1 | 282956 | N45131 | 1186297 | NM_003141 |
| n481 | Hypothetical protein FLJ23563 | 306066 | N91003 | 1444330 |  |
|  |  |  | W20132 | 1296002 |  |
| n482 | Alkaline phosphatase, liver, bone kidney | 1475595 | AA873885 | 2968021 | NM_000478 |
| n483 | GS1999full | 161484 | H25560 | 894683 | NM_032564 |
|  |  |  | H25606 | 894729 |  |
| n484 | kinesin family member C3 | 753038 | AA436460 | 2141374 | NM_005550 |
|  |  |  | AA436508 | 2141422 |  |
| n485 | Protoporphyrinogen oxidase | 504452 | AA151249 | 1719439 | NM_000309 |
|  |  |  | AA151248 | 1719440 |  |
| n486 | fatty acid binding protein 5 | 2012523 | AI359037 | 4110658 | NM_001444 |
|  |  | 281039 | N47717 | 1188882 |  |
|  |  |  |  | 1188883 |  |
| n487 | HSPC182 protein | 450213 | AA703536 | 2713454 | NM_014188 |
| n488 | NCK adaptor protein 1 | 712683 | AA280214 | 1921815 | NM_006153 |
|  |  | 302369 | AA280548 | 1924658 |  |
|  |  |  | W16804 | 1443464 |  |
|  |  |  | N90137 | 1291201 |  |
| n489 | Hypothetical protein FLJ12389 similar to acetoacetyl-CoA synthetase | 153830 | R48370 | 810296 | NM_023928 |
|  |  |  | R48270 | 810396 |  |

TABLE 1-continued

| Marker | Gene Name | Image Clone ID | Image Clone Accession # | Image Clone GI # | Genebank or RefSeq nuc accession # |
|---|---|---|---|---|---|
| n490 | Guanylate cyclase 1, soluble, alpha 3 | 51011 | H19241 | 885481 | NM_000856 |
| | | 51749 | H19242 | 885482 | |
| | | | H23049 | 891744 | |
| | | | H24329 | 893024 | |
| n491 | CD19 antigen | 2027587 | AI356451 | 4108072 | NM_001770 |
| n492 | Ubiquitin specific protease 21 | 183062 | H42874 | 918926 | NM_016572 |
| | | | H42938 | 918990 | NM_012475 |
| n493 | small inducible cytokine subfamily D (Cys-X3-Cys), member 1 | 140574 | R66139 | 838777 | NM_002996 |
| | | 161923 | R67753 | 840391 | |
| | | | H26022 | 895145 | |
| | | | H26069 | 895192 | |
| n494 | linker for activation of T cells | 346360 | W74254 | 1384502 | NM_014387 |
| | | | | 1390481 | |
| n495 | CDK2-associated protein 1 | 144932 | R78607 | 854888 | NM_004642 |
| | | | R78608 | 854889 | |
| n496 | Unamed | 767164 | AA424653 | 2103526 | |
| | | | AA424556 | 2103606 | |
| n497 | claudin 1 | 664975 | AA194833 | 1784523 | NM_021101 |
| n498 | proline arginine-rich end leucine-rich repeat protein | 837870 | AA434067 | 2138981 | NM_002725 |
| | | | AA434342 | 2139256 | |
| n499 | Membrane metallo-endopeptidase | 200814 | R98851 | 985452 | NM_000902 |
| | | | R98936 | 985537 | NM_007287 |
| | | | | | NM_007288 |
| | | | | | NM_007289 |
| n500 | Methylcrotonoyl-Coenzyme A carboxylase 1 | 490649 | AA101777 | 1648774 | NM_020166 |
| | | | AA101775 | 1648775 | |
| n501 | TATA-binding protein-binding protein | 814562 | AA480876 | 2210428 | NM_013375 |
| | | | AA480934 | 2210486 | |
| n502 | Unamed | 753019 | AA436575 | 2141462 | |
| | | | AA436548 | 2141489 | |
| n503 | Unamed | 729924 | AA399633 | 2052647 | |
| n504 | Amyloid beta (A4) precursor protein (protease nexin-II, Alzheimer disease) | 856575 | AA633658 | 2556872 | NM_000484 |
| n505 | Apoptosis regulator BCL-G | 1049216 | AA620708 | 2524647 | NM_030766 |
| n506 | Kallikrein 6 | 809784 | AA454794 | 2177519 | NM_002774 |
| | | | AA454743 | 2177570 | |
| n507 | tumor necrosis factor, alpha-induced protein 6 | 357031 | W92764 | 1422204 | NM_007115 |
| | | | W93163 | 1422316 | |
| n508 | BUB3 | 785778 | AA448967 | 2162987 | NM_004725 |
| | | | AA449693 | 2163443 | |
| n509 | Unamed | 512605 | AA062659 | 1556882 | |
| n510 | Transcriptional co-activator with PDZ-binding motif (TAZ) | 589869 | AA148213 | 1717719 | NM_015472 |
| n511 | ! unamed | 156962 | R74321 | 848691 | |
| | | | R74415 | 848785 | |
| n512 | *Homo sapiens* mRNA; cDNA DKFZp564H1916 | 813265 | AA455935 | 2178711 | |
| | | | AA456404 | 2178980 | |
| n513 | CD22 antigen | 284220 | N53534 | 1194700 | NM_001771 |
| n514 | Hypothetical protein PRO0823 | 1486194 | AA936866 | 3094900 | |
| n515 | Unamed | 824986 | AA489171 | 2218692 | |
| | | | | 2218773 | |
| n516 | Unamed | 648025 | AA206915 | 1802607 | |
| | | | AA204757 | 1802492 | |
| n517 | signal transducer and activator of transcription 1, 91 kD | 840691 | AA488075 | 2215173 | NM_007315 |
| | | | AA486367 | 2215506 | |
| n518 | Hypothetical protein DKFZp566J091 | 854678 | AA630084 | 2552695 | NM_030915 |
| n519 | Proteasome 26S subunit, non-ATPase, 3 | 815861 | AA485051 | 2214270 | NM_002809 |
| | | | | 2214271 | |
| n520 | UDP-Gal betaGlcNAc beta 1,4-galactosyltransferase, polypeptide 5 | 825641 | AA504652 | 2240812 | NM_004776 |
| | | | AA504750 | 2240910 | |
| n521 | Unamed | 1500438 | AI733090 | 5054203 | |
| | | | AA887255 | 5339299 | |
| n522 | zinc finger protein 313 | 25071 | R38967 | 796423 | NM_018683 |
| | | 825697 | T80323 | 698832 | |
| | | | AA504825 | 2240985 | |
| n523 | Unamed | 1626765 | AI018248 | 3232767 | |
| n524 | beta-1,3-glucuronyltransferase 1 | 290030 | N64656 | 1212485 | NM_018644 |
| | | | N80090 | 1242791 | |
| n525 | Complement component (3d | 826984 | AA521362 | 2261905 | NM_001877 |
| n526 | Hypothetical protein PP591 | 745606 | AA626336 | 2538723 | NM_025207 |
| | | 23759 | T77100 | 795627 | |
| | | | R38171 | 694303 | |
| n527 | SELENOPHOSPHATE SYNTHETASE | 840702 | AA486372 | 2215178 | NM_012247 |
| | | | AA488081 | 2215512 | |

TABLE 1-continued

| Marker | Gene Name | Image Clone ID | Image Clone Accession # | Image Clone GI # | Genebank or RefSeq nuc accession # |
|---|---|---|---|---|---|
| n528 | DKFZP434F2021 protein | 773430 | AA426041 | 2106529 | |
| | | | AA428076 | 2111769 | |
| n529 | Isopentenyl-diphosphate delta isomerase | 44975 | H08820 | 873642 | NM_004508 |
| | | | H08899 | 873721 | |
| n530 | RBP1-like protein | 782618 | AA447551 | 2161221 | NM_031371 |
| | | | | 2162203 | |
| n531 | elastin | 810934 | AA459539 | 2184215 | NM_000501 |
| | | | AA459308 | 2184446 | |
| n532 | cyclin F | 455128 | AA676797 | 2657319 | NM_001761 |
| n533 | fatty acid binding protein 7, brain | 279195 | N46862 | 1188028 | NM_001446 |
| | | 345626 | N47182 | 1188348 | |
| | | | W76403 | 1382321 | |
| | | | W72051 | 1386627 | |
| n534 | Unamed | 246329 | N52506 | 1193672 | |
| | | | N74750 | 1232035 | |
| n535 | Hypothetical protein FLJ11181 | 139957 | R64048 | 835827 | NM_018350 |
| | | | R63948 | 835927 | |
| n536 | Anaphase promoting complex subunit 5 | 823954 | AA491011 | 2220016 | NM_016237 |
| | | | | 2220184 | |
| n537 | Neurexin 1 | 32573 | R43532 | 775047 | NM_004801 |
| | | | R20413 | 821461 | |
| n538 | Hypothetical protein PRO2521 | 244062 | N45441 | 1162017 | NM_018530 |
| | | | N38810 | 1186607 | |
| n539 | Ubiquitin-conjugating enzyme E2L 3 | 853988 | AA669526 | 2631025 | NM_003347 |
| n540 | Wnt inhibitory factor-1 | 1504628 | AA897696 | 3034310 | NM_007191 |
| n541 | Farnesyl-diphosphate farnesyltransferase 1 | 866882 | AA679352 | 2659874 | NM_004462 |
| n542 | Homo sapiens clone IMAGE 38177 | 47036 | H10956 | 875776 | |
| | | | H10957 | 875777 | |
| n543 | Melanoma antigen, family A, 4 | 1475476 | AA857809 | 2946111 | NM_002362 |
| n544 | PP3111 protein | 950409 | AA599073 | 2432698 | NM_022156 |
| n545 | Ubiquitin-conjugating enzyme E2L 6 | 725395 | AA292074 | 1940152 | NM_004223 |
| | | | AA292031 | 1940060 | |
| n546 | KIAA0740 gene product | 624379 | AA187789 | 1766505 | |
| | | | AA182796 | 1773983 | |
| n547 | nogo receptor | 770989 | AA428418 | 2112171 | NM_023004 |
| | | | AA427404 | 2112232 | |
| n548 | Hypothetical protein FLJ22693 | 205497 | H59985 | 1010689 | NM_022750 |
| | | | | 1012817 | |
| n549 | H4 histone family, member H | 447715 | AA702781 | 2705894 | NM_003543 |
| n550 | Unamed | 1031917 | AA609748 | 2458176 | |
| n551 | Phosphatidylinositol 4-kinase, catalytic, beta polypeptide | 782692 | AA447595 | 2161265 | NM_002651 |
| | | | AA448094 | 2161764 | |
| n552 | Hypothetical protein DKFZp762A227 | 725152 | AA404709 | 2059052 | |
| | | | AA404310 | 2058912 | |
| n553 | Hypothetical protein FLJ22757 | 826242 | AA521476 | 2262019 | NM_024898 |
| n554 | Hypothetical protein MGC16291 | 324593 | W46954 | 1331662 | NM_032770 |
| | | | W46955 | 1331663 | |
| n555 | sterol regulatory element binding transcription factor 2 | 435551 | AA701914 | 2705027 | NM_004599 |
| n556 | S100 calcium-binding protein A1 | 756931 | AA428803 | 2107722 | NM_006271 |
| | | | | 2110354 | |
| n557 | UDP-N-acetyl-alpha-D-galactosamine-galactosylglucosylceramide N-acetylgalactosaminyltransferase | 125092 | R05278 | 755898 | NM_001478 |
| | | | R05336 | 755956 | |
| n558 | dopa decarboxylase | 384015 | AA702640 | 2705753 | NM_000790 |
| n559 | Interleukin 8 | 549933 | AA102526 | 1624805 | NM_000584 |
| | | | AA082747 | 1647657 | |
| n560 | Ankyrin 1, erythrocytic | 810625 | AA464755 | 2188933 | NM_000037 |
| | | | AA464049 | 2189639 | NM_020475 |
| | | | | | NM_020476 |
| | | | | | NM_020477 |
| | | | | | NM_020478 |
| | | | | | NM_020479 |
| | | | | | NM_020480 |
| | | | | | NM_020481 |
| n561 | Kallikrein 5 | 344588 | W73168 | 1383275 | NM_012427 |
| | | | W73140 | 1383322 | |
| n562 | Glutamate receptor, ionotropic, N-methyl D-aspartate 2C | 179163 | H50114 | 989955 | NM_000835 |
| | | | H50161 | 990002 | |
| n563 | Unamed | 731025 | AA421267 | 2100092 | |
| | | | AA421314 | 2100190 | |
| n564 | Cadherin, EGF LAG seven-pass G-type receptor 3, flamingo (Drosophila) homolog | 754653 | AA411204 | 2068754 | NM_001407 |

TABLE 1-continued

| Marker | Gene Name | Image Clone ID | Image Clone Accession # | Image Clone GI # | Genebank or RefSeq nuc accession # |
|---|---|---|---|---|---|
| n565 | Unamed | 470148 | AA029867 | 1496718 | |
| | | | AA029314 | 1496094 | |
| n566 | *Homo sapiens* cDNA FLJ21600 fis, clone COL07202 | 277545 | N47366 | 1188532 | |
| | | | N56982 | 1200872 | |
| n567 | Unamed | 159725 | H23963 | 892658 | |
| n568 | Thioredoxin peroxidase | 795543 | AA459663 | 2184570 | NM_006406 |
| n569 | Kynureninase | 1456405 | AA862985 | 2955464 | NM_003937 |
| | | 252515 | AI791358 | 5339074 | |
| | | | AI732962 | 1069050 | |
| | | | H87471 | 1069162 | |
| | | | H87583 | | |
| n570 | Secretagogin | 845521 | AA644563 | 2569781 | NM_006998 |
| n571 | Unamed | 183281 | H43974 | 920026 | |
| | | | H43975 | 920027 | |
| n572 | Unamed | 594585 | AA169633 | 1748263 | |
| | | | AA171675 | 1750742 | |
| n573 | Kallikrein 1.0 | 809616 | AA458489 | 2183396 | NM_002776 |
| | | 810960 | AA459401 | 2184308 | |
| | | | AA459626 | 2184533 | |
| n574 | Unamed | 1541820 | AA928128 | 3077284 | |
| n575 | Unamed | 898133 | AA598500 | 2432083 | |
| n576 | Apolipoprotein D | 159608 | H15842 | 880662 | NM_001647 |
| | | 838611 | H16152 | 880972 | |
| | | | AA457084 | 2179695 | |
| | | | AA456975 | 2179804 | |
| n577 | Ornithine decarboxylase 1 | 796646 | AA460115 | 2185500 | NM_002539 |
| | | | AA461467 | 2185331 | |
| n578 | Unamed | 199585 | R96499 | 982159 | |
| | | | | 982204 | |
| n579 | *Homo sapiens* clone 25012 | 306933 | N79081 | 1241782 | |
| n580 | *Homo sapiens* clone MGC 9740 IMAGE 3853707 | 129128 | R10885 | 763620 | |
| | | | R10935 | 763670 | |
| n581 | Unamed | 417393 | W89059 | 1403848 | |
| | | | | 1403945 | |
| n582 | protein phosphatase 2, regulatory subunit B, beta isoform | 586725 | AA129170 | 1688954 | NM_006244 |
| | | | AA129171 | 1688955 | |
| n583 | Mitogen-activated protein kinase kinase 1 interacting protein 1 | 305325 | W19601 | 1267236 | NM_021970 |
| | | | N94746 | 1295519 | |
| n584 | Unamed | 1639660 | AI024950 | 3240563 | |
| n585 | Unamed | 175302 | H40290 | 916342 | |
| n586 | protein kinase, X-linked | 1032170 | AA778448 | 2837779 | NM_005044 |
| | | 1638550 | AI016760 | 3231096 | |
| | | 1869486 | AI264246 | 3872449 | |
| n587 | Hydroxyprostaglandin dehydrogenase 15-(NAD) | 868838 | AA775223 | 2834557 | NM_000860 |
| n588 | Forkhead box C1 | 253733 | N75774 | 1128686 | NM_001453 |
| | | 358885 | N22552 | 1238352 | |
| | | | W94714 | 1423751 | |
| | | | W94629 | 1423854 | |
| n589 | *Homo sapiens* clone 24468 | 48330 | H14948 | 879768 | |
| | | | H14949 | 879769 | |
| n590 | CD69 antigen | 704459 | AA279755 | 1921238 | NM_001781 |
| | | | AA279883 | 1921348 | |
| n591 | Amyloid beta (A4) precursor protein-binding, family A, member 1 (X11) | 172751 | H19686 | 888381 | NM_001163 |
| | | | H19687 | 888382 | |
| n592 | similar to rat nuclear ubiquitous casein kinase 2 | 591095 | AA158345 | 1733156 | NM_022731 |
| | | | AA158346 | 1733157 | |
| n593 | Unamed | 1049168 | AA620669 | 2524608 | |
| n594 | MDS024 protein | 787893 | AA452404 | 2165840 | NM_021820 |
| | | | AA452171 | 2166073 | |
| n595 | DKFZP434O125 protein | 240208 | H79705 | 1057794 | |
| | | | H79706 | 1057795 | |
| n596 | DKFZP566D193 protein | 782383 | AA431812 | 2115115 | |
| | | | AA431407 | 2115520 | |
| n597 | src homology three and cysteine rich domain | 470379 | AA031398 | 1501239 | NM_003149 |
| | | | AA031284 | 1501359 | |
| n598 | CDC-like kinase 3 | 854645 | AA630459 | 2553070 | NM_003992 |
| | | | | | NM_001292 |
| n599 | Annexin A8 | 461307 | AA699870 | 2702833 | NM_001630 |
| n600 | Proteasome 26S subunit, non-ATPase, 2 | 809992 | AA455193 | 2177628 | NM_002808 |
| | | | AA454852 | 2177969 | |
| n601 | Unamed | 796519 | AA460254 | 2185070 | |
| | | | | 2188702 | |
| n602 | Desmoplakin | 512751 | AA062688 | 1557065 | NM_004415 |
| n603 | kraken-like | 35575 | R45964 | 823208 | NM_014509 |

TABLE 1-continued

| Marker | Gene Name | Image Clone ID | Image Clone Accession # | Image Clone GI # | Genebank or RefSeq nuc accession # |
|---|---|---|---|---|---|
| n604 | SAM domain and HD domain, 1 | 739094 | AA421603 | 2100601 | NM_015474 |
| n605 | F-box only protein 2 | 179269 | H50245 | 990086 | NM_012168 |
|  |  |  | H50284 | 990125 |  |
| n606 | Unamed | 306726 | W23921 | 1264177 |  |
|  |  |  | N91868 | 1300804 |  |
| n607 | Unamed | 243347 | N38960 | 1162167 |  |
|  |  |  |  | 1189272 |  |
| n608 | Nucleolar protein 1 | 280970 | N50854 | 1192020 | NM_006170 |
| n609 | Coronin, actin-binding protein, 1A | 487988 | AA047478 | 1525652 | NM_007074 |
|  |  |  | AA047477 | 1525653 |  |
| n610 | Unamed | 147987 | R82024 | 858627 |  |
|  |  |  | R82071 | 858674 |  |
| n611 | Human clone 23564 mRNA sequence | 305481 | N89812 | 1443139 |  |
| n612 | uveal autoantigen with coiled-coil domains and ankyrin repeats | 71312 | T47624 | 649604 |  |
|  |  |  | T47625 | 649605 |  |
| n613 | Interleukin 7 receptor | 840460 | AA487767 | 2215084 | NM_002185 |
|  |  | 841238 | AA485865 | 2215198 |  |
| n614 | Succinate dehydrogenase complex, subunit A, flavoprotein | 80915 | T70043 | 681191 | NM_004168 |
|  |  |  | T70109 | 681257 |  |
| n615 | KIAA0293 protein | 32697 | R43605 | 821525 |  |
| n616 | Hypothetical protein MGC5350 | 1637791 | AI002036 | 3202073 | NM_030920 |
|  |  | 856388 | AA774678 | 2834012 |  |
|  |  | 587992 | AA130595 | 1692017 |  |
|  |  |  | AA130596 | 1692018 |  |
| n617 | Neuropilin 1 | 489535 | AA098867 | 1645051 | NM_003873 |
|  |  |  | AA099262 | 1645108 |  |
| n618 | growth factor receptor-bound protein 7 | 236059 | H53702 | 993849 | NM_005310 |
|  |  |  | H53703 | 993850 |  |
| n619 | Synaptic vesicle protein 2B homolog | 39933 | R53963 | 815263 | NM_014848 |
|  |  |  | R53361 | 815865 |  |
| n620 | Hypothetical protein FLJ13154 | 1536236 | AA923560 | 3070869 | NM_024598 |
| n621 | Vascular cell adhesion molecule 1 | 44477 | H07072 | 870603 | NM_001078 |
|  |  | 49164 | H07071 | 870604 |  |
|  |  |  | H16591 | 882816 |  |
|  |  |  | H16637 | 882877 |  |
| n622 | Hypothetical protein FLJ21324 | 781442 | AA428603 | 2112796 | NM_021941 |
|  |  | 192593 | AA432306 | 2114689 |  |
|  |  | 25360 | H41496 | 917548 |  |
|  |  |  | R15074 | 764876 |  |
|  |  |  | R12141 | 769347 |  |
| n623 | PBX | 121406 | T96688 | 735312 | NM_004571 |
|  |  |  | T96804 | 735428 |  |
| n624 | v-kit Hardy-Zuckerman 4 feline sarcoma viral oncogene homolog | 265060 | N20798 | 1125979 | NM_000222 |
|  |  |  |  | 1149037 |  |
| n625 | B-cell CLL | 46452 | H09835 | 874570 | NM_022898 |
|  |  |  | H09748 | 874657 |  |
| n626 | H2A histone family, member O | 488964 | AA057146 | 1525296 | NM_003516 |
|  |  |  | AA047260 | 1549730 |  |
| n627 | *Homo sapiens*, Similar to KIAA0626 gene product, clone MGC 5129 IMAGE 3458716 | 124320 | R02095 | 751831 |  |
|  |  |  | R02208 | 751944 |  |
| n628 | *Homo sapiens* Chromosome 16 BAC clone CIT987SK-A-923A4 | 1553550 | AA962431 | 3134595 |  |
| n629 | EST | 773279 | AA425295 | 2106105 |  |
|  |  |  |  | 2106276 |  |
| n630 | Proteasome 26S subunit, non-ATPase, 10 | 143997 | R77104 | 851736 | NM_002814 |
|  |  |  | R77105 | 851737 |  |
| n631 | signal recognition particle 68 kD | 814791 | AA455242 | 2178018 | NM_014230 |
|  |  |  | AA465622 | 2191789 |  |
| n632 | Hypothetical protein FLJ21963 | 22389 | T74065 | 690740 | NM_024560 |
|  |  |  | T87224 | 715576 |  |
| n633 | Neurotrophic tyrosine kinase, receptor, type 2 | 289428 | N79625 | 1211778 | NM_006180 |
|  |  |  | N63949 | 1242326 |  |
| n634 | Cystatin A | 345957 | W72207 | 1382656 | NM_005213 |
|  |  |  | W77844 | 1388378 |  |
| n635 | Hypothetical protein FLJ22995 | 271421 | N34786 | 1155928 | NM_024831 |
| n636 | Cathepsin C | 845355 | AA644088 | 2569306 | NM_001814 |
| n637 | T-cell leukemia | 151531 | H03864 | 866796 | NM_020550 |
|  |  | 200018 | R97095 | 866797 | NM_020552 |
|  |  |  | R97143 | 982755 | NM_020553 |
|  |  |  |  | 982803 | NM_020554 |
|  |  |  |  |  | NM_012468 |
|  |  |  |  |  | NM_014418 |

TABLE 1-continued

| Marker | Gene Name | Image Clone ID | Image Clone Accession # | Image Clone GI # | Genebank or RefSeq nuc accession # |
|---|---|---|---|---|---|
| n638 | gene near HD on 4p16.3 with homology to hypothetical S. pombe gene | 433256 | AA699419 | 2702613 | |
| n639 | Unamed | 566383 | AA151775 | 1720726 1720675 | |
| n640 | Homo sapiens mRNA for FLJ00074 protein | 752837 | AA481320 AA436384 | 2141298 2210872 | |
| n641 | Unamed | 51496 | H19366 H18927 | 885167 888061 | |
| n642 | Hypothetical protein FLJ13732 similar to tensin | 84560 | T74023 T74394 | 690698 691069 | NM_022748 |
| n643 | Procollagen-lysine, 2-oxoglutarate 5-dioxygenase | 771323 | AA476240 AA476241 | 2204451 2204452 | NM_000302 |
| n644 | Unamed | 855707 | AA663941 | 2617932 | |
| n645 | Homo sapiens, clone IMAGE 3457003 | 713031 | AA282712 AA282599 | 1925515 1925638 | |
| n646 | catenin, alpha 2 | 27270 | R18894 R37305 | 772504 794761 | NM_004389 |
| n647 | Phosphatidylinositol-4-phosphate 5-kinase, type I, beta | 24918 | R39069 | 796525 | NM_003558 |
| n648 | CGI-49 protein | 1630934 | AI018497 | 3233016 | NM_016002 |
| n649 | S-adenosylmethionine decarboxylase 1 | 773204 | AA425692 | 2106412 2112539 | NM_001634 |
| n650 | Ribosomal protein S29 | 307119 | W21102 N93715 | 1266024 1297998 | NM_001032 |
| n651 | Pleckstrin homology, Sec7 and coiled | 33293 | R18844 R43956 | 772454 821833 | NM_013385 |
| n652 | zinc finger protein | 471200 | AA034215 AA033532 | 1505378 1506025 | NM_015871 |
| n653 | Homo sapiens clone IMAGE 121687 | 121687 | T97580 T97628 | 746925 746973 | |
| n654 | Lymphocyte-specific protein tyrosine kinase | 730410 | AA469965 AA420981 | 2099922 2197274 | NM_005356 |
| n655 | FK506-binding protein 5 | 416833 | W86653 W87312 | 1400529 1401377 | NM_004117 |
| n656 | mature T-cell proliferation 1 | 470175 | AA029308 AA029842 | 1496741 1496115 | NM_014221 |
| n657 | fatty acid binding protein 6, ileal | 1916019 | AI311734 | 4006605 | NM_001445 |
| n658 | nudix (nucleoside diphosphate linked moiety X)-type motif 9 | 845352 | AA644080 | 2569298 | NM_024047 |
| n659 | Cytochrome P450, subfamily IIB, polypeptide 7 | 1631209 | AA994287 | 3180832 | |
| n660 | Mesothelin | 843028 | AA488406 AA488541 | 2215837 2215972 | NM_013404 NM_005823 |
| n661 | serum amyloid A1 | 161456 | H25590 H25546 | 894669 894713 | NM_000331 |
| n662 | retinal short-chain dehydrogenase | 300276 | W07107 N79745 | 1242446 1281264 | NM_016245 |
| n663 | Interferon-related developmental regulator 1 | 882483 121948 | AA676598 T97868 T97762 | 2657120 747107 747213 | NM_001550 |
| n664 | Unamed | 824523 | AA490900 | 2220073 | |
| n665 | Cytochrome P450, subfamily IIB, polypeptide 6 | 83231 | T68351 T68287 | 679435 679499 | NM_000767 |
| n666 | Unamed | 544639 | AA074677 AA075299 | 1614604 1615170 | |
| n667 | Hypothetical protein, expressed in osteoblast | 754479 | AA410188 AA410567 | 2069284 2069673 | NM_006820 |
| n668 | Microfibrillar-associated protein 4 | 759163 | AA442695 AA496022 | 2154573 2229343 | |
| n669 | Unamed | 462939 | AA682419 | 2669700 | |
| n670 | Homo sapiens cDNA FLJ20993 | 431284 | AA682626 | 2669907 | |
| n671 | Unamed | 839580 | AA489935 AA489804 | 2220688 2220810 | |
| n672 | Hypothetical protein MGC2452 | 128811 | R10172 R10075 | 762031 762128 | NM_032644 |
| n673 | manic fringe (Drosophila) homolog | 51817 | H22922 H24102 | 891617 892797 | NM_002405 |
| n674 | Nucleoside phosphorylase | 769890 | AA430735 AA430382 | 2110957 2111274 | NM_000270 |
| n675 | Unamed | 431425 | AA706858 | 2716776 | |
| n676 | Unamed | 308105 | W24588 N95322 | 1267592 1301479 | |
| n677 | non-metastatic cells 2, protein | 755239 | AA422139 AA422058 | 2100891 2101007 | NM_002512 |

TABLE 1-continued

| Marker | Gene Name | Image Clone ID | Image Clone Accession # | Image Clone GI # | Genebank or RefSeq nuc accession # |
|---|---|---|---|---|---|
| n678 | 3-hydroxyanthranilate 3,4-dioxygenase | 1635163 109310 | AI005031 T80921 T80846 | 3214541 703731 703806 | NM_012205 |
| n679 | serum constituent protein | 214982 | H74163 | 1047382 1047425 | NM_007061 |
| n680 | Proteasome activator subunit 2 | 511043 | AA102276 AA100289 | 1646580 1646687 | NM_002818 |
| n681 | major histocompatibility complex, class I, F | 1604703 | AA988615 | 3173606 | NM_018950 |
| n682 | Hypothetical protein FLJ10761 | 233349 | H77535 H77536 | 1055624 1055625 | NM_018208 |
| n683 | Homo sapiens cDNA FLJ23593 | 450079 | AA703419 | 2713337 | |
| n684 | Unamed | 712604 | AA281932 | 1924610 | |
| n685 | Hypothetical protein FLJ14590 | 839941 | AA490142 AA489961 | 2220836 2221017 | NM_032807 |
| n686 | KIAA1424 protein | 795277 | AA454021 AA451811 | 2165480 2167690 | |
| n687 | lectin, galactoside-binding, soluble, 3 binding protein | 811000 | AA485508 AA485353 | 2214572 2214727 | NM_005567 |
| n688 | delta-like homolog | 296815 436121 | W01204 N74203 AA701996 | 1231488 1273183 2705109 | NM_003836 |
| n689 | LIM domain only 4 | 162533 | H27986 | 898339 | NM_006769 |
| n690 | serine threonine protein kinase | 826135 | AA521346 | 2261889 | NM_007271 |
| n691 | Programmed cell death 10 | 137836 | R68344 R68555 | 841861 842072 | NM_007217 |
| n692 | Unamed | 823819 | AA490281 AA490390 | 2219454 2219563 | |
| n693 | CASP2 and RIPKI domain containing adaptor with death domain | 24032 700353 | T78285 R37937 AA290955 AA285065 | 795393 696794 1927951 1938789 | NM_003805 |
| n694 | vesicle-associated membrane protein 3 | 843248 | AA486016 AA488635 | 2216232 2216066 | NM_004781 |
| n695 | Olfactory receptor, family 7, subfamily E, member 12 pseudogene | 1291972 | AA707468 | 2717386 | |
| n696 | Regenerating islet-derived 1 beta | 1412300 | AA844864 | 2931315 | NM_006507 |
| n697 | aldo-keto reductase family 1, member C1 | 196992 | R93124 | 967290 | NM_001353 |
| n698 | Homo sapiens serologically defined breast cancer antigen NY-BR-96 | 511257 127458 | AA088799 AA088722 R08769 R08768 | 1634234 1634345 760691 768825 | |
| n699 | ataxia telangiectasia mutated | 360778 | AA016988 AA016254 | 1477301 1479171 | NM_000051 |
| n700 | Otoferlin | 38517 | R51235 R51236 | 813137 813138 | NM_004802 |
| n701 | Hypothetical protein FLJ12783 | 178922 | H48148 H49932 | 924200 989773 | NM_031426 |
| n702 | nuclear factor -like 3 | 1034644 | AA779843 | 2839174 | NM_004289 |
| n703 | Basonuclin | 132373 | R25330 R26526 | 781465 782661 | NM_001717 |
| n704 | Hypothetical protein FLJ20421 | 502656 | AA125789 AA127047 | 1687760 1687659 | NM_017813 |
| n705 | H19, imprinted maternally expressed untranslated mRNA | 884644 | AA629897 | 2552508 | |
| n706 | AD-012 protein | 787925 | AA452282 | 2165951 | NM_018449 |
| n707 | Activating transcription factor 5 | 1472585 | AA872311 | 2968489 | NM_012068 |
| n708 | Latrophilin | 897731 | AA598995 | 2432035 | NM_012302 |
| n709 | Not56-like protein | 131091 | R23327 R23251 | 778139 778215 | NM_005787 |
| n710 | fatty acid desaturase 1 | 782503 | AA431773 AA432026 | 2115481 2115734 | NM_013402 |
| n711 | Cdc42 effector protein 4; binder of Rho GTPases 4 | 321488 | W32606 W32509 | 1313499 1313616 | NM_012121 |
| n712 | Niemann-Pick disease, type C1 | 868484 | AA634267 | 2557601 | NM_000271 |
| n713 | CGI-115 protein | 772918 | AA479913 | 2204395 | NM_016052 |
| n714 | CTP synthase | 46182 | H09614 | 874435 874436 | NM_001905 |
| n715 | Interleukin 1 receptor-like 1 | 501994 | AA125917 AA128153 | 1687503 1687395 | NM_003856 NM_016232 |
| n716 | Enolase 1 | 392678 | AA708342 | 2718260 | NM_001428 |
| n717 | v-yes-1 Yamaguchi sarcoma viral related oncogene homolog | 193913 | R83836 R83837 | 928713 928714 | NM_002350 |
| n718 | Spermidine synthase | 856796 | AA669545 | 2631044 | NM_003132 |

TABLE 1-continued

| Marker | Gene Name | Image Clone ID | Image Clone Accession # | Image Clone GI # | Genebank or RefSeq nuc accession # |
|---|---|---|---|---|---|
| n719 | nuclear autoantigenic sperm protein (histone-binding) | 447918 | AA644128 | 2569346 | NM_002482 |
| n720 | Phosphoglucomutase 1 | 843174 | AA488373 | 2215804 | NM_002633 |
|  |  |  | AA488504 | 2215935 |  |
| n721 | Unamed | 809466 | AA456161 | 2179371 | NM_006114 |
|  |  |  | AA443094 | 2155769 |  |
| n722 | NADH dehydrogenase | 562409 | AA214053 | 1812675 | NM_004552 |
|  |  |  | AA214154 | 1812791 |  |
| n723 | Hypothetical protein | 752690 | AA417805 | 2079589 | NM_016505 |
|  |  |  | AA417806 | 2079590 |  |
| n724 | Interleukin 10 receptor, alpha | 757440 | AA437226 | 2142140 | NM_001558 |
|  |  |  | AA442290 | 2154168 |  |
| n725 | Exportin 1 | 109333 | T59055 | 660892 | NM_003400 |
|  |  |  | T59131 |  |  |
| n726 | Phosphofructokinase, platelet | 950682 | AA608558 | 2456986 | NM_002627 |
| n727 | *Homo sapiens* mRNA for KIAA1750 protein | 745011 | AA626024 | 2538411 |  |
| n728 | Ser/Arg-related nuclear matrix protein | 132395 | AA976063 | 3151855 | NM_005839 |
| n729 | Bromodomain-containing 4 | 511865 | AA085917 | 1629293 | NM_014299 |
|  |  |  | AA085918 | 1629294 |  |
| n730 | major histocompatibility complex, class I, C | 810142 | AA464354 | 2189238 | NM_002117 |
|  |  |  | AA464246 | 2189130 |  |
| n731 | Ras homolog enriched in brain 2 | 756401 | AA482117 | 2209795 | NM_005614 |
| n732 | U6 snRNA-associated Sm-like protein LSm7 | 741842 | AA402875 | 2056629 | NM_016199 |
| n733 | Polypyrimidine tract binding protein | 897233 | AA677517 | 2658039 | NM_002819 |
| n734 | Catenin | 177772 | H45976 | 922028 | NM_004389 |
|  |  | 48677 | H46041 | 922093 |  |
|  |  |  | H16078 | 880898 |  |
|  |  |  | H16079 | 880899 |  |
| n735 | *Homo sapiens* mRNA cDNA DKFZp564H1916 | 855244 | AA630545 | 2553156 |  |
| n736 | Unamed | 725630 | AA293211 | 1941492 |  |
|  |  |  | AA293653 | 1941493 |  |

TABLE 2

| Marker | Gene Name | Image Clone ID | Image Clone Accession # | Image Clone GI # | Genbank or RefSeq nuc accession# |
|---|---|---|---|---|---|
| n1 | CGI-49 protein | 123255 | R00275 | 750011 | NM_016002 |
|  |  |  | T99925 | 749662 |  |
| n2 | Unamed | 490965 | AA120865 | 1678196 |  |
|  |  |  | AA120866 | 1678197 |  |
| n3 | Laminin, beta 2 | 502518 | AA156802 | 1728435 | NM_002292 |
|  |  |  | AA156926 | 1728541 |  |
| n4 | Unamed | 279837 | N38839 | 1162046 |  |
| n5 | Synaptotagmin-like 2 | 487932 | AA045284 | 1523712 | NM_032379 |
|  |  | 826194 | AA046565 | 1524462 | NM_032943 |
|  |  |  | AA521439 | 2261982 |  |
| n6 | Unamed | 29967 | R14766 | 769039 |  |
|  |  |  | R42536 | 817298 |  |
| n7 | Unamed | 841621 | AI732756 | 2217632 |  |
|  |  |  | AI734150 | 2217847 |  |
|  |  |  | AA487683 |  |  |
|  |  |  | AA487468 |  |  |
| n8 | Plasminogen activator | 813841 | AA447797 | 2161467 | NM_000930 |
|  |  |  | AA453728 | 2167397 | NM_000931 |
|  |  |  |  |  | NM_033011 |
| n9 | GDNF family receptor alpha 1 | 1641451 | AI024284 | 3239897 | NM_005264 |
| n10 | Estrogen receptor 1 | 725321 | AA291749 | 1939868 | NM_000125 |
|  |  |  | AA291702 | 1939745 |  |
| n11 | Suppressor of *S. cerevisiae* gcr2 | 25154 | T80582 | 796389 | NM_007265 |
|  |  |  | R38933 | 699091 |  |
| n12 | *Homo sapiens* clone 25194 mRNA sequence | 155227 | AI732288 | 843038 |  |
|  |  |  | R69521 | 843039 |  |
|  |  |  | R69522 |  |  |
| n13 | *Homo sapiens* cDNA FLJ10561 | 1554430 | AA931491 | 3085877 |  |
| n14 | Unamed | 392630 | AA708301 | 2718219 |  |
| n15 | Reticulon 1 | 858450 | AA773983 | 2825872 | NM_021136 |
| n16 | Unamed | 25194 | R39044 | 796500 |  |

TABLE 2-continued

| Marker | Gene Name | Image Clone ID | Image Clone Accession # | Image Clone GI # | Genbank or RefSeq nuc accession# |
|---|---|---|---|---|---|
| n17 | netrin 4 | 143661 | R76613 | 851262 | NM_021229 |
|  |  |  | R76614 | 851263 |  |
| n18 | non-metastatic cells 3, protein expressed in | 726658 | AA398218 | 2051345 | NM_002513 |
|  |  |  | AA399289 | 2053042 |  |
| n19 | Unamed | 784282 | AA447486 | 2161155 |  |
|  |  |  |  | 2161156 |  |
| n20 | trefoil factor 3 | 298417 | N74131 | 1231416 | NM_003226 |
| n21 | Homo sapiens mRNA; cDNA DKFZp434E082 | 44387 | H06525 | 870057 |  |
|  |  |  | H06580 | 870112 |  |
| n22 | Homo sapiens mRNA; cDNA DKFZp434N2412 | 772890 | AA479888 | 2112474 |  |
|  |  |  |  | 2204370 |  |
| n23 | LIV-1 protein, estrogen regulated | 52933 | H29315 | 900225 | NM_012319 |
|  |  |  | H29407 | 900317 |  |
| n24 | Unamed | 51700 | H22853 | 891548 |  |
|  |  |  | H22854 | 891549 |  |
| n25 | Unamed | 52021 | H24419 | 891261 |  |
|  |  |  | H22566 | 893114 |  |
| n26 | GATA-binding protein 3 | 214068 | H72474 | 1044290 | NM_002051 |
|  |  | 365681 | H72875 | 1044691 | NM_032742 |
|  |  |  | AA025380 | 1490899 |  |
|  |  |  | AA025379 | 1490900 |  |
| n27 | UDP-glucose ceramide glucosyltransferase | 739123 | AA421691 | 2100508 | NM_003358 |
|  |  |  | AA421692 | 2100509 |  |
| n28 | Homo sapiens, clone MGC 17687 IMAGE 3865868 | 214205 | H77627 | 1055716 |  |
|  |  |  |  | 1055886 |  |
| n29 | UDP-glucose ceramide glucosyltransferase | 302540 | W38595 | 1443531 | NM_003358 |
|  |  |  | N90204 | 1320257 |  |
| n30 | vav 3 oncogene | 46827 | H10098 | 874867 | NM_006113 |
|  |  | 415229 | H10045 | 874920 |  |
|  |  |  | W91879 | 1424261 |  |
|  |  |  | W91952 | 1424313 |  |
| n31 | CEGP1 protein | 346321 | W79647 | 1384330 | NM_020974 |
|  |  | 242778 | W74079 | 1390075 |  |
|  |  |  | H93602 | 1099930 |  |
|  |  |  | H93603 | 1099931 |  |
| n32 | solute carrier family 2, member 10 | 429263 | AA007343 | 1463347 | NM_030777 |
|  |  | 758347 | AA007344 | 1463348 |  |
|  |  |  | AA403072 | 2055616 |  |
|  |  |  | AA404352 | 2059077 |  |
| n33 | Homo sapiens mRNA; cDNA DKFZp727C191 | 785703 | AA449591 | 2163183 |  |
|  |  |  | AA449334 | 2163341 |  |
| n34 | Unamed | 279838 | N38836 | 1162043 |  |
| n35 | Unamed | 282980 | N45139 | 1186305 |  |
| n36 | Unamed | 33985 | R44918 | 823185 |  |
| n37 | Homo sapiens mRNA; cDNA DKFZp564F053 | 78041 | T61343 | 663770 |  |
|  |  |  | T60500 | 664380 |  |
| n38 | Unamed | 49567 | H15113 | 879933 |  |
|  |  |  | H15114 | 879934 |  |
| n39 | LIM and SH3 protein 1 | 392093 | AI003699 | 3204033 | NM_006148 |
| n40 | Hypothetical protein FLJ12910 | 785795 | AA449754 | 2163058 | NM_024573 |
|  |  |  | AA449038 | 2163504 |  |
| n41 | Unamed | 291462 | N72847 | 1229951 |  |
|  |  |  | W03066 | 1275044 |  |
| n42 | GLI-Kruppel family member GLI3 | 767495 | AA418036 | 2079847 | NM_000168 |
|  |  |  | AA418190 | 2080009 |  |
| n43 | Unamed | 882467 | AA676408 | 2656930 |  |
| n44 | Homo sapiens mRNA; cDNA DKFZp586G0321 | 504959 | AA149050 | 1719458 |  |
|  |  |  | AA149051 | 1719459 |  |
| n45 | v-myb avian myeloblastosis viral oncogene homolog | 243549 | N49526 | 1190450 | NM_005375 |
|  |  |  | N49284 | 1190692 |  |
| n46 | Chondroadherin | 1507713 | AA937215 | 3095326 | NM_001267 |
| n47 | KIAA0100 gene product | 1631355 | AI024502 | 3240115 | NM_014680 |
| n48 | Duodenal cytochrome b | 244310 | N75713 | 1196108 | NM_024843 |
|  |  | 838446 | N54788 | 1238291 |  |
|  |  |  | AA457501 | 2180221 |  |
|  |  |  | AA457594 | 2180314 |  |
| n49 | Cbp p300-interacting transactivator, with Glu | 491565 | AA115076 | 1670339 | NM_006079 |
| n50 | Unamed | 812041 | AA455976 | 2178752 |  |
| n51 | Dachshund (Drosophila) homolog | 132326 | R25458 | 781593 | NM_004392 |
|  |  |  | R26283 | 782418 |  |
| n52 | Neuropeptide Y receptor Y1 | 33045 | R43817 | 773088 | NM_000909 |
|  |  | 143332 | R19478 | 821697 |  |
|  |  |  | R74183 | 848553 |  |
|  |  |  | R74269 | 848639 |  |

TABLE 2-continued

| Marker | Gene Name | Image Clone ID | Image Clone Accession # | Image Clone GI # | Genbank or RefSeq nuc accession# |
|---|---|---|---|---|---|
| n53 | Unamed | 1031791 | AA609651 | 2458079 | |
| n54 | *Homo sapiens* mRNA; cDNA DKFZp434E2321 | 590310 | AA157456 AA156269 | 1727904 1729063 | |
| n55 | Unamed | 282564 | N52073 | 1193239 | |
| n56 | protein tyrosine phosphatase, receptor type, T | 41647 | R52793 R52794 | 814695 814696 | NM_007050 |
| n57 | Anterior gradient 2 (*Xenepus laevis*) homolog | 510576 | AA055768 AA055880 | 1548168 1548218 | NM_006408 |
| n58 | X-box binding protein 1 | 417867 | W90224 W90128 | 1406118 1406214 | NM_005080 |
| n59 | Interleukin 6 signal transducer | 2018581 753743 | AI360116 AA406546 | 4111737 2064660 2069400 | NM_002184 |
| n60 | RNB6 | 26294 | R20625 R13504 | 766580 775406 | NM_016337 |
| n61 | Unamed | 365665 | AA025386 AA026030 | 1491525 1491449 | |
| n62 | HMBA-inducible | 897722 | AA598983 | 2432023 | NM_006460 |
| n63 | Cysteine-rich protein 1 | 1323448 | AA873604 | 2969726 | NM_001311 |
| n64 | Unamed | 399463 | AA732944 | 2754303 | |
| n65 | Carboxypeptidase B1 | 2063284 | AI382830 | 4195611 | NM_001871 |
| n66 | Unamed | 39577 | R51889 R54279 | 813791 816181 | |
| n67 | nuclear receptor subfamily 5, group A, member 2 | 128457 | R10138 | 762094 762501 | NM_003822 |
| n68 | Unamed | 260170 | N32072 N45384 | 1152471 1186550 | |
| n69 | solute carrier family 12 (sodium potassium | 685801 | AA255695 AA262080 | 1892633 1898204 | NM_001046 |
| n70 | Phosphorylase, glycogen; liver | 241705 | H91680 H91776 | 1087258 1087354 | NM_002863 |
| n71 | Androgen induced protein | 66977 | T69554 T67558 | 678706 680702 | NM_016108 |
| n72 | Hypothetical protein CAB56184 | 502349 | AA135715 AA156935 | 1697220 1728550 | NM_032520 |
| n73 | Purinergic receptor P2X, ligand-gated ion channel, 4 | 42118 | R60722 R60723 | 831417 831418 | NM_002560 |
| n74 | *Homo sapiens* cDNA FLJ12425 | 51103 | H19216 H19217 | 885456 885457 | |
| n75 | N-acetyltransferase 1 | 195525 66599 | R91802 R91803 T67129 | 959342 959343 676568 676569 | NM_000662 |
| n76 | DEME-6 protein | 1492468 | AA886199 | 3001307 | |
| n77 | lectin, galactoside-binding, soluble, 8 | 197903 | R96336 R96337 | 981996 981997 | NM_006499 |
| n78 | SH3 domain binding glutamic acid-rich protein like | 1603583 | AA996131 | 3182620 | NM_003022 |
| n79 | Receptor activity modifying protein 3 | 345663 | W76411 W72393 | 1382349 1386655 | NM_005856 |
| n80 | leucine zipper transcription factor-like 1 | 754033 | AA479063 AA480036 | 2207619 2208187 | NM_020347 |
| n81 | Transcription elongation factor A (SII)-like 1 | 786607 | AA478480 AA451969 | 2165638 2207114 | NM_004780 |
| n82 | Hypothetical protein FLJ12890 | 292270 | N79195 N62475 | 1210304 1241896 | NM_015442 |
| n83 | Hypothetical protein FLJ12650 | 41569 | R67272 R52900 R52901 | 814803 839910 | NM_024522 |
| n84 | G protein-coupled receptor | 246786 | N53172 | 1194338 1202499 | |
| n85 | RAB31 | 785701 120881 | AA449590 AA449333 T96082 T96083 | 2163182 2163340 734706 734707 | NM_006868 |
| n86 | Unamed | 377987 | AA788874 | 2848994 | |
| n87 | Stanniocalcin 1 | 547247 | AA085318 AA085319 | 1627385 1627386 | NM_003155 |
| n88 | Secretory carrier membrane protein 1 | 824025 | AA490945 | 2220118 | NM_004866 |
| n89 | Unamed | 669359 | AA236793 AA236840 | 1860813 1860870 | |
| n90 | Unamed | 742596 | AA400080 | 2053883 2054012 | |
| n91 | acyl-Coenzyme A oxidase 2, branched chain | 85450 | T71782 T71713 | 686234 686303 | NM_003500 |

TABLE 2-continued

| Marker | Gene Name | Image Clone ID | Image Clone Accession # | Image Clone GI # | Genbank or RefSeq nuc accession# |
|---|---|---|---|---|---|
| n92 | serine proteinase inhibitor, clade A, member 5 | 416567 | W86431 | 1400197 1400198 | NM_000624 |
| n93 | Hypothetical gene BC008967 | 782497 | AA431770 AA432023 | 2115478 2115731 | |
| n94 | Unamed | 33821 | R45924 R19826 | 774460 824257 | |
| n95 | Stanniocalcin 2 | 823578 130057 | AA497118 AA497040 R20886 R20779 | 2230361 2230439 775560 775667 | NM_003714 |
| n96 | *Homo sapiens* clone 24566 mRNA sequence | 165807 | R86667 | 945518 945478 | |
| n97 | gap junction protein, alpha 1, 43 kD | 839101 | AA487623 | 2217787 | NM_000165 |
| n98 | Unamed | 726580 | AA394105 AA398134 | 2047093 2051243 | |
| n99 | normal mucosa of esophagus specific 1 | 1056172 | AA620995 | 2524934 | NM_032413 |
| n100 | Unamed | 155072 | AI732325 R71393 AI820748 | 5439827 844910 | |
| n101 | Unamed | 33076 | R18933 R44048 | 772543 821916 | |
| n102 | Fibroblast growth factor receptor 1 | 154472 | R54610 R54846 | 819042 818968 | NM_000604 NM_023105 NM_023106 NM_023107 NM_023108 NM_023109 NM_023110 NM_023111 NM_015850 |
| n103 | *Homo sapiens* genomic DNA, chromosome 21q, section 4 | 461284 | AA699859 | 2702822 | |
| n104 | Hypothetical protein FLJ11026 | 249784 | H84010 H84011 | 1062681 1062682 | NM_018303 |
| n105 | Chitinase 1 | 119384 | T94272 T94579 | 727760 728067 | NM_003465 |
| n106 | Unamed | 854831 | AA630241 | 2552852 | |
| n107 | Unamed | 795907 | AA460346 AA460775 | 2185559 2185895 | |
| n108 | Unamed | 42415 | R60981 R61649 | 831676 832344 | |
| n109 | Hypothetical protein FLJ13110 | 782306 | AA431233 AA432253 | 2114941 2114641 | NM_022912 |
| n110 | RAB38, member RAS oncogene family | 263047 | N20045 | 1124712 | NM_022337 |
| n111 | pre-B-cell leukemia transcription factor 1 | 2018074 741880 | AI364369 AA403031 AA401304 | 4124058 2053547 2056768 | NM_002585 |
| n112 | 5'-3' exoribonuclease 2 | 364840 | AA035728 AA028164 | 1494289 1507565 | NM_012255 |
| n113 | Coxsackie virus and adenovirus receptor | 276712 | N46621 N34895 | 1156037 1187787 | NM_001338 |
| n114 | *Homo sapiens* cDNA FLJ12993 fis, clone NT2RP3000197 | 950410 | AA599064 | 2432689 | |
| n115 | Polymerase (DNA-directed), delta 4 | 810734 | AA480820 AA457710 | 2180430 2210372 | NM_021173 |
| n116 | *Homo sapiens* cDNA FLJ11685 | 796152 | AA461390 AA461078 | 2186198 2185254 | |
| n117 | WW domain-containing protein 1 | 141959 | R67561 R67562 | 840199 840200 | NM_007013 |
| n118 | Unamed | 813168 | AA456306 AA456704 | 2179516 2179280 | |
| n119 | Pregnancy specific beta-1-glycoprotein 1 | 199635 | R96522 R96568 | 982182 982228 | NM_006905 |
| n120 | Programmed cell death 9 | 270558 | N33236 | 1153635 | NM_016640 |
| n121 | Synaptotagmin XIII | 23443 | R38678 T75313 | 796134 692075 | |
| n122 | Unamed | 754260 | AA479272 | 2207828 2207924 | |
| n123 | Hypothetical protein FLJ21213 | 1572710 | AA969799 | 3145312 | NM_022900 |
| n124 | Hypothetical protein FLJ22724 | 772944 | AA425184 | 2105976 2204462 | NM_024532 |
| n125 | Glypican 3 | 878564 | AA775872 | 2835206 | NM_004484 |
| n126 | Hypothetical protein similar to small G proteins, especially RAP-2A | 487929 | AA045481 AA046513 | 1523717 1524468 | NM_021183 |

TABLE 2-continued

| Marker | Gene Name | Image Clone ID | Image Clone Accession # | Image Clone GI # | Genbank or RefSeq nuc accession# |
|---|---|---|---|---|---|
| n127 | Unamed | 48642 | H14677 | 879403 | |
| | | | H14583 | 879497 | |
| n128 | N-acylsphingosine amidohydrolase | 855487 | AA664155 | 2618146 | NM_004315 |
| n129 | Amphiregulin | 1410444 | AA857163 | 2945465 | NM_001657 |
| n130 | KIAA0942 protein | 666451 | AA232926 | 1856039 | NM_015310 |
| | | 731240 | AA232939 | 1855931 | |
| | | | AA417363 | 2077776 | |
| | | | AA416817 | 2077673 | |
| n131 | Unamed | 450327 | AA703619 | 2713537 | |
| n132 | Unamed | 824995 | AA489100 | 2218702 | |
| | | | AA489185 | 2218787 | |
| n133 | Ribosomal protein S23 | 868308 | AA634008 | 2557222 | NM_001025 |
| n134 | Duodenal cytochrome b | 491415 | AA150422 | 1721935 | NM_024843 |
| | | | AA156591 | 1728233 | |
| n135 | Unamed | 767706 | AA417956 | 2079775 | |
| | | | AA418061 | 2079935 | |
| n136 | *Homo sapiens* cDNA FLJ11663 fis, clone HEMBA 1004631 | 1291971 | AA707477 | 2717395 | |
| n137 | Parathyroid hormone-like hormone | 1404774 | AA845432 | 2933191 | NM_002820 |
| n138 | C-type lectin, superfamily member 1 | 726645 | AA399390 | 2051339 | NM_005752 |
| | | | AA398015 | 2053135 | |
| n139 | CD44 antigen | 328868 | W40475 | 1324428 | NM_000610 |
| | | 713145 | W45275 | 1329588 | |
| | | | AA283090 | 1925839 | |
| | | | AA282906 | 1926015 | |
| n140 | Unamed | 855634 | AA664105 | 2618096 | |
| n141 | Attractin | 47626 | H11351 | 876145 | NM_012070 |
| | | | H11325 | 876171 | |
| n142 | PDZ domain protein | 428338 | AA005153 | 1447808 | NM_005799 |
| | | | AA005420 | 1447902 | |
| n143 | Unamed | 32092 | R17347 | 770957 | |
| | | | R42695 | 819640 | |
| n144 | Programmed cell death 4 (neoplastic transformation inhibitor) | 294487 | N71003 | 1227583 | NM_014456 |
| | | | | 1273516 | |
| n145 | *Homo sapiens* cDNA FLJ13603 fis, | 506128 | AA708864 | 2718782 | |
| n146 | Glutamate receptor, ionotropic, AMPA2 | 364141 | AA021212 | 1484937 | NM_000826 |
| | | 282958 | AA021343 | 1485032 | |
| | | 49987 | N45132 | 1186298 | |
| | | | H28734 | 899688 | |
| | | | H28864 | 899774 | |
| n147 | DKFZP564K247 protein | 84613 | T74479 | 690780 | NM_014056 |
| | | | T74105 | 691154 | |
| n148 | Hypothetical protein MGC2771 | 1558642 | AA976544 | 3153990 | NM_024101 |
| n149 | Parathyroid hormone | 322051 | W37305 | 1319036 | NM_000315 |
| | | | W37306 | 1319037 | |
| n150 | Unamed | 810235 | AA464707 | 2189591 | |
| n151 | *Homo sapiens*, Similar to clone FLB3816, | 130835 | R22198 | 776979 | |
| | | | R22252 | 777033 | |
| n152 | Pregnancy specific beta-1-glycoprotein 11 | 143287 | R74004 | 848279 | NM_002785 |
| | | | R73909 | 848374 | |
| n153 | Hypothetical protein FLJ22087 | 510575 | AA057741 | 1550400 | NM_022070 |
| | | | AA057742 | 1550401 | |
| n154 | Eukaryotic translation initiation factor 2C, 1 | 813850 | AA453723 | 2161461 | NM_012199 |
| | | | AA447791 | 2167392 | |
| n155 | Pregnancy specific beta-1-glycoprotein 9 | 141677 | R69567 | 843084 | NM_002784 |
| | | | R69649 | 843166 | |
| n156 | Glutathione S-transferase M3 | 137940 | R63106 | 834944 | NM_000849 |
| | | | R63065 | 834985 | |
| n157 | Hypothetical protein PRO2975 | 684073 | AA251288 | 1886198 | |
| | | | AA251217 | 1886269 | |
| n158 | KIAA0728 protein | 51708 | H24092 | 891609 | |
| | | | H22914 | 892787 | |
| n159 | Meis homolog 3 | 450152 | AA703449 | 2713367 | |
| n160 | bone morphogenetic protein 4 | 797048 | AA463225 | 2188108 | NM_001202 |
| | | | AA463224 | 2188109 | |
| n161 | Unamed | 1292170 | AA705819 | 2715737 | |
| n162 | low density lipoprotein-related protein 2 | 143846 | R75977 | 850659 | NM_004525 |
| | | | R76808 | 851440 | |
| n163 | Unamed | 252830 | H88261 | 1069629 | |
| | | | | 1069840 | |
| n164 | Ectonucleoside triphosphate diphosphohydrolase 5 | 1635701 | AI017442 | 3231778 | NM_001249 |

TABLE 2-continued

| Marker | Gene Name | Image Clone ID | Image Clone Accession # | Image Clone GI # | Genbank or RefSeq nuc accession# |
|---|---|---|---|---|---|
| n165 | Ectonucleotide pyrophosphatase | 322461 | W15305 | 1289705 | NM_021572 |
| | | 82991 | T70503 | 680598 | |
| | | 281737 | T69450 | 681651 | |
| | | | N51740 | 1192906 | |
| n166 | Hypothetical protein | 594600 | AA171951 | 1750797 | NM_019049 |
| | | | AA171739 | 1751010 | |
| n167 | Unamed | 275372 | R85509 | 943915 | |
| n168 | Glutathione S-transferase M5 | 377731 | AA056231 | 1548568 | NM_000851 |
| | | | AA056232 | 1548569 | |
| n169 | Cytochrome P450, subfamily IVB, polypeptide 1 | 724888 | AA404692 | 1939505 | NM_000779 |
| | | | AA291484 | 2058871 | |
| n170 | serine proteinase inhibitor, clade A (alpha-1 antiproteinase, antitrypsin), member 6 | 240518 | H90764 | 1081194 | NM_001756 |
| | | | H90815 | 1081245 | |
| n171 | amylo-1,6-glucosidase, 4-alpha-glucanotransferase | 853687 | AA668425 | 2629924 | NM_000028 |
| | | | | | NM_000642 |
| | | | | | NM_000643 |
| | | | | | NM_000644 |
| | | | | | NM_000645 |
| | | | | | NM_000646 |
| n172 | Collagen, type IV, alpha 5 | 470001 | AA029107 | 1496528 | NM_000495 |
| | | | AA029997 | 1496428 | |
| n173 | Corticotropin releasing hormone-binding protein | 266336 | N35660 | 1140894 | NM_001882 |
| | | | N26546 | 1156802 | |
| n174 | KIAA0040 gene product | 814054 | AA465478 | 2191645 | NM_014656 |
| | | | AA465479 | 2191646 | |
| n175 | Stathmin-like 3 | 1631253 | AA994305 | 3180850 | NM_015894 |
| n176 | Hypothetical protein FLJ10261 | 742679 | AA400086 | 2053906 | NM_018043 |
| | | | AA401376 | 2053584 | |
| n177 | Unamed | 49919 | H29088 | 899893 | |
| | | | H28983 | 899998 | |
| n178 | Pleiotrophin | 361974 | AA001449 | 1436914 | NM_002825 |
| | | | | 1436950 | |
| n179 | sodium channel, voltage gated, type VIII, alpha polypeptide | 361668 | W96187 | 1426093 | NM_014191 |
| | | | W96278 | 1426185 | |
| n180 | Hypothetical protein DKFZp566I133 | 824908 | AA489012 | 2218614 | NM_030938 |
| | | | AA489105 | 2218707 | |
| n181 | tumor necrosis factorsuperfamily, member 13 | 771240 | AA443577 | 2156252 | NM_003808 |
| n182 | Ortholog of mouse integral membrane glycoprotein LIG-1 | 878094 | AA775396 | 2834730 | |
| n183 | Glutamate dehydrogenase 1 | 361565 | AA017175 | 1479340 | NM_005271 |
| | | | AA018372 | 1481628 | |
| n184 | Hypothetical protein DKFZp434P0116 | 417863 | W89179 | 1404472 | NM_017593 |
| | | 264609 | W88781 | 1404471 | |
| | | | N20237 | 1125192 | |
| | | | N29303 | 1147539 | |
| n185 | Unamed | 324236 | AA284185 | 1928530 | |
| | | | W47507 | 1332158 | |
| | | | W47508 | | |
| n186 | sema domain, immunoglobulin domain (Ig), short basic domain, secreted, 3C | 486591 | AA043044 | 1522505 | NM_006379 |
| | | | AA042990 | 1522624 | |
| n187 | Hypothetical protein FLJ10374 | 897159 | AA676962 | 2657484 | NM_018074 |
| n188 | NK homeobox, family 3, A | 757435 | AA437224 | 2142138 | NM_006167 |
| | | | AA442287 | 2154165 | |
| n189 | Epiregulin | 271744 | N42596 | 1151984 | NM_001432 |
| | | | N31585 | 1167026 | |
| n190 | acyl-Coenzyme A dehydrogenase, short | 243100 | H95792 | 1108934 | NM_001609 |
| | | | H96140 | 1109282 | |
| n191 | Activated RNA polymerase II transcription cofactor 4 | 280465 | N51590 | 1191541 | NM_006713 |
| | | | N50375 | 1192756 | |
| n192 | Unamed | 24855 | R38952 | 796408 | |
| | | | | 698810 | |
| n193 | IK cytokine, down-regulator of HLA II | 453230 | AA704849 | 2714767 | NM_006083 |
| n194 | zinc finger protein 254 | 646891 | AA205649 | 1803746 | NM_004876 |
| | | | | 1803775 | |
| n195 | Unamed | 549558 | AA129284 | 1689033 | |
| | | | AA129249 | 1689067 | |
| n196 | Unamed | 1030726 | AA620287 | 2524226 | |
| n197 | Programmed cell death 6-interacting protein | 377245 | AA055248 | 1547556 | NM_013374 |
| | | | AA055218 | 1547648 | |
| n198 | Hypothetical protein, estradiol-induced | 757462 | AA442301 | 2142150 | NM_014367 |
| | | | AA437236 | 2154179 | |
| n199 | *Homo sapiens* cDNA FLJ11027 fis, clone PLACE1004114 | 141453 | R68996 | 842513 | |
| | | | R68997 | 842514 | |

TABLE 2-continued

| Marker | Gene Name | Image Clone ID | Image Clone Accession # | Image Clone GI # | Genbank or RefSeq nuc accession# |
|---|---|---|---|---|---|
| n200 | Unamed | 172817 | H19803 | 888498 | |
| | | | H19804 | 888499 | |
| n201 | Unamed | 344073 | W73414 | 1383858 | |
| | | | W73738 | 1383883 | |
| n202 | Unamed | 42120 | R59618 | 830313 | |
| | | | R59678 | 830373 | |
| n203 | Unamed | 431733 | AA677803 | 2658325 | |
| n204 | ELL-RELATED RNA POLYMERASE II, ELONGATION FACTOR | 767988 | AA418818 | 2080619 | NM_012081 |
| | | | AA418943 | 2080744 | |
| n205 | Cadherin 18, type 2 | 1469249 | AA865745 | 2958021 | NM_004934 |
| n206 | fragile histidine triad gene | 681948 | AA256122 | 1891875 | NM_002012 |
| | | | AA256123 | 1891876 | |
| n207 | Complement component 6 | 246246 | N77085 | 1203286 | NM_000065 |
| | | | N59396 | 1239663 | |
| n208 | Adrenergic, alpha-2A-, receptor | 69935 | T48691 | 650551 | NM_000681 |
| | | | T48692 | 650552 | |
| n209 | Unamed | 436463 | AA699656 | 2703803 | |
| n210 | mucin 2, intestinal | 1435339 | AA857748 | 2946050 | NM_002457 |
| n211 | Unamed | 214996 | H73239 | 5440539 | |
| | | | AI820827 | 1047387 | |
| | | | AI821460 | | |
| n212 | KIAA1189 protein | 36462 | R62449 | 781840 | |
| | | | R25705 | 834328 | |
| n213 | pre-B-cell leukemia transcription factor 3 | 448386 | AA778198 | 2836913 | NM_006195 |
| n214 | Unamed | 361653 | W96347 | 1426262 | |
| | | | | 1426263 | |
| n215 | Unamed | 345635 | W72062 | 1382332 | |
| | | | W76255 | 1386637 | |
| n216 | Unamed | 503520 | AA131325 | 1692800 | |
| | | | AA131275 | 1693012 | |
| n217 | distal-less homeo box 2 | 1486752 | AA912071 | 3051463 | NM_004405 |
| n218 | Hypothetical protein FLJ21212 | 502625 | AA134576 | 1695573 | NM_024642 |
| n219 | Jumping translocation breakpoint | 1636072 | AI015527 | 3229863 | NM_006694 |
| n220 | CGI-109 protein | 260628 | H97565 | 1118450 | |
| n221 | Unamed | 360357 | AA013354 | 1474460 | |
| | | | AA013355 | 1474461 | |
| n222 | Unamed | 1622424 | AI016151 | 3230487 | |
| n223 | KIAA1223 protein | 726599 | AA394303 | 2047298 | |
| | | | AA397920 | 2051261 | |
| n224 | Organic cation transporter | 1456155 | AA862473 | 2954952 | NM_020372 |
| n225 | Adenylyl cyclase-associated protein 2 | 487297 | AA040613 | 1516909 | NM_006366 |
| | | | AA045508 | 1523744 | |
| n226 | Uncharacterized hypothalamus protein HTMP | 1628069 | AA993905 | 3180450 | NM_018475 |
| n227 | ATPase, Cu++ transporting, beta polypeptide | 266312 | N26536 | 1140884 | NM_000053 |
| | | | N35647 | 1156789 | |
| n228 | T-box 3 (ulnar mammary syndrome) | 70500 | T48941 | 650801 | NM_005996 |
| | | | T48942 | 650802 | NM_016569 |
| n229 | serine proteinase inhibitor, clade A member 1 | 207735 | H58973 | 1011758 | NM_000295 |
| | | 294578 | H58926 | 1011805 | |
| | | | N71049 | 1227629 | |
| | | | W01726 | 1273926 | |
| n230 | Inositol 1,4,5-triphosphate receptor, type 1 | 683569 | AA215397 | 1815142 | NM_002222 |
| | | 471725 | AA035450 | 1507136 | |
| | | | AA035477 | 1507248 | |
| n231 | Transforming, acidic coiled-coil containing protein 1 | 193182 | H47413 | 923379 | NM_006283 |
| | | 813188 | H47327 | 923465 | |
| | | 898098 | AA456316 | 2179526 | |
| | | | AA456713 | 2179289 | |
| | | | AA598796 | 2432468 | |
| n232 | Inhibitor of kappa light polypeptide gene enhancer in B-cells, kinase beta | 309563 | N94412 | 1266721 | |
| n233 | CDC2-related protein kinase 7 | 823771 | AA490255 | 2219428 | NM_016507 |
| | | 858567 | AA490355 | 2219528 | |
| | | 731231 | AA774159 | 826048 | |
| | | | AA421065 | 099818 | |
| | | | AA420967 | 099880 | |
| n234 | Hydroxyacid oxidase 2 | 1535106 | AA919149 | 3057172 | NM_016527 |
| n235 | Mannosidase, alpha, class 1A, member 1 | 112629 | T91261 | 714050 | NM_005907 |
| | | | | 723174 | |
| n236 | KIAA0523 protein | 50939 | H18630 | 884870 | |
| | | | H18715 | 884955 | |
| n237 | Homo sapiens cDNA FLJ12935 fis, clone NT2RP2004982 | 32962 | R18800 | 772410 | |
| | | | R43910 | 793661 | |

TABLE 2-continued

| Marker | Gene Name | Image Clone ID | Image Clone Accession # | Image Clone GI # | Genbank or RefSeq nuc accession# |
|---|---|---|---|---|---|
| n238 | Unamed | 436431 | AA699632 | 2703779 | |
| n239 | RNA binding motif protein 3 | 380797 | AA054287 | 1545230 | NM_006743 |
| | | | AA054406 | 1545332 | |
| n240 | Unamed | 826109 | AA521327 | 2261870 | |
| n241 | KIAA0367 protein | 813828 | AA447773 | 2161443 | |
| n242 | Unamed | 289534 | N59251 | 1203141 | |
| | | | | 1239297 | |
| n243 | Unamed | 1030936 | AA620340 | 2524279 | |
| n244 | Unamed | 1627636 | AI014709 | 3229090 | |
| n245 | Unamed | 363026 | AA018872 | 1482472 | |
| | | | AA019181 | 1482571 | |
| n246 | Hypothetical protein DKFZp434C0328 | 744939 | AA625897 | 2538284 | NM_017577 |
| n247 | Chromosome 11 open reading frame 14 | 726860 | AA293782 | 1941840 | NM_020645 |
| | | 279963 | AA398356 | 2051465 | |
| | | | N57557 | 1201447 | |
| n248 | Annexin A9 | 239568 | H81304 | 1059393 | NM_003568 |
| | | | H81359 | 1059448 | |
| n249 | Chromosome 8 open reading frame 2 | 269923 | N36315 | 1139044 | NM_007175 |
| | | 432227 | N24894 | 1157457 | |
| | | | AA679448 | 2659970 | |
| n250 | Unamed | 205023 | H57374 | 1010206 | |
| | | | H57423 | 1010255 | |
| n251 | myosin 5C | 665405 | AA195002 | 1784818 | NM_018728 |
| | | | AA194815 | 1784704 | |
| n252 | Hypothetical protein FLJ11155 | 288770 | N79400 | 1210328 | NM_018342 |
| | | | N62499 | 1242101 | |
| n253 | Adipose specific 2 | 740941 | AA478298 | 2206932 | NM_006829 |
| n254 | sorting nexin 9 | 142139 | R69277 | 842680 | NM_016224 |
| | | | R69163 | 842794 | |
| n255 | Unamed | 731035 | AA421468 | 2100293 | |
| | | | AA421499 | 2100324 | |
| n256 | Unamed | 549101 | AA083577 | 1625546 | |
| | | | AA083485 | 1625637 | |
| n257 | Cadherin, EGF LAG seven-pass G-type receptor 2, flamingo (*Drosophila*) homolog | 175103 | H39187 | 908686 | NM_001408 |
| n258 | Unamed | 416280 | W86100 | 1398607 | |
| | | | W86133 | 1398563 | |
| n259 | Unamed | 32925 | R43646 | 774939 | |
| | | | R20305 | 821563 | |
| n260 | Unamed | 298162 | W01408 | 1227371 | |
| | | | N70791 | 1273407 | |
| n261 | solute carrier family 16, member 6 | 266389 | N21654 | 1126824 | NM_004694 |
| n262 | Mitogen-activated protein kinase 3 | 809939 | AA454819 | 2177595 | |
| | | | AA454894 | 2177670 | |
| n263 | Unamed | 241475 | H90421 | 1080851 | |
| | | | H90477 | 1080907 | |
| n264 | KIAA1041 protein | 744388 | AA621197 | 2525136 | NM_014947 |
| n265 | *Homo sapiens* clone TCCCTA00151 mRNA sequence | 767345 | AA418633 | 2080365 | |
| | | 296679 | AA418564 | 2080443 | |
| | | | N74018 | 1231303 | |
| | | | W02256 | 1274254 | |
| n266 | *Homo sapiens* mRNA; cDNA DKFZp761E13121 | 845037 | AA773304 | 2824875 | |
| n267 | KIAA0712 gene product | 1650304 | AI022613 | 3237854 | NM_014715 |
| n268 | Unamed | 486626 | AA044353 | 1522091 | |
| | | | AA044031 | 1522209 | |
| n269 | thyroid hormone receptor-associated protein, 240 kDa subunit | 613070 | AA181646 | 1765080 | NM_005121 |
| | | 837892 | AA434084 | 1765113 | |
| | | 490748 | AA434356 | 2138998 | |
| | | 810948 | AA122297 | 2139270 | |
| | | 138477 | AA122265 | 1678504 | |
| | | | AA459383 | 1678553 | |
| | | | R68631 | 2184290 | |
| | | | | 842147 | |
| | | | | 842148 | |
| n270 | Melanoma antigen recognized by T cells 2 | 359855 | AA010728 | 1471982 | NM_018194 |
| | | | AA011335 | 1472382 | |
| n271 | Hypothetical protein FLJ13322 | 221890 | H85020 | 1064722 | NM_024722 |
| n272 | Docking protein 1, 62 kD | 504673 | AA150646 | 1712321 | NM_001381 |
| | | | AA142943 | 1722158 | |
| n273 | inhibin, beta A | 269815 | N40099 | 1141507 | NM_002192 |
| | | | N27159 | 1163644 | |
| n274 | protein tyrosine phosphatase, receptor type, R | 52079 | H23202 | 891897 | NM_002849 |
| | | | H23315 | 892010 | |

TABLE 2-continued

| Marker | Gene Name | Image Clone ID | Image Clone Accession # | Image Clone GI # | Genbank or RefSeq nuc accession# |
|---|---|---|---|---|---|
| n275 | tumor-associated calcium signal transducer 2 | 809938 | AA454810<br>AA454884 | 2177586<br>2177660 | NM_002353 |
| n276 | proline synthetase co-transcribed | 611373<br>416202<br>418094 | AA176668<br>AA176833<br>W86106<br>W90036<br>W90184 | 1757987<br>1757965<br>1398536<br>1406076<br>1406174 | NM_007198 |
| n277 | Prohibitin | 276519<br>510464 | N48458<br>N39101<br>AA055656<br>AA055712 | 1162308<br>1189624<br>1547995<br>1548050 | NM_002634 |
| n278 | Unamed | 272879 | N33012 | 1153411 | |
| n279 | Unamed | 1641664 | AI016387 | 3230723 | |
| n280 | Glypican 4 | 358217 | W95635<br>W95636 | 1425544<br>1425545 | NM_001448 |
| n281 | Unamed | 1475881 | AA872153 | 2968331 | |
| n282 | keratin 18 | 855521 | AA664179 | 2618170 | NM_000224 |
| n283 | CCR4-NOT transcription complex, subunit 2 | 144042<br>868590 | R77125<br>R77126<br>AA664363 | 851757<br>851758<br>2618354 | NM_014515 |
| n284 | Cystatin C | 949938 | AA599177 | 2432802 | NM_000099 |
| n285 | Prohibitin | 42313 | R60946<br>R61067 | 831641<br>831762 | NM_002634 |
| n286 | Desmoplakin | 135975 | R33557<br>R33456 | 789314<br>789415 | NM_004415 |
| n287 | HSPC041 protein | 549911 | AA082742<br>AA101072 | 1624800<br>1647653 | NM_016099 |
| n288 | KIAA0590 gene product | 810773 | AA481751<br>AA481015 | 2210567<br>2211303 | NM_014714 |
| n289 | Hypothetical protein MGC11321 | 590298 | AA147837<br>AA147874 | 1717209<br>1717264 | NM_032351 |
| n290 | CGI-06 protein | 198960 | H83225<br>H82992 | 1061662<br>1061895 | NM_015937 |
| n291 | Hypothetical protein FLJ10466 | 795229 | AA453607<br>AA454139 | 2167276<br>2167808 | NM_018100 |
| n292 | Hypothetical protein FLJ14299 | 788087 | AA453170 | 2166839 | NM_025069 |
| n293 | Unamed | 884662 | AA629903 | 2552514 | |
| n294 | nuclear mitotic apparatus protein 1 | 897901 | AA598659 | 2432242 | NM_006185 |
| n295 | zinc finger protein 161 | 666377 | AA232647 | 1855649 | NM_007146 |
| n296 | homeo box B6 | 773296 | AA610066 | 2458494 | NM_018952 |
| n297 | Unamed | 810331 | AA464152<br>AA464217 | 2189036<br>2189101 | |
| n298 | CGI-119 protein | 743749 | H78462<br>H78365 | 1056551<br>1056454 | NM_016056 |
| n299 | Carbonic anhydrase XII | 594633 | AA171913<br>AA171613 | 1751034<br>1750817 | NM_001218 |
| n300 | *Homo sapiens* cDNA FLJ12900 | 212542 | H68663<br>H68664 | 1030125<br>1030126 | |
| n301 | Unamed | 1032056 | AA610043 | 2458471 | |
| n302 | *Homo sapiens* cDNA FLJ12900 | 200656 | R98407 | 985119 | |

TABLE 3

| Marker | Gene Name | Image Clone ID | Image Clone Accession # | Image Clone GI# | Genbank or RefSeq nuc accession# |
|---|---|---|---|---|---|
| n303 | *Homo sapiens* mRNA; cDNA DKFZp564A026 | 950479 | AA599122 | 2432747 | |
| n304 | Hypothetical protein from EUROIMAGE 363668 | 743829 | AA634385 | 2557599 | |
| n305 | ataxia-telangiectasia group D-associated protein | 377275 | AA055485<br>AA055486 | 1547824<br>1547825 | NM_012101 |
| n306 | fatty acid desaturase 2 | 878174 | AA775443 | 2834777 | NM_004265 |
| n307 | Moesin | 131362 | R23083<br>R22977 | 777865<br>777971 | NM_002444 |
| n308 | Interleukin-1 receptor-associated kinase 1 | 379200 | AA683550 | 2670148 | NM_001569 |
| n309 | Triosephosphate isomerase 1 | 855749 | AA663983 | 2617974 | NM_000365 |
| n310 | KIAA0179 protein | 845602 | AA644334 | 2569552 | |
| n311 | Hypothetical protein FLJ20005 | 51275 | H18864<br>H18865 | 885104<br>885105 | NM_017617 |

TABLE 3-continued

| Marker | Gene Name | Image Clone ID | Image Clone Accession # | Image Clone GI# | Genbank or RefSeq nuc accession# |
|---|---|---|---|---|---|
| n312 | Guanylate binding protein 1 | 841008 | AA486850<br>AA486849 | 2217013<br>2217014 | NM_002053 |
| n313 | G protein-coupled receptor, family C, group 5, member B | 321580 | W35153<br>W32884 | 1314939<br>1317257 | NM_016235 |
| n314 | Neurocalcin delta | 838478 | AA457611<br>AA457517 | 2180237<br>2180331 | NM_032041 |
| n315 | Preferentially expressed antigen in melanoma | 897956 | AA598817 | 2432489 | NM_006115 |
| n316 | ADP-ribosyltransferase 3 | 1468263 | AA884935 | 2994916 | NM_001179 |
| n317 | CCAAT enhancer binding protein, beta | 161993 | H26183<br>H26184 | 898339 | NM_005194 |
| n318 | Crystallin, alpha B | 839736 | AA504943<br>AA504891 | 2241051<br>2241103 | NM_001885 |
| n319 | nudix -type motif 5 | 824421 | AA490236<br>AA490510 | 2219418<br>2219683 | NM_014142 |
| n320 | Prominin (mouse)-like 1 | 27544 | R40057 | 822754 | NM_006017 |
| n321 | Unamed | 1031919 | AA609749 | 2458177 | |
| n322 | keratin 17 | 1048993 | AA778645 | 2837976 | NM_000422 |
| n323 | Forkhead box M1 | 564803 | AA129552<br>AA136566 | 1689317<br>1697776 | NM_021953 |
| n324 | kangai 1 | 1474284 | AA922309 | 3069618 | NM_002231 |
| n325 | Interferon, gamma-inducible protein 16 | 824602 | AA491191<br>AA490996 | 2220169<br>2220364 | NM_005531 |
| n326 | Argininosuccinate synthetase | 882522<br>882461 | AA676466<br>AA676405 | 2656988<br>2656927 | NM_000050 |
| n327 | profilin 2 | 486110 | AA040703<br>AA043167 | 1517193<br>1521021 | NM_002628 |
| n328 | Unamed | 449112 | AA777488 | 2836967 | |
| n329 | Adenylate kinase 2 | 45464 | H09730<br>H10488 | 874552<br>875310 | NM_001625<br>NM_013411 |
| n330 | Chitinase 3-like 2 | 854338<br>815214 | AA668821<br>AA481250<br>AA481565 | 2630320<br>2210802<br>2211117 | NM_004000 |
| n331 | Nuclease sensitive element binding protein 1 | 949932 | AA599175 | 2432800 | NM_004559 |
| n332 | Hypothetical protein FLJ22530 | 745495 | AA625991 | 2538378 | |
| n333 | gamma-aminobutyric acid A receptor, pi | 563598 | AA102670<br>AA101225 | 1647902<br>1648004 | NM_014211 |
| n334 | Tryptophanyl-tRNA synthetase | 855786 | AA664040 | 2618031 | NM_004184 |
| n335 | Unamed | 487371 | AA046488<br>AA046700 | 1524481<br>1524597 | |
| n336 | Inositol(myo)-1(or 4)-monophosphatase 2 | 32299 | R42685<br>R17337 | 770947<br>819630 | NM_014214 |
| n337 | Glutaminase | 624811 | AA188081<br>AA182001 | 1765502<br>1774274 | NM_014905 |
| n338 | Spi-B transcription factor | 295093 | W01642<br>N71628 | 1228340<br>1273641 | NM_003121 |
| n339 | Lymphocyte antigen 6 complex, locus E | 1470048 | AA865464 | 2957740 | NM_002346 |
| n340 | NGFI-A binding protein 2 | 770868 | AA434487<br>AA434391 | 2139305<br>2139401 | NM_005967 |
| n341 | N-myc downstream-regulated gene 2 | 897252 | AA677640 | 2658162 | NM_016250 |
| n342 | Huntingtin-associated protein interacting protein | 971279 | AA682905 | 2668796 | NM_003947 |
| n343 | Unamed | 825207 | AA504379<br>AA504120 | 2240280<br>2240539 | |
| n344 | Guanylate binding protein 1, interferon-inducible, 67 kD | 712292 | AA280278<br>AA280279 | 1921952<br>1921953 | NM_002053 |
| n345 | early development regulator | 898328 | AA598840 | 2432512 | NM_004427 |
| n346 | type I intermediate filament cytokeratin | 454970 | AA676625 | 2657147 | NM_015515 |
| n347 | PH domain containing protein in retina 1 | 731469<br>447416 | AA412417<br>AA702335 | 2071023<br>2705448 | NM_021200 |
| n348 | Secreted frizzled-related protein 1 | 82225 | T68892<br>T68966 | 680040<br>680114 | NM_003012 |
| n349 | DKFZP586K0524 protein | 785744 | AA448941<br>AA449667 | 2162961<br>2163417 | |
| n350 | Carbohydrate sulfotransferase 2 | 431301 | AA682637 | 2669918 | NM_004267 |
| n351 | Immunoglobulin heavy constant mu | 214441 | H73590<br>H73816 | 1046649<br>1046750 | |
| n352 | Biphenyl hydrolase-like | 877772 | AA626777 | 2539164 | NM_004332 |
| n353 | Complement component 1, s subcomponent | 85634 | T62048 | 665291<br>665355 | NM_001734 |
| n354 | Phosphoribosyl pyrophosphate synthetase-associated protein 1 | 33949 | R20005 | 774639<br>824198 | NM_002766 |
| n355 | ATPase, Na+ | 136722 | R35218<br>R35219 | 792119<br>792120 | NM_001679 |

TABLE 3-continued

| Marker | Gene Name | Image Clone ID | Image Clone Accession # | Image Clone GI# | Genbank or RefSeq nuc accession# |
|---|---|---|---|---|---|
| n356 | Unamed | 1626508 | AA995233 | 3181722 | |
| n357 | small inducible cytokine subfamily A, member 19 | 430465 | AA680186 | 2656653 | NM_006274 |
| n358 | 28 kD interferon responsive protein | 268385 | N35187<br>N23400 | 1137550<br>1156329 | NM_022147 |
| n359 | Homo sapiens cDNA FLJ20201 | 281597 | N53906<br>N51612 | 1192778<br>1195072 | |
| n360 | actin-related protein 3-beta | 726582 | AA394106<br>AA398135 | 2047094<br>2051244 | NM_020445 |
| n361 | Tyrosine 3-monooxygenase | 868396 | AA634164 | 2557378 | NM_003405 |
| n362 | lamin B receptor | 489489 | AA099192<br>AA099136 | 1645023<br>1645080 | NM_002296 |
| n363 | NADH ubiquinone oxidoreductase MLRQ subunit homolog | 415814 | W84778<br>W84825 | 1395898<br>1395955 | NM_020142 |
| n364 | KIAA0173 gene product | 450453 | AA682815 | 2669498 | NM_014640 |
| n365 | tumor necrosis factor (ligand) superfamily, member 13b | 593690 | AA166695 | 1745159 | NM_006573 |
| n366 | Unamed | 969843 | AA663831 | 2617822 | |
| n367 | Unamed | 758309 | AA404269<br>AA401230 | 2055119<br>2058993 | |
| n368 | Hypothetical protein FLJ20940 | 277173 | N44209<br>N34316 | 1155458<br>1182737 | NM_032192 |
| n369 | Hypothetical protein FLJ10430 | 815556 | AA456821 | 2179541 | NM_018092 |
| n370 | Unamed | 970391 | AA776087 | 2835421 | |
| n371 | nuclear factor I | 416959 | W87528<br>W87611 | 1401583<br>1401675 | NM_005596 |
| n372 | ATP-binding cassette, sub-family B | 813256 | AA456377<br>AA455911 | 2178687<br>2178953 | NM_000927 |
| n373 | natural killer cell transcript 4 | 810859 | AA459180<br>AA458965 | 2183872<br>2184087 | NM_004221 |
| n374 | Unamed | 266135 | N21633 | 1126803<br>1147109 | |
| n375 | Frizzled (Drosophila) homolog 8 | 810459 | AA457138 | 2179858 | NM_031866 |
| n376 | high-mobility group protein isoforms I and Y | 782811 | AA448261 | 2161931 | NM_002131 |
| n377 | Ubiquitin specific protease 1 | 489595 | AA099033<br>AA099034 | 1645474<br>1645475 | NM_003368 |
| n378 | Unamed | 786657 | AA451886 | 2165555 | |
| n379 | Complement component 1, r subcomponent | 83549 | T69603<br>T69675 | 680751<br>680823 | NM_001733 |
| n380 | Unamed | 430709 | AA678092 | 2658614 | |
| n381 | Calreticulin | 772913 | AA479920<br>AA428508 | 2112505<br>2204402 | NM_004343 |
| n382 | Cytochrome P450, subfamily I, polypeptide 1 | 782760 | AA448157 | 2161827 | NM_000104 |
| n383 | Peptidylprolyl isomerase B | 756600 | AA481464<br>AA481699 | 2211016<br>2211251 | NM_000942 |
| n384 | Angiopoietin-like 4 | 69002 | T53705<br>T54298 | 655566<br>656159 | NM_016109 |
| n385 | Proteasome subunit, beta type, 9 | 1456118 | AA862434 | 2954913 | NM_002800 |
| n386 | Unamed | 285207 | N66273 | 1218398 | |
| n387 | ataxin-1 ubiquitin-like interacting protein | 767180 | AA424661<br>AA424564 | 2103534<br>2103614 | NM_020131 |
| n388 | Integral membrane protein 2A | 245277 | N72450<br>N53447 | 1194613<br>1229554 | NM_004867 |
| n389 | FYN-binding protein | 293325 | N64862<br>N92106 | 1212691<br>1264415 | NM_001465 |
| n390 | Ribosomal protein L44 | 51078 | H17242<br>H17135 | 883375<br>883482 | NM_021029 |
| n391 | Unamed | 399577 | AA733090 | 2754449 | |
| n392 | fibulin 5 | 50483 | H17615<br>H17726 | 883855<br>883966 | NM_006329 |
| n393 | Phosphodiesterase 7A | 1671124<br>68340 | AI075273<br>T56982<br>T56983 | 3401864<br>658843<br>658844 | |
| n394 | Unamed | 1626808 | AI018277 | 3232796 | |
| n395 | small inducible cytokine subfamily B (Cys-X-Cys), member 10 | 1493160 | AA878880 | 2987845 | NM_001565 |
| n396 | CDC20 | 898062 | AA598776 | 2432448 | NM_001255 |
| n397 | Unamed | 1048601 | AA608870 | 2457298 | |
| n398 | Potassium intermediate | 756708 | AA443903 | 2156578 | NM_002250 |
| n399 | keratin 6B | 366481 | AA026495<br>AA026418 | 1492319<br>1492377 | NM_005555 |
| n400 | Aldehyde dehydrogenase 1 family, member A3 | 814798 | AA455235<br>AA465614 | 2178011<br>2191781 | NM_000693 |

TABLE 3-continued

| Marker | Gene Name | Image Clone ID | Image Clone Accession # | Image Clone GI# | Genbank or RefSeq nuc accession# |
|---|---|---|---|---|---|
| n401 | Homolog of mouse quaking QKI | 843385 | AA489386<br>AA489445 | 2218988<br>2219047 | |
| n402 | Suppression of tumorigenicity 14 | 825085 | AA489246 | 2218848<br>2240477 | NM_021978 |
| n403 | Coatomer protein complex, subunit beta 2 | 278687 | W01400<br>N62924 | 1210753<br>1273380 | NM_004766 |
| n404 | Decidual protein induced by progesterone | 137554<br>245774<br>135811 | R39563<br>R39621<br>N55269<br>N76878<br>R33362<br>R33363 | 797019<br>797077<br>1198148<br>1239456<br>789220<br>789221 | NM_007021 |
| n405 | BTG family, member 3 | 246304 | N52496<br>N74741 | 1193662<br>1232026 | NM_006806 |
| n406 | KIAA1866 protein | 754126 | AA478623<br>AA478880 | 2207257<br>2207514 | |
| n407 | Hypothetical protein MGC 10986 | 344937 | W75960<br>W72885 | 1383020<br>1386334 | NM_030576 |
| n408 | Tetranectin | 345553 | W76174<br>W73889 | 1382284<br>1386418 | NM_003278 |
| n409 | Unamed | 1639103 | AI016824 | 3231160 | |
| n410 | T cell receptor beta locus | 306841 | N91921 | 1264230 | |
| n411 | Hypothetical protein FLJ12770 | 813815 | AA447727<br>AA447889 | 2161397<br>2161559 | NM_032174 |
| n412 | Hypothetical protein FLJ21841 | 347268<br>1470278 | W80898<br>W80791<br>AA866029 | 1391809<br>1391922<br>2958305 | NM_024609 |
| n413 | keratin 5 | 592540 | AA160595<br>AA160507 | 1735874<br>1735963 | NM_000424 |
| n414 | Potassium channel modulatory factor | 752813 | AA436378<br>AA481311 | 2141292<br>2210863 | NM_020122 |
| n415 | pellino (Drosophila) homolog 1 | 416676 | W86504 | 1400251 | NM_020651 |
| n416 | T cell receptor alpha locus | 770014 | AA427667<br>AA427491 | 2111387<br>2111484 | |
| n417 | CD48 antigen | 125134 | R05415 | 756035<br>756036 | NM_001778 |
| n418 | Unamed | 345416 | W76022<br>W72466 | 1382143<br>1386266 | |
| n419 | Interleukin enhancer binding factor 2, 45 kD | 242952 | H95712<br>H95638 | 1108780<br>1108854 | NM_004515 |
| n420 | cDNA for differentially expressed CO16 gene | 782575 | AA447522<br>AA448505 | 2161192<br>2162175 | |
| n421 | Thymopoietin | 454083 | AA676998 | 2657520 | NM_003276 |
| n422 | DKFZP564D0764 protein | 796767 | AA460732<br>AA460904 | 2185852<br>2186024 | |
| n423 | MAD2 (mitotic arrest deficient, yeast, homolog)-like 1 | 814701 | AA481076 | 2210628 | NM_002358 |
| n424 | AD037 protein | 1572070 | AA933056 | 3086989 | NM_032023 |
| n425 | Homo sapiens mRNA; cDNA DKFZp434B0425 | 430186 | AA010188 | 1471215 | |
| n426 | DEK oncogene | 133136 | R28400<br>R25377 | 781512<br>784535 | NM_003472 |
| n427 | c-Cbl-interacting protein | 1604005 | AA989257 | 3173879 | NM_031892 |
| n428 | uridine monophosphate kinase | 344243 | W69906<br>W70171 | 1379374<br>1379432 | NM_012474 |
| n429 | Progesterone receptor membrane component 1 | 41698 | R59281<br>R59221 | 829916<br>829976 | NM_006667 |
| n430 | Diubiquitin | 243741 | N49629<br>N33920 | 1154320<br>1190795 | NM_006398 |
| n431 | Transcription factor 19 | 416075 | W85878<br>W85962 | 1398307<br>1398390 | NM_007109 |
| n432 | KIAA1089 protein | 770709 | AA476305<br>AA433827 | 2138741<br>2204516 | |
| n433 | D123 gene product | 784830 | AA448289 | 2161959 | NM_006023 |
| n434 | Macrophage receptor with collagenous structure | 840466 | AA485867<br>AA487769 | 2215086<br>2215200 | NM_006770 |
| n435 | Hypothetical protein FLJ20624 | 784016 | AA443698 | 2115617<br>2156373 | NM_017906 |
| n436 | matrix metalloproteinase 7 | 470393 | AA031514<br>AA031513 | 1501467<br>1501468 | NM_002423 |
| n437 | scrapie responsive protein 1 | 796148 | AA460975 | 2186095 | NM_007281 |
| n438 | Carboxypeptidase, vitellogenic-like | 39833 | R53455 | 815357 | NM_031311 |
| n439 | Integral membrane protein 3 | 471196 | AA034213 | 1506023 | NM_030926 |
| n440 | Sialyltransferase 1 | 897906 | AA598652 | 2432235 | NM_003032 |
| n441 | Ectonucleotide pyrophosphatase | 430968 | AA678335 | 2658857 | NM_005021 |

TABLE 3-continued

| Marker | Gene Name | Image Clone ID | Image Clone Accession # | Image Clone GI# | Genbank or RefSeq nuc accession# |
|---|---|---|---|---|---|
| n442 | Interleukin 16 | 809776 | AA454784 | 2177508 | NM_004513 |
|  |  |  | AA454732 | 2177560 |  |
| n443 | Unamed | 80186 | T64192 | 668057 |  |
|  |  |  | T64380 | 668245 |  |
| n444 | CD3D antigen | 377560 | AA055945 | 1548284 | NM_000732 |
|  |  |  | AA055946 | 1548285 |  |
| n445 | major histocompatibility complex, class II, DR alpha | 153411 | R48091 | 810005 | NM_019111 |
|  |  |  | R47979 | 810117 |  |
| n446 | Lymphotoxin beta | 1946534 | AI351740 | 4088946 | NM_002341 |
|  |  |  |  |  | NM_009588 |
| n447 | KIAA0535 gene product | 1910316 | AI350226 | 4087432 | NM_014682 |
| n448 | TATA box binding protein | 280735 | N50603 | 1191715 | NM_003194 |
|  |  |  | N50549 | 1191769 |  |
| n449 | Hypothetical protein MGC5363 | 502910 | AA128571 | 1688423 | NM_024064 |
|  |  |  | AA128274 | 1688524 |  |
| n450 | Wingless-type MMTV integration site family, member 6 | 687972 | AA236986 | 1860367 |  |
|  |  |  | AA235928 | 1861014 |  |
| n451 | Mitogen-activated protein kinase kinase 6 | 45578 | H07920 | 872742 | NM_002758 |
|  |  |  | H08016 | 872838 | NM_031988 |
| n452 | Microfibrillar-associated protein 2 | 291880 | W03413 | 1219612 | NM_002403 |
|  |  |  | N67487 | 1275326 | NM_017459 |
| n453 | Unamed | 503051 | AA151535 | 1719966 |  |
|  |  |  | AA149250 | 1720022 |  |
| n454 | Adipose differentiation-related protein | 435036 | AA700054 | 2703017 | NM_001122 |
| n455 | Unamed | 825654 | AA505050 | 2241210 |  |
|  |  |  |  | 2241211 |  |
| n456 | Chitinase 3-like 1 | 770212 | AA434048 | 2138962 | NM_001276 |
|  |  |  | AA434115 | 2139029 |  |
| n457 | fatty-acid-Coenzyme A ligase, long-chain 2 | 2014138 | AI361530 | 4113516 | NM_021122 |
|  |  | 82734 | T73651 | 690231 |  |
|  |  |  | T73556 | 690326 |  |
| n458 | tumor necrosis factor receptor superfamily, member 7 | 34637 | R45026 | 779904 | NM_001242 |
|  |  |  |  | 823385 |  |
| n459 | Unamed | 399421 | AA733177 | 2754536 |  |
| n460 | zinc finger protein, subfamily 1A, 1 | 447171 | AA702985 | 2706098 | NM_006060 |
| n461 | Ceruloplasmin | 223350 | H86642 | 1068133 | NM_000096 |
|  |  |  | H86554 | 1068221 |  |
| n462 | Transcription factor-like 1 | 757165 | AA444129 | 2156625 | NM_005997 |
|  |  |  | AA443950 | 2156804 |  |
| n463 | CD37 antigen | 824384 | AA489700 | 2219302 | NM_001774 |
| n464 | RNA helicase | 511633 | AA126958 | 1686410 | NM_014314 |
|  |  |  | AA127167 | 1686512 |  |
| n465 | Thrombopoietin | 754034 | AA480029 | 2207614 | NM_000460 |
|  |  |  | AA479058 | 2208180 |  |
| n466 | Unamed | 342740 | W68630 | 1377498 |  |
|  |  |  | W68629 | 1377499 |  |
| n467 | RNA binding motif protein, X chromosome | 133236 | R26929 | 782841 | NM_002139 |
|  |  |  | R26706 | 783064 |  |
| n468 | ets variant gene 6 | 1590021 | AA983191 | 3161716 | NM_001987 |
| n469 | CD79B antigen | 155717 | R72079 | 846111 | NM_000626 |
|  |  |  | R72128 | 846160 | NM_021602 |
| n470 | Chromosome 1 open reading frame 2 | 47665 | H11464 | 876284 | NM_006589 |
|  |  |  | H11572 | 876392 |  |
| n471 | Trinucleotide repeat containing 3 | 199367 | R95691 | 981351 | NM_005878 |
| n472 | Melanoma antigen, family A, 3 | 1631546 | AA995045 | 3181534 | NM_005362 |
| n473 | Retinoic acid receptor responder 1 | 2028617 | AI261360 | 3869563 | NM_002888 |
|  |  | 309583 | W30772 | 1266733 |  |
|  |  |  | N94424 | 1311763 |  |
| n474 | Hypothetical protein DKFZp762N0610 | 1635186 | AI005042 | 3214552 |  |
|  |  | 202919 | H54093 | 994240 |  |
|  |  |  | H54094 | 994241 |  |
| n475 | Isopentenyl-diphosphate delta isomerase | 267176 | N31862 | 1138111 | NM_004508 |
|  |  |  | N23961 | 1152261 |  |
| n476 | 3-hydroxy-3-methylglutaryl-Coenzyme A synthase 2 | 757222 | AA496148 | 2229469 | NM_005518 |
|  |  |  | AA496149 | 2229470 |  |
| n477 | Lipopolysaccharide-binding protein | 66437 | R16098 | 767979 | NM_004139 |
|  |  |  | R15731 | 767907 |  |
| n478 | jun D proto-oncogene | 491403 | AA156585 | 1721929 | NM_005354 |
|  |  |  | AA150416 | 1728227 |  |
| n479 | Src-like-adapter | 815774 | AA485141 | 2214360 | NM_006748 |
| n480 | Sjogren syndrome antigen A1 | 282956 | N45131 | 1186297 | NM_003141 |
| n481 | Hypothetical protein FLJ23563 | 306066 | N91003 | 1444330 |  |
|  |  |  | W20132 | 1296002 |  |
| n482 | Alkaline phosphatase, liver, bone kidney | 1475595 | AA873885 | 2968021 | NM_000478 |

TABLE 3-continued

| Marker | Gene Name | Image Clone ID | Image Clone Accession # | Image Clone GI# | Genbank or RefSeq nuc accession# |
|---|---|---|---|---|---|
| n483 | GS1999full | 161484 | H25560 | 894683 | NM_032564 |
|  |  |  | H25606 | 894729 |  |
| n484 | kinesin family member C3 | 753038 | AA436460 | 2141374 | NM_005550 |
|  |  |  | AA436508 | 2141422 |  |
| n485 | Protoporphyrinogen oxidase | 504452 | AA151249 | 1719439 | NM_000309 |
|  |  |  | AA151248 | 1719440 |  |
| n486 | fatty acid binding protein 5 | 2012523 | AI359037 | 4110658 | NM_001444 |
|  |  | 281039 | N47717 | 1188882 |  |
|  |  |  |  | 1188883 |  |
| n487 | HSPC182 protein | 450213 | AA703536 | 2713454 | NM_014188 |
| n488 | NCK adaptor protein 1 | 712683 | AA280214 | 1921815 | NM_006153 |
|  |  | 302369 | AA280548 | 1924658 |  |
|  |  |  | W16804 | 1443464 |  |
|  |  |  | N90137 | 1291201 |  |
| n489 | Hypothetical protein FLJ12389 similar to acetoacetyl-CoA synthetase | 153830 | R48370 | 810296 | NM_023928 |
|  |  |  | R48270 | 810396 |  |
| n490 | Guanylate cyclase 1, soluble, alpha 3 | 51011 | H19241 | 885481 | NM_000856 |
|  |  | 51749 | H19242 | 885482 |  |
|  |  |  | H23049 | 891744 |  |
|  |  |  | H24329 | 893024 |  |
| n491 | CD19 antigen | 2027587 | AI356451 | 4108072 | NM_001770 |
| n492 | Ubiquitin specific protease 21 | 183062 | H42874 | 918926 | NM_016572 |
|  |  |  | H42938 | 918990 | NM_012475 |
| n493 | small inducible cytokine subfamily D (Cys-X3-Cys), member 1 | 140574 | R66139 | 838777 | NM_002996 |
|  |  | 161923 | R67753 | 840391 |  |
|  |  |  | H26022 | 895145 |  |
|  |  |  | H26069 | 895192 |  |
| n494 | linker for activation of T cells | 346360 | W74254 | 1384502 | NM_014387 |
|  |  |  |  | 1390481 |  |
| n495 | CDK2-associated protein 1 | 144932 | R78607 | 854888 | NM_004642 |
|  |  |  | R78608 | 854889 |  |
| n496 | Unamed | 767164 | AA424653 | 2103526 |  |
|  |  |  | AA424556 | 2103606 |  |
| n497 | claudin 1 | 664975 | AA194833 | 1784523 | NM_021101 |
| n498 | proline arginine-rich end leucine-rich repeat protein | 837870 | AA434067 | 2138981 | NM_002725 |
|  |  |  | AA434342 | 2139256 |  |
| n499 | Membrane metallo-endopeptidase | 200814 | R98851 | 985452 | NM_000902 |
|  |  |  | R98936 | 985537 | NM_007287 |
|  |  |  |  |  | NM_007288 |
|  |  |  |  |  | NM_007289 |
| n500 | Methylcrotonoyl-Coenzyme A carboxylase 1 | 490649 | AA101777 | 1648774 | NM_020166 |
|  |  |  | AA101775 | 1648775 |  |
| n501 | TATA-binding protein-binding protein | 814562 | AA480876 | 2210428 | NM_013375 |
|  |  |  | AA480934 | 2210486 |  |
| n502 | Unamed | 753019 | AA436575 | 2141462 |  |
|  |  |  | AA436548 | 2141489 |  |
| n503 | Unamed | 729924 | AA399633 | 2052647 |  |
| n504 | Amyloid beta (A4) precursor protein (protease nexin-II, Alzheimer disease) | 856575 | AA633658 | 2556872 | NM_000484 |
| n505 | Apoptosis regulator BCL-G | 1049216 | AA620708 | 2524647 | NM_030766 |
| n506 | Kallikrein 6 | 809784 | AA454794 | 2177519 | NM_002774 |
|  |  |  | AA454743 | 2177570 |  |
| n507 | tumor necrosis factor, alpha-induced protein 6 | 357031 | W92764 | 1422204 | NM_007115 |
|  |  |  | W93163 | 1422316 |  |
| n508 | BUB3 | 785778 | AA448967 | 2162987 | NM_004725 |
|  |  |  | AA449693 | 2163443 |  |
| n509 | Unamed | 512605 | AA062659 | 1556882 |  |
| n510 | Transcriptional co-activator with PDZ-binding motif (TAZ) | 589869 | AA148213 | 1717719 | NM_015472 |
| n511 | ! unamed | 156962 | R74321 | 848691 |  |
|  |  |  | R74415 | 848785 |  |
| n512 | *Homo sapiens* mRNA; cDNA DKFZp564H1916 | 813265 | AA455935 | 2178711 |  |
|  |  |  | AA456404 | 2178980 |  |
| n513 | CD22 antigen | 284220 | N53534 | 1194700 | NM_001771 |
| n514 | Hypothetical protein PRO0823 | 1486194 | AA936866 | 3094900 |  |
| n515 | Unamed | 824986 | AA489171 | 2218692 |  |
|  |  |  |  | 2218773 |  |
| n516 | Unamed | 648025 | AA206915 | 1802607 |  |
|  |  |  | AA204757 | 1802492 |  |
| n517 | signal transducer and activator of transcription 1, 91 kD | 840691 | AA488075 | 2215173 | NM_007315 |
|  |  |  | AA486367 | 2215506 |  |
| n518 | Hypothetical protein DKFZp566J091 | 854678 | AA630084 | 2552695 | NM_030915 |
| n519 | Proteasome 26S subunit, non-ATPase, 3 | 815861 | AA485051 | 2214270 | NM_002809 |
|  |  |  |  | 2214271 |  |

TABLE 3-continued

| Marker | Gene Name | Image Clone ID | Image Clone Accession # | Image Clone GI# | Genbank or RefSeq nuc accession# |
|---|---|---|---|---|---|
| n520 | UDP-Gal betaGlcNAc beta 1,4-galactosyltransferase, polypeptide 5 | 825641 | AA504652 AA504750 | 2240812 2240910 | NM_004776 |
| n521 | Unamed | 1500438 | AI733090 AA887255 | 5054203 5339299 | |
| n522 | zinc finger protein 313 | 25071 825697 | R38967 T80323 AA504825 | 796423 698832 2240985 | NM_018683 |
| n523 | Unamed | 1626765 | AI018248 | 3232767 | |
| n524 | beta-1,3-glucuronyltransferase 1 | 290030 | N64656 N80090 | 1212485 1242791 | NM_018644 |
| n525 | Complement component (3d | 826984 | AA521362 | 2261905 | NM_001877 |
| n526 | Hypothetical protein PP591 | 745606 23759 | AA626336 T77100 R38171 | 2538723 795627 694303 | NM_025207 |
| n527 | SELENOPHOSPHATE SYNTHETASE | 840702 | AA486372 AA488081 | 2215178 2215512 | NM_012247 |
| n528 | DKFZP434F2021 protein | 773430 | AA426041 AA428076 | 2106529 2111769 | |
| n529 | Isopentenyl-diphosphate delta isomerase | 44975 | H08820 H08899 | 873642 873721 | NM_004508 |
| n530 | RBP1-like protein | 782618 | AA447551 | 2161221 2162203 | NM_031371 |
| n531 | elastin | 810934 | AA459539 AA459308 | 2184215 2184446 | NM_000501 |
| n532 | cyclin F | 455128 | AA676797 | 2657319 | NM_001761 |
| n533 | fatty acid binding protein 7, brain | 279195 345626 | N46862 N47182 W76403 W72051 | 1188028 1188348 1382321 1386627 | NM_001446 |
| n534 | Unamed | 246329 | N52506 N74750 | 1193672 1232035 | |
| n535 | Hypothetical protein FLJ11181 | 139957 | R64048 R63948 | 835827 835927 | NM_018350 |
| n536 | Anaphase promoting complex subunit 5 | 823954 | AA491011 | 2220016 2220184 | NM_016237 |
| n537 | Neurexin 1 | 32573 | R43532 R20413 | 775047 821461 | NM_004801 |
| n538 | Hypothetical protein PRO2521 | 244062 | N45441 N38810 | 1162017 1186607 | NM_018530 |
| n539 | Ubiquitin-conjugating enzyme E2L 3 | 853988 | AA669526 | 2631025 | NM_003347 |
| n540 | Wnt inhibitory factor-1 | 1504628 | AA897696 | 3034310 | NM_007191 |
| n541 | Farnesyl-diphosphate farnesyltransferase 1 | 866882 | AA679352 | 2659874 | NM_004462 |
| n542 | *Homo sapiens* clone IMAGE 38177 | 47036 | H10956 H10957 | 875776 875777 | |
| n543 | Melanoma antigen, family A, 4 | 1475476 | AA857809 | 2946111 | NM_002362 |
| n544 | PP3111 protein | 950409 | AA599073 | 2432698 | NM_022156 |
| n545 | Ubiquitin-conjugating enzyme E2L 6 | 725395 | AA292074 AA292031 | 1940152 1940060 | NM_004223 |
| n546 | KIAA0740 gene product | 624379 | AA187789 AA182796 | 1766505 1773983 | |
| n547 | nogo receptor | 770989 | AA428418 AA427404 | 2112171 2112232 | NM_023004 |
| n548 | Hypothetical protein FLJ22693 | 205497 | H59985 | 1010689 1012817 | NM_022750 |
| n549 | H4 histone family, member H | 447715 | AA702781 | 2705894 | NM_003543 |
| n550 | Unamed | 1031917 | AA609748 | 2458176 | |
| n551 | Phosphatidylinositol 4-kinase, catalytic, beta polypeptide | 782692 | AA447595 AA448094 | 2161265 2161764 | NM_002651 |
| n552 | Hypothetical protein DKFZp762A227 | 725152 | AA404709 AA404310 | 2059052 2058912 | |
| n553 | Hypothetical protein FLJ22757 | 826242 | AA521476 | 2262019 | NM_024898 |
| n554 | Hypothetical protein MGC16291 | 324593 | W46954 W46955 | 1331662 1331663 | NM_032770 |
| n555 | sterol regulatory element binding transcription factor 2 | 435551 | AA701914 | 2705027 | NM_004599 |
| n556 | S100 calcium-binding protein A1 | 756931 | AA428803 | 2107722 2110354 | NM_006271 |
| n557 | UDP-N-acetyl-alpha-D-galactosamine-galactosylglucosylceramide N-acetylgalactosaminyltransferase | 125092 | R05278 R05336 | 755898 755956 | NM_001478 |
| n558 | dopa decarboxylase | 384015 | AA702640 | 2705753 | NM_000790 |
| n559 | Interleukin 8 | 549933 | AA102526 AA082747 | 1624805 1647657 | NM_000584 |

TABLE 3-continued

| Marker | Gene Name | Image Clone ID | Image Clone Accession # | Image Clone GI# | Genbank or RefSeq nuc accession# |
|---|---|---|---|---|---|
| n560 | Ankyrin 1, erythrocytic | 810625 | AA464755 | 2188933 | NM_000037 |
| | | | AA464049 | 2189639 | NM_020475 |
| | | | | | NM_020476 |
| | | | | | NM_020477 |
| | | | | | NM_020478 |
| | | | | | NM_020479 |
| | | | | | NM_020480 |
| | | | | | NM_020481 |
| n561 | Kallikrein 5 | 344588 | W73168 | 1383275 | NM_012427 |
| | | | W73140 | 1383322 | |
| n562 | Glutamate receptor, ionotropic, N-methyl D-aspartate 2C | 179163 | H50114 | 989955 | NM_000835 |
| | | | H50161 | 990002 | |
| n563 | Unamed | 731025 | AA421267 | 2100092 | |
| | | | AA421314 | 2100190 | |
| n564 | Cadherin, EGF LAG seven-pass G-type receptor 3, flamingo (*Drosophila*) homolog | 754653 | AA411204 | 2068754 | NM_001407 |
| n565 | Unamed | 470148 | AA029867 | 1496718 | |
| | | | AA029314 | 1496094 | |
| n566 | *Homo sapiens* cDNA FLJ21600 fis, clone COL07202 | 277545 | N47366 | 1188532 | |
| | | | N56982 | 1200872 | |
| n567 | Unamed | 159725 | H23963 | 892658 | |
| n568 | Thioredoxin peroxidase | 795543 | AA459663 | 2184570 | NM_006406 |
| n569 | Kynureninase | 1456405 | AA862985 | 2955464 | NM_003937 |
| | | 252515 | AI791358 | 5339074 | |
| | | | AI732962 | 1069050 | |
| | | | H87471 | 1069162 | |
| | | | H87583 | | |
| n570 | Secretagogin | 845521 | AA644563 | 2569781 | NM_006998 |
| n571 | Unamed | 183281 | H43974 | 920026 | |
| | | | H43975 | 920027 | |
| n572 | Unamed | 594585 | AA169633 | 1748263 | |
| | | | AA171675 | 1750742 | |
| n573 | Kallikrein 10 | 809616 | AA458489 | 2183396 | NM_002776 |
| | | 810960 | AA459401 | 2184308 | |
| | | | AA459626 | 2184533 | |
| n574 | Unamed | 1541820 | AA928128 | 3077284 | |
| n575 | Unamed | 898133 | AA598500 | 2432083 | |
| n576 | Apolipoprotein D | 159608 | H15842 | 880662 | NM_001647 |
| | | 838611 | H16152 | 880972 | |
| | | | AA457084 | 2179695 | |
| | | | AA456975 | 2179804 | |
| n577 | Ornithine decarboxylase 1 | 796646 | AA460115 | 2185500 | NM_002539 |
| | | | AA461467 | 2185331 | |
| n578 | Unamed | 199585 | R96499 | 982159 | |
| | | | | 982204 | |
| n579 | *Homo sapiens* clone 25012 | 306933 | N79081 | 1241782 | |
| n580 | *Homo sapiens* clone MGC 9740 IMAGE 3853707 | 129128 | R10885 | 763620 | |
| | | | R10935 | 763670 | |
| n581 | Unamed | 417393 | W89059 | 1403848 | |
| | | | | 1403945 | |
| n582 | protein phosphatase 2, regulatory subunit B, beta isoform | 586725 | AA129170 | 1688954 | NM_006244 |
| | | | AA129171 | 1688955 | |
| n583 | Mitogen-activated protein kinase kinase 1 interacting protein 1 | 305325 | W19601 | 1267236 | NM_021970 |
| | | | N94746 | 1295519 | |
| n584 | Unamed | 1639660 | AI024950 | 3240563 | |
| n585 | Unamed | 175302 | H40290 | 916342 | |
| n586 | protein kinase, X-linked | 1032170 | AA778448 | 2837779 | NM_005044 |
| | | 1638550 | AI016760 | 3231096 | |
| | | 1869486 | AI264246 | 3872449 | |
| n587 | Hydroxyprostaglandin dehydrogenase 15-(NAD) | 868838 | AA775223 | 2834557 | NM_000860 |
| n588 | Forkhead box C1 | 253733 | N75774 | 1128686 | NM_001453 |
| | | 358885 | N22552 | 1238352 | |
| | | | W94714 | 1423751 | |
| | | | W94629 | 1423854 | |
| n589 | *Homo sapiens* clone 24468 | 48330 | H14948 | 879768 | |
| | | | H14949 | 879769 | |
| n590 | CD69 antigen | 704459 | AA279755 | 1921238 | NM_001781 |
| | | | AA279883 | 1921348 | |
| n591 | Amyloid beta (A4) precursor protein-binding, family A, member 1 (XII) | 172751 | H19686 | 888381 | NM_001163 |
| | | | H19687 | 888382 | |
| n592 | similar to rat nuclear ubiquitous casein kinase 2 | 591095 | AA158345 | 1733156 | NM_022731 |
| | | | AA158346 | 1733157 | |
| n593 | Unamed | 1049168 | AA620669 | 2524608 | |

TABLE 3-continued

| Marker | Gene Name | Image Clone ID | Image Clone Accession # | Image Clone GI# | Genbank or RefSeq nuc accession# |
|---|---|---|---|---|---|
| n594 | MDS024 protein | 787893 | AA452404 | 2165840 | NM_021820 |
|  |  |  | AA452171 | 2166073 |  |
| n595 | DKFZP434O125 protein | 240208 | H79705 | 1057794 |  |
|  |  |  | H79706 | 1057795 |  |
| n596 | DKFZP566D193 protein | 782383 | AA431812 | 2115115 |  |
|  |  |  | AA431407 | 2115520 |  |
| n597 | src homology three and cysteine rich domain | 470379 | AA031398 | 1501239 | NM_003149 |
|  |  |  | AA031284 | 1501359 |  |
| n598 | CDC-like kinase 3 | 854645 | AA630459 | 2553070 | NM_003992 |
|  |  |  |  |  | NM_001292 |
| n599 | Annexin A8 | 461307 | AA699870 | 2702833 | NM_001630 |
| n600 | Proteasome 26S subunit, non-ATPase, 2 | 809992 | AA455193 | 2177628 | NM_002808 |
|  |  |  | AA454852 | 2177969 |  |
| n601 | Unamed | 796519 | AA460254 | 2185070 |  |
|  |  |  |  | 2188702 |  |
| n602 | Desmoplakin | 512751 | AA062688 | 1557065 | NM_004415 |
| n603 | kraken-like | 35575 | R45964 | 823208 | NM_014509 |
| n604 | SAM domain and HD domain, 1 | 739094 | AA421603 | 2100601 | NM_015474 |
| n605 | F-box only protein 2 | 179269 | H50245 | 990086 | NM_012168 |
|  |  |  | H50284 | 990125 |  |
| n606 | Unamed | 306726 | W23921 | 1264177 |  |
|  |  |  | N91868 | 1300804 |  |
| n607 | Unamed | 243347 | N38960 | 1162167 |  |
|  |  |  |  | 1189272 |  |
| n608 | Nucleolar protein 1 | 280970 | N50854 | 1192020 | NM_006170 |
| n609 | Coronin, actin-binding protein, 1A | 487988 | AA047478 | 1525652 | NM_007074 |
|  |  |  | AA047477 | 1525653 |  |
| n610 | Unamed | 147987 | R82024 | 858627 |  |
|  |  |  | R82071 | 858674 |  |
| n611 | Human clone 23564 mRNA sequence | 305481 | N89812 | 1443139 |  |
| n612 | uveal autoantigen with coiled-coil domains and ankyrin repeats | 71312 | T47624 | 649604 |  |
|  |  |  | T47625 | 649605 |  |
| n613 | Interleukin 7 receptor | 840460 | AA487767 | 2215084 | NM_002185 |
|  |  | 841238 | AA485865 | 2215198 |  |
| n614 | Succinate dehydrogenase complex, subunit A, flavoprotein | 80915 | T70043 | 681191 | NM_004168 |
|  |  |  | T70109 | 681257 |  |
| n615 | KIAA0293 protein | 32697 | R43605 | 821525 |  |
| n616 | Hypothetical protein MGC5350 | 1637791 | AI002036 | 3202073 | NM_030920 |
|  |  | 856388 | AA774678 | 2834012 |  |
|  |  | 587992 | AA130595 | 1692017 |  |
|  |  |  | AA130596 | 1692018 |  |
| n617 | Neuropilin 1 | 489535 | AA098867 | 1645051 | NM_003873 |
|  |  |  | AA099262 | 1645108 |  |
| n618 | growth factor receptor-bound protein 7 | 236059 | H53702 | 993849 | NM_005310 |
|  |  |  | H53703 | 993850 |  |
| n619 | Synaptic vesicle protein 2B homolog | 39933 | R53963 | 815263 | NM_014848 |
|  |  |  | R53361 | 815865 |  |
| n620 | Hypothetical protein FLJ13154 | 1536236 | AA923560 | 3070869 | NM_024598 |
| n621 | Vascular cell adhesion molecule 1 | 44477 | H07072 | 870603 | NM_001078 |
|  |  | 49164 | H07071 | 870604 |  |
|  |  |  | H16591 | 882816 |  |
|  |  |  | H16637 | 882877 |  |
| n622 | Hypothetical protein FLJ21324 | 781442 | AA428603 | 2112796 | NM_021941 |
|  |  | 192593 | AA432306 | 2114689 |  |
|  |  | 25360 | H41496 | 917548 |  |
|  |  |  | R15074 | 764876 |  |
|  |  |  | R12141 | 769347 |  |
| n623 | PBX | 121406 | T96688 | 735312 | NM_004571 |
|  |  |  | T96804 | 735428 |  |
| n624 | v-kit Hardy-Zuckerman 4 feline sarcoma viral oncogene homolog | 265060 | N20798 | 1125979 | NM_000222 |
|  |  |  |  | 1149037 |  |
| n625 | B-cell CLL | 46452 | H09835 | 874570 | NM_022898 |
|  |  |  | H09748 | 874657 |  |
| n626 | H2A histone family, member O | 488964 | AA057146 | 1525296 | NM_003516 |
|  |  |  | AA047260 | 1549730 |  |
| n627 | *Homo sapiens*, Similar to KIAA0626 gene product, clone MGC 5129 IMAGE 3458716 | 124320 | R02095 | 751831 |  |
|  |  |  | R02208 | 751944 |  |
| n628 | *Homo sapiens* Chromosome 16 BAC clone CIT987SK-A-923A4 | 1553550 | AA962431 | 3134595 |  |
| n629 | EST | 773279 | AA425295 | 2106105 |  |
|  |  |  |  | 2106276 |  |
| n630 | Proteasome 26S subunit, non-ATPase, 10 | 143997 | R77104 | 851736 | NM_002814 |
|  |  |  | R77105 | 851737 |  |

TABLE 3-continued

| Marker | Gene Name | Image Clone ID | Image Clone Accession # | Image Clone GI# | Genbank or RefSeq nuc accession# |
|---|---|---|---|---|---|
| n631 | signal recognition particle 68 kD | 814791 | AA455242<br>AA465622 | 2178018<br>2191789 | NM_014230 |
| n632 | Hypothetical protein FLJ21963 | 22389 | T74065<br>T87224 | 690740<br>715576 | NM_024560 |
| n633 | Neurotrophic tyrosine kinase, receptor, type 2 | 289428 | N79625<br>N63949 | 1211778<br>1242326 | NM_006180 |
| n634 | Cystatin A | 345957 | W72207<br>W77844 | 1382656<br>1388378 | NM_005213 |
| n635 | Hypothetical protein FLJ22995 | 271421 | N34786 | 1155928 | NM_024831 |
| n636 | Cathepsin C | 845355 | AA644088 | 2569306 | NM_001814 |
| n637 | T-cell leukemia | 151531<br>200018 | H03864<br>R97095<br>R97143 | 866796<br>866797<br>982755<br>982803 | NM_020550<br>NM_020552<br>NM_020553<br>NM_020554<br>NM_012468<br>NM_014418 |
| n638 | gene near HD on 4p16.3 with homology to hypothetical *S. pombe* gene | 433256 | AA699419 | 2702613 | |
| n639 | Unamed | 566383 | AA151775 | 1720726<br>1720675 | |
| n640 | *Homo sapiens* mRNA for FLJ00074 protein | 752837 | AA481320<br>AA436384 | 2141298<br>2210872 | |
| n641 | Unamed | 51496 | H19366<br>H18927 | 885167<br>888061 | |
| n642 | Hypothetical protein FLJ13732 similar to tensin | 84560 | T74023<br>T74394 | 690698<br>691069 | NM_022748 |
| n643 | Procollagen-lysine, 2-oxoglutarate 5-dioxygenase | 771323 | AA476240<br>AA476241 | 2204451<br>2204452 | NM_000302 |
| n644 | Unamed | 855707 | AA663941 | 2617932 | |
| n645 | *Homo sapiens*, clone IMAGE 3457003 | 713031 | AA282712<br>AA282599 | 1925515<br>1925638 | |
| n646 | catenin, alpha 2 | 27270 | R18894<br>R37305 | 772504<br>794761 | NM_004389 |
| n647 | Phosphatidylinositol-4-phosphate 5-kinase, type I, beta | 24918 | R39069 | 796525 | NM_003558 |
| n648 | CGI-49 protein | 1630934 | AI018497 | 3233016 | NM_016002 |
| n649 | S-adenosylmethionine decarboxylase 1 | 773204 | AA425692 | 2106412<br>2112539 | NM_001634 |
| n650 | Ribosomal protein S29 | 307119 | W21102<br>N93715 | 1266024<br>1297998 | NM_001032 |
| n651 | Pleckstrin homology, Sec7 and coiled | 33293 | R18844<br>R43956 | 772454<br>821833 | NM_013385 |
| n652 | zinc finger protein | 471200 | AA034215<br>AA033532 | 1505378<br>1506025 | NM_015871 |
| n653 | *Homo sapiens* clone IMAGE 121687 | 121687 | T97580<br>T97628 | 746925<br>746973 | |
| n654 | Lymphocyte-specific protein tyrosine kinase | 730410 | AA469965<br>AA420981 | 2099922<br>2197274 | NM_005356 |
| n655 | FK506-binding protein 5 | 416833 | W86653<br>W87312 | 1400529<br>1401377 | NM_004117 |
| n656 | mature T-cell proliferation 1 | 470175 | AA029308<br>AA029842 | 1496741<br>1496115 | NM_014221 |
| n657 | fatty acid binding protein 6, ileal | 1916019 | AI311734 | 4006605 | NM_001445 |
| n658 | nudix (nucleoside diphosphate linked moiety X)-type motif 9 | 845352 | AA644080 | 2569298 | NM_024047 |
| n659 | Cytochrome P450, subfamily IIB, polypeptide 7 | 1631209 | AA994287 | 3180832 | |
| n660 | Mesothelin | 843028 | AA488406<br>AA488541 | 2215837<br>2215972 | NM_013404<br>NM_005823 |
| n661 | serum amyloid A1 | 161456 | H25590<br>H25546 | 894669<br>894713 | NM_000331 |
| n662 | retinal short-chain dehydrogenase | 300276 | W07107<br>N79745 | 1242446<br>1281264 | NM_016245 |
| n663 | Interferon-related developmental regulator 1 | 882483<br>121948 | AA676598<br>T97868<br>T97762 | 2657120<br>747107<br>747213 | NM_001550 |
| n664 | Unamed | 824523 | AA490900 | 2220073 | |
| n665 | Cytochrome P450, subfamily IIB, polypeptide 6 | 83231 | T68351<br>T68287 | 679435<br>679499 | NM_000767 |
| n666 | Unamed | 544639 | AA074677<br>AA075299 | 1614604<br>1615170 | |
| n667 | Hypothetical protein, expressed in osteoblast | 754479 | AA410188<br>AA410567 | 2069284<br>2069673 | NM_006820 |

TABLE 3-continued

| Marker | Gene Name | Image Clone ID | Image Clone Accession # | Image Clone GI# | Genbank or RefSeq nuc accession# |
|---|---|---|---|---|---|
| n668 | Microfibrillar-associated protein 4 | 759163 | AA442695 | 2154573 | |
| | | | AA496022 | 2229343 | |
| n669 | Unamed | 462939 | AA682419 | 2669700 | |
| n670 | *Homo sapiens* cDNA FLJ20993 | 431284 | AA682626 | 2669907 | |
| n671 | Unamed | 839580 | AA489935 | 2220688 | |
| | | | AA489804 | 2220810 | |
| n672 | Hypothetical protein MGC2452 | 128811 | R10172 | 762031 | NM_032644 |
| | | | R10075 | 762128 | |
| n673 | manic fringe (*Drosophila*) homolog | 51817 | H22922 | 891617 | NM_002405 |
| | | | H24102 | 892797 | |
| n674 | Nucleoside phosphorylase | 769890 | AA430735 | 2110957 | NM_000270 |
| | | | AA430382 | 2111274 | |
| n675 | Unamed | 431425 | AA706858 | 2716776 | |
| n676 | Unamed | 308105 | W24588 | 1267592 | |
| | | | N95322 | 1301479 | |
| n677 | non-metastatic cells 2, protein | 755239 | AA422139 | 2100891 | NM_002512 |
| | | | AA422058 | 2101007 | |
| n678 | 3-hydroxyanthranilate 3,4-dioxygenase | 1635163 | AI005031 | 3214541 | NM_012205 |
| | | 109310 | T80921 | 703731 | |
| | | | T80846 | 703806 | |
| n679 | serum constituent protein | 214982 | H74163 | 1047382 | NM_007061 |
| | | | | 1047425 | |
| n680 | Proteasome activator subunit 2 | 511043 | AA102276 | 1646580 | NM_002818 |
| | | | AA100289 | 1646687 | |
| n681 | major histocompatibility complex, class I, F | 1604703 | AA988615 | 3173606 | NM_018950 |
| n682 | Hypothetical protein FLJ10761 | 233349 | H77535 | 1055624 | NM_018208 |
| | | | H77536 | 1055625 | |
| n683 | *Homo sapiens* cDNA FLJ23593 | 450079 | AA703419 | 2713337 | |
| n684 | Unamed | 712604 | AA281932 | 1924610 | |
| n685 | Hypothetical protein FLJ14590 | 839941 | AA490142 | 2220836 | NM_032807 |
| | | | AA489961 | 2221017 | |
| n686 | KIAA1424 protein | 795277 | AA454021 | 2165480 | |
| | | | AA451811 | 2167690 | |
| n687 | lectin, galactoside-binding, soluble, 3 binding protein | 811000 | AA485508 | 2214572 | NM_005567 |
| | | | AA485353 | 2214727 | |
| n688 | delta-like homolog | 296815 | W01204 | 1231488 | NM_003836 |
| | | 436121 | N74203 | 1273183 | |
| | | | AA701996 | 2705109 | |
| n689 | LIM domain only 4 | 162533 | H27986 | 898339 | NM_006769 |
| n690 | serine threonine protein kinase | 826135 | AA521346 | 2261889 | NM_007271 |
| n691 | Programmed cell death 10 | 137836 | R68344 | 841861 | NM_007217 |
| | | | R68555 | 842072 | |
| n692 | Unamed | 823819 | AA490281 | 2219454 | |
| | | | AA490390 | 2219563 | |
| n693 | CASP2 and RIPK1 domain containing adaptor with death domain | 24032 | T78285 | 795393 | NM_003805 |
| | | 700353 | R37937 | 696794 | |
| | | | AA290955 | 1927951 | |
| | | | AA285065 | 1938789 | |
| n694 | vesicle-associated membrane protein 3 | 843248 | AA486016 | 2216232 | NM_004781 |
| | | | AA488635 | 2216066 | |
| n695 | Olfactory receptor, family 7, subfamily E, member 12 pseudogene | 1291972 | AA707468 | 2717386 | |
| n696 | Regenerating islet-derived 1 beta | 1412300 | AA844864 | 2931315 | NM_006507 |
| n697 | aldo-keto reductase family 1, member C1 | 196992 | R93124 | 967290 | NM_001353 |
| n698 | *Homo sapiens* serologically defined breast cancer antigen NY-BR-96 | 511257 | AA088799 | 1634234 | |
| | | 127458 | AA088722 | 1634345 | |
| | | | R08769 | 760691 | |
| | | | R08768 | 768825 | |
| n699 | ataxia telangiectasia mutated | 360778 | AA016988 | 1477301 | NM_000051 |
| | | | AA016254 | 1479171 | |
| n700 | Otoferlin | 38517 | R51235 | 813137 | NM_004802 |
| | | | R51236 | 813138 | |
| n701 | Hypothetical protein FLJ12783 | 178922 | H48148 | 924200 | NM_031426 |
| | | | H49932 | 989773 | |
| n702 | nuclear factor-like 3 | 1034644 | AA779843 | 2839174 | NM_004289 |
| n703 | Basonuclin | 132373 | R25330 | 781465 | NM_001717 |
| | | | R26526 | 782661 | |
| n704 | Hypothetical protein FLJ20421 | 502656 | AA125789 | 1687760 | NM_017813 |
| | | | AA127047 | 1687659 | |
| n705 | H19, imprinted maternally expressed untranslated mRNA | 884644 | AA629897 | 2552508 | |
| n706 | AD-012 protein | 787925 | AA452282 | 2165951 | NM_018449 |
| n707 | Activating transcription factor 5 | 1472585 | AA872311 | 2968489 | NM_012068 |

TABLE 3-continued

| Marker | Gene Name | Image Clone ID | Image Clone Accession # | Image Clone GI# | Genbank or RefSeq nuc accession# |
|---|---|---|---|---|---|
| n708 | Latrophilin | 897731 | AA598995 | 2432035 | NM_012302 |
| n709 | Not56-like protein | 131091 | R23327 | 778139 | NM_005787 |
|  |  |  | R23251 | 778215 |  |
| n710 | fatty acid desaturase 1 | 782503 | AA431773 | 2115481 | NM_013402 |
|  |  |  | AA432026 | 2115734 |  |
| n711 | Cdc42 effector protein 4; binder of Rho GTPases 4 | 321488 | W32606 | 1313499 | NM_012121 |
|  |  |  | W32509 | 1313616 |  |
| n712 | Niemann-Pick disease, type C1 | 868484 | AA634267 | 2557481 | NM_000271 |
| n713 | CGI-115 protein | 772918 | AA479913 | 2204395 | NM_016052 |
| n714 | CTP synthase | 46182 | H09614 | 874435 | NM_001905 |
|  |  |  |  | 874436 |  |
| n715 | Interleukin 1 receptor-like 1 | 501994 | AA125917 | 1687503 | NM_003856 |
|  |  |  | AA128153 | 1687395 | NM_016232 |
| n716 | Enolase 1 | 392678 | AA708342 | 2718260 | NM_001428 |
| n717 | v-yes-1 Yamaguchi sarcoma viral related oncogene homolog | 193913 | R83836 | 928713 | NM_002350 |
|  |  |  | R83837 | 928714 |  |
| n718 | Spermidine synthase | 856796 | AA669545 | 2631044 | NM_003132 |
| n719 | nuclear autoantigenic sperm protein (histone-binding) | 447918 | AA644128 | 2569346 | NM_002482 |
| n720 | Phosphoglucomutase 1 | 843174 | AA488373 | 2215804 | NM_002633 |
|  |  |  | AA488504 | 2215935 |  |
| n721 | Unamed | 809466 | AA456161 | 2179371 | NM_006114 |
|  |  |  | AA443094 | 2155769 |  |
| n722 | NADH dehydrogenase | 562409 | AA214053 | 1812675 | NM_004552 |
|  |  |  | AA214154 | 1812791 |  |
| n723 | Hypothetical protein | 752690 | AA417805 | 2079589 | NM_016505 |
|  |  |  | AA417806 | 2079590 |  |
| n724 | Interleukin 10 receptor, alpha | 757440 | AA437226 | 2142140 | NM_001558 |
|  |  |  | AA442290 | 2154168 |  |
| n725 | Exportin 1 | 109333 | T59055 | 660892 | NM_003400 |
|  |  |  | T59131 |  |  |
| n726 | Phosphofructokinase, platelet | 950682 | AA608558 | 2456986 | NM_002627 |
| n727 | *Homo sapiens* mRNA for KIAA1750 protein | 745011 | AA626024 | 2538411 |  |
| n728 | Ser/Arg-related nuclear matrix protein | 132395 | AA976063 | 3151855 | NM_005839 |
| n729 | Bromodomain-containing 4 | 511865 | AA085917 | 1629293 | NM_014299 |
|  |  |  | AA085918 | 1629294 |  |
| n730 | major histocompatibility complex, class I, C | 810142 | AA464354 | 2189238 | NM_002117 |
|  |  |  | AA464246 | 2189130 |  |
| n731 | Ras homolog enriched in brain 2 | 756401 | AA482117 | 2209795 | NM_005614 |
| n732 | U6 suRNA-associated Sm-like protein LSm7 | 741842 | AA402875 | 2056629 | NM_016199 |
| n733 | Polypyrimidine tract binding protein | 897233 | AA677517 | 2658039 | NM_002819 |
| n734 | Catenin | 177772 | H45976 | 922028 | NM_004389 |
|  |  | 48677 | H46041 | 922093 |  |
|  |  |  | H16078 | 880898 |  |
|  |  |  | H16079 | 880899 |  |
| n735 | *Homo sapiens* mRNA cDNA DKFZpS64H1916 | 855244 | AA630545 | 2553156 |  |
| n736 | Unamed | 725630 | AA293211 | 1941492 |  |
|  |  |  | AA293653 | 1941493 |  |

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" is a naturally-occurring polymer corresponding to at least one of the nucleic acids listed in Tables 1-3. For example, markers include, without limitation, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (e.g. including proteins both before and after cleavage of normally cleaved regions such as transmembrane signal sequences). As used herein, "marker" may also include a cDNA made by reverse transcription of an RNA generated by transcription of genomic DNA (including spliced RNA).

As used herein a "polynucleotide corresponds to" another (a first) polynucleotide if it is related to the first polynucleotide by any of the following relationships: 1) The second polynucleotide comprises the first polynucleotide and the second polynucleotide encodes a gene product. 2) The second polynucleotide is 5' or 3' to the first polynucleotide in cDNA, RNA, genomic DNA, or fragment of any of these polynucleotides. For example, a second polynucleotide may be fragment of a gene that includes the first and second polynucleotides. The first and second polynucleotides are related in that they are components of the gene coding for a gene product, such as a protein or antibody. However, it is not necessary that the second polynucleotide comprises or overlaps with the first polynucleotide to be encompassed within the definition of "corresponding to" as used herein. For example, the first polynucleotide may be a fragment of a 3' untranslated region of the second polynucleotide. The first and second polynucleotide may be fragments of a gene coding for a gene product. The second polynucleotide may be an exon of the gene while the first polynucleotide may be an intron of the gene. 3) The second polynucleotide is the complement of the first polynucleotide.

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

A "breast-associated" body fluid is a fluid which, when in the body of a patient, contacts or passes through breast cells or into which cells, nucleic acids or proteins shed from breast cells are capable of passing. Exemplary breast-associated body fluids include blood fluids, lymph, cystic fluid, urine and nipple aspirates.

The "normal" level of expression of a marker is the level of expression of the marker in breast cells of a patient, e.g. a human, not afflicted with breast cancer. "Over-expression" and "under-expression" of a marker refer to expression of the marker of a patient at a greater or lesser level, respectively, than normal level of expression of the marker (e.g. at least two-fold greater or lesser level).

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer, which corresponds to the promoter, is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" is a polynucleotide (e.g. an RNA, a cDNA, or an analog of one of an RNA or cDNA) which is complementary to or homologous with all or a portion of a mature RNA made by transcription of a genomic DNA corresponding to a marker of the invention and normal post-transcriptional processing (e.g. splicing), if any, of the transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A marker is "fixed" to a substrate if it is covalently or non-covalently associated with the substrate such the substrate can be rinsed with a fluid (e.g. standard saline citrate, pH 7.4) without a substantial fraction of the marker dissociating from the substrate.

As used herein, a "naturally-occurring" nucleic acid molecule refers to an RNA or DNA molecule having a nucleotide sequence that occurs in nature (e.g. encodes a natural protein).

Expression of a marker in a patient is "significantly" higher or lower than the normal level of expression of a marker if the level of expression of the marker is greater or less, respectively, than the normal level by an amount greater than the standard error of the assay employed to assess expression, and preferably at least twice, and more preferably three, four, five or ten times that amount. Alternately, expression of the marker in the patient can be considered "significantly" higher or lower than the normal level of expression if the level of expression is at least about two, and preferably at least about three, four, or five times, higher or lower, respectively, than the normal level of expression of the marker.

Breast cancer is "inhibited" if at least one symptom of the cancer is alleviated, terminated, slowed, or prevented. As used herein, breast cancer is also "inhibited" if recurrence or metastasis of the cancer is reduced, slowed, delayed, or prevented.

A kit is any manufacture (e.g. a package or container) comprising at least one reagent, e.g. a probe, for specifically detecting a marker of the invention, the manufacture being promoted, distributed, or sold as a unit for performing the methods of the present invention.

Description

The present invention is based, in part, on identification of markers which are expressed at a different level in breast cancer tumors than they are in normal (i.e. non-cancerous) breast cells. The markers of the invention correspond to nucleic acid and polypeptide molecules which can be detected in one or both of normal and cancerous breast tumor cells. The presence, absence, or level of expression of one or more of these markers in breast cells is herein correlated with the cancerous state of the tissue.

The present invention also provides markers which are differently expressed in estrogen receptor (ER) positive or ER negative breast tumor cells. Estrogen receptors are molecules on the surface of normal breast cells. Breast cancers that have estrogen receptors are said to be "ER positive," while those breast cancers that do not possess estrogen receptors are "ER negative." In patients with ER positive cancers, cancer cell growth is under the control of estrogen. Therefore, such cancers are often susceptible to treatment with agents, such as tamoxifen, a non-steroidal anti-estrogen, which blocks the interaction between estrogen and the estrogen receptor. It is believed that this blocked interaction prevents the growth stimulation effects that estrogens would cause, should they bind to the breast cancer cells.

The invention thus includes compositions, kits, and methods for assessing the cancerous state of breast cells (e.g. cells obtained from a human, cultured human cells, archived or preserved human cells and in vivo cells).

The compositions, kits, and methods of the invention have the following uses, among others:

1) assessing whether a patient is afflicted with breast cancer;
2) assessing the stage of breast cancer in a patient;
3) assessing the grade of breast cancer in a patient;
4) assessing the benign or malignant nature of breast cancer in a patient;
5) assessing whether a breast tumor is ER positive;
6) assessing whether a breast tumor is ER negative;
7) making an isolated hybridoma which produces an antibody useful for assessing whether a patient is afflicted with breast cancer;
8) assessing the presence of breast cancer cells;
9) assessing the efficacy of one or more test compounds for inhibiting breast cancer in a patient;
10) assessing the efficacy of a therapy for inhibiting breast cancer in a patient;
11) assessing the efficacy of a therapy for inhibiting ER positive breast cancer in a patient;
12) assessing the efficacy of a therapy for inhibiting ER negative breast cancer in a patient;
13) monitoring the progression of breast cancer in a patient;
14) selecting a composition or therapy for inhibiting breast cancer in a patient;
15) selecting a composition or therapy for inhibiting ER positive breast cancer in a patient;
16) selecting a composition or therapy for inhibiting ER negative breast cancer in a patient;
17) developing agents effective in treating tumors;
18) developing agents effective in treating ER positive breast cancer tumors;
19) developing agents effective in treating ER negative breast cancer tumors;
20) treating a patient afflicted with breast cancer;
21) inhibiting breast cancer in a patient;
22) assessing the carcinogenic potential of a test compound; and
23) inhibiting breast cancer in a patient at risk for developing breast cancer.

The methods of the present invention comprise the step of comparing the level of expression of a marker in a ER positive breast tumor patient sample, wherein the marker is listed in Table 1 and the normal level or control level of expression of the marker. A significant difference between the level of expression of the marker in the patient sample and the normal or control level is an indication that the patient is afflicted with breast cancer. A "normal" level of expression refers to the expression level of the marker in a sample from a patient without breast cancer, e.g. non-cancerous human breast tissue. A "control" level of expression refers to the expression level of the marker in an identified source, e.g. identified by phenotypic and/or genotypic analysis, e.g. clinical status. For example, the methods of the present invention comprise the step of comparing the level of expression of a marker of Table 2 (ER positive marker) in a patient sample and the level of expression of the marker in an ER negative breast tumor sample, wherein a significant difference between the level of expression of the marker in the patient sample and the ER negative breast tumor sample is an indication that the patient is afflicted with ER positive breast cancer. The level of expression of the marker in the ER negative breast tumor sample is therefore the "control."

Likewise, the methods of the present invention comprise the step of comparing the level of expression of a marker of Table 3 (ER negative marker) in a patient sample and the level of expression of a marker in an ER positive breast tumor sample, wherein a significant difference between the level of expression of the marker in the patient sample and the ER positive breast tumor sample is an indication that the patient is afflicted with ER negative breast cancer. The level of expression of the marker in the ER positive breast tumor sample is therefore the "control." Alternatively, and particularly as further information becomes available as a result of routine performance of the methods described herein, population-average values for expression of the markers of the invention may be used as the "control".

The polynucleotides set forth in Table 1 are thus newly-associated with ER positive or ER negative breast cancer. Also provided by this invention are polynucleotides that correspond to the polynucleotides of Table 1. In one embodiment, these polynucleotides are obtained by identification of a larger fragment or full-length coding sequence of these polynucleotides. Gene delivery vehicles, host cells, compositions and databases (all describe herein) containing these polynucleotides are also provided by this invention.

The invention also encompasses polynucleotides which differ from that of the polynucleotides described above, but which produce the same phenotypic effect, e.g. allelic variants. These altered, but phenotypically equivalent polynucleotides are referred to as "equivalent nucleic acids." This invention also encompasses polynucleotides characterized by changes in non-coding regions that do not alter the polypeptide produced therefrom when compared to the polynucleotide herein. This invention further encompasses polynucleotides which hybridize to the polynucleotides of the subject invention under conditions of moderate or high stringency. Alternatively, the polynucleotides are at least 85%, or at least 90%, or more preferably, greater or equal to 95% identical as determined by a sequence alignment program when run under default parameters.

Any marker or combination of markers listed in Table 1, as well as any known markers in combination with the markers set forth in Table 1, may be used in the compositions, kits, and methods of the present invention. In general, it is preferable to use markers for which the difference between the level of expression of the marker in breast cancer cells and the level of expression of the same marker in normal breast cells or a control is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater.

It is recognized that certain markers correspond to proteins which are secreted from breast cells (i.e. one or both of normal and cancerous cells) to the extracellular space surrounding the cells. These markers are preferably used in certain embodiments of the compositions, kits, and methods of the invention, owing to the fact that the protein corresponding to each of these markers can be detected in an breast-associated body fluid sample, which may be more easily collected from a human patient than a tissue biopsy sample. In addition, preferred in vivo techniques for detection of a protein corresponding to a marker of the invention include introducing into a subject a labeled antibody directed against the protein. For example, the antibody can be labeled with a radioactive marker whose presence and location in a subject can be detected by standard imaging techniques.

Although not every marker corresponding to a secreted protein is indicated as such herein, it is a simple matter for the skilled artisan to determine whether any particular marker corresponds to a secreted protein. In order to make this determination, the protein corresponding to a marker is expressed in a test cell (e.g. a cell of a breast cell line), extracellular fluid is collected, and the presence or absence of the protein in the extracellular fluid is assessed (e.g. using a labeled antibody which binds specifically with the protein).

The following is an example of a method which can be used to detect secretion of a protein corresponding to a marker of the invention. About $8 \times 10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE™ (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-$^{35}$S™ reagent (ICN Catalog no. 51006) are added to each well. The wells are maintained under the 5% $CO_2$ atmosphere described above and incubated at 37° C. for a selected period. Following incubation, 150 microliters of conditioned medium is removed and centrifuged to remove floating cells and debris. The presence of the protein in the supernatant is an indication that the protein is secreted.

Examples of breast-associated body fluids include blood fluids (e.g. whole blood, blood serum, blood having platelets removed therefrom, etc.), lymph, ascitic fluid, cystic fluid, urine and nipple aspirates. In these embodiments, the level of expression of the marker can be assessed by assessing the amount (e.g. absolute amount or concentration) of the marker in a breast-associated body fluid obtained from a patient. The fluid can, of course, be subjected to a variety of well-known post-collection preparative and storage techniques (e.g. storage, freezing, ultrafiltration, concentration, evaporation, centrifugation, etc.) prior to assessing the amount of the marker in the fluid.

Many breast-associated body fluids (i.e. usually excluding urine) can have breast cells therein, particularly when the breast cells are cancerous, and, more particularly, when the breast cancer is metastasizing. Thus, the compositions, kits, and methods of the invention can be used to detect expression of markers corresponding to proteins having at least one portion which is displayed on the surface of cells which express it. It is a simple matter for the skilled artisan to determine whether the protein corresponding to any particular marker comprises a cell-surface protein. For example, immunological methods may be used to detect such proteins on whole cells, or well known computer-based sequence analysis methods (e.g. the SIGNALP program; Nielsen et al., 1997, *Protein Engineering* 10:1-6) may be used to predict the presence of at least one extracellular domain (i.e. including both secreted proteins and proteins having at least one cell-surface domain). Expression of a marker corresponding to a protein having at least one portion which is displayed on the surface of a cell which expresses it may be detected without necessarily lysing the cell (e.g. using a labeled antibody which binds specifically with a cell-surface domain of the protein).

Expression of a marker of the invention may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a protein or a fragment thereof, corresponding to the marker, such as the protein encoded by the open reading frame corresponding to the marker or such a protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a polynucleotide comprising the marker, and fragments thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker of the invention. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal breast cells, cancerous breast cells and controls.

It is understood that by routine screening of additional patient samples using one or more of the markers of the invention, it will be realized that certain of the markers are over- or under-expressed in cancers of various types, including specific breast cancers, as well as other cancers such as ovarian cancer, cervical cancer, etc. For example, it will be confirmed that some of the markers of the invention are over- or under-expressed in most (i.e. 50% or more) or substantially all (i.e. 80% or more) of breast cancer. Furthermore, it will be confirmed that certain of the markers of the invention are associated with breast cancer of various stages (i.e. stage 0, I, II, II, and IV breast cancers, as well as subclassifications IIA, IIB, IIIA, and IIIB, using the FIGO Stage Grouping system for primary carcinoma of the breast; (see Breast, In: *American Joint Committee on Cancer: AJCC Cancer Staging Manual*. Lippincott-Raven Publishers, 5th ed., 1997, pp. 171-180), of various histologic subtypes (e.g. serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Müllerian) mixed-tumor, mesonephroid tumor, malignant carcinoma, Brenner tumor, mixed epithelial tumor, and undifferentiated carcinoma, using the WHO/FIGO system for classification of malignant breast tumors; Scully, *Atlas of Tumor Pathology*, 3d series, Washington D.C.), and various grades (i.e. grade I {well differentiated}, grade II {moderately well differentiated}, and grade III {poorly differentiated from surrounding normal tissue})). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of breast cancer in patients. In addition, these compositions, kits, and methods can be used to detect and differentiate lobular and ductal carcinoma breast cancers.

When the compositions, kits, and methods of the invention are used for characterizing one or more of the stage, grade, histological type, and benign/malignant nature of breast cancer in a patient, it is preferred that the marker or panel of markers of the invention is selected such that a positive result is obtained in at least about 20%, and preferably at least about 40%, 60%, or 80%, and more preferably in substantially all patients afflicted with an breast cancer of the corresponding stage, grade, histological type, or benign/malignant nature. Preferably, the marker or panel of markers of the invention is selected such that a PPV of greater than about 10% is obtained for the general population (more preferably coupled with an assay specificity greater than 99.5%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly enhanced level of expression of more than one of the plurality of markers in the sample, relative to the corresponding normal levels, is an indication that the patient is afflicted with breast cancer. When a plurality of markers is used, it is preferred that 2, 3, 4, 5, 8, 10, 12, 15, 20, 30, or 50 or more individual markers be used, wherein fewer markers are preferred.

In order to maximize the sensitivity of the compositions, kits, and methods of the invention (i.e. by interference attributable to cells of non-breast origin in a patient sample), it is preferable that the marker of the invention used therein be a marker which has a restricted tissue distribution, e.g., normally not expressed in a non-breast tissue.

Prior to the present invention, only a small number of markers were known to be associated with breast cancers (e.g. BRCA1 and BRCA2). These markers are not, of course, included among the markers of the invention, although they may be used together with one or more markers of the invention in a panel of markers. For example, a sample may be assayed to determine the presence and/or expression levels of known markers in combination with the markers of the present invention. The presence, over- and/or under-expression of markers, such as BRCA1, BRCA2 (Eisen, M B. et al. (1998) *Proc Natl Acad Sci, USA*, 95:14863-14868) and HER2 in combination with the presence, over- and/or underexpression of the markers of the present invention, may be used to further characterize breast cancer tumors. Methods for assaying HER2 are described-for example, in U.S. Pat. No. 4,968, 603, filed Dec. 31, 1986, entitled "Determination of Status in Neoplastic Disease," which is incorporated herein by reference. Other characteristics, such as luminal/basal epithelial type (Hedenfalk, I. et al. (2001) *N Engl J Med* 344(8):539-548), may also be identified and assist in further characterizing and treating breast cancer.

It is recognized that the compositions, kits, and methods of the invention will be of particular utility to patients having an enhanced risk of developing breast cancer and their medical advisors. Patients recognized as having an enhanced risk of developing breast cancer include, for example, patients having a familial history of breast cancer, patients identified as having a mutant oncogene (i.e. at least one allele), and patients of advancing age (i.e. women older than about 50 or 60 years).

The level of expression of a marker in normal (i.e. non-cancerous) human breast tissue or a control can be assessed in a variety of ways. In one embodiment, the normal level of expression is assessed by assessing the level of expression of the marker in a portion of breast cells which appears to be non-cancerous and by comparing the normal level of expression with the level of expression in a portion of the breast cells which is suspected of being cancerous. For example, when mammography or other medical procedure, reveals the presence of a lump in a patient's breast, the normal level of expression of a marker may be assessed using the non-affected breast tissue, and this normal level of expression may be compared with the level of expression of the same marker in an affected portion (i.e. the lump) of the affected breast. Alternately, and particularly as further information becomes available as a result of routine performance of the methods described herein, population-average values for expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of breast cancer in the patient, from archived patient samples, and the like.

The invention includes compositions, kits, and methods for assessing the presence of breast cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of breast cancer cells (e.g. in a sample such as a patient sample). The kit comprises a plurality of reagents, each of which is capable of binding specifically with a nucleic acid or polypeptide corresponding to a marker of the invention. Suitable reagents for binding with a polypeptide corresponding to a marker of the invention include antibodies, antibody derivatives, antibody fragments, and the like. Suitable reagents for binding with a nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal breast cells, a sample of breast cancer cells, and the like.

The invention also includes a method of making an isolated hybridoma which produces an antibody useful for assessing whether patient is afflicted with breast cancer. In this method, a protein corresponding to a marker of the invention is isolated (e.g. by purification from a cell in which it is expressed or by transcription and translation of a nucleic acid encoding the protein in vivo or in vitro using known methods). A vertebrate, preferably a mammal such as a mouse, rat, rabbit, or sheep, is immunized using the isolated protein or protein fragment. The vertebrate may optionally (and preferably) be immunized at least one additional time with the isolated protein or protein fragment, so that the vertebrate exhibits a robust immune response to the protein or protein fragment. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the protein or protein fragment. The invention also includes hybridomas made by this method and antibodies made using such hybridomas.

The invention also includes a method of assessing the efficacy of a test compound for inhibiting breast cancer cells. As described above, differences in the level of expression of the markers of the invention correlate with the cancerous state of breast cells. Although it is recognized that changes in the levels of expression of certain of the markers of the invention likely result from the cancerous state of breast cells, it is likewise recognized that changes in the levels of expression of other of the markers of the invention induce, maintain, and promote the cancerous state of those cells. Thus, compounds which inhibit breast cancer in a patient will cause the level of expression of one or more of the markers of the invention to change to a level nearer the normal level of expression for that marker (i.e. the level of expression for the marker in non-cancerous breast cells).

This method thus comprises comparing expression of a marker in a first breast cell sample and maintained in the presence of the test compound and expression of the marker in a second breast cell sample and maintained in the absence of the test compound. A significant decrease in the level of expression of a marker listed in Table 1 may be an indication that the test compound inhibits breast cancer. The breast cell samples may, for example, be aliquots of a single sample of normal breast cells obtained from a patient, pooled samples of normal breast cells obtained from a patient, cells of a normal breast cell line, aliquots of a single sample of breast cancer cells obtained from a patient, pooled samples of breast cancer cells obtained from a patient, cells of a breast cancer cell line, or the like. In one embodiment, the samples are breast cancer cells obtained from a patient and a plurality of compounds known to be effective for inhibiting various breast cancers are tested in order to identify the compound which is likely to best inhibit the breast cancer in the patient.

This method may likewise be used to assess the efficacy of a therapy for inhibiting breast cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significant decrease in the level of expression of a marker listed in Table 1, or blocks induction of a marker listed in Table 1, then the therapy may be efficacious for inhibiting breast cancer. As above, if samples from a selected patient are used in this method, then alternative therapies can be assessed in vitro in order to select a therapy most likely to be efficacious for inhibiting breast cancer in the patient.

The present invention further provides methods for identifying the presence of ER positive and ER negative breast tumor cells by detecting expression of a marker listed in Tables 2 or 3, respectively. By identifying whether a breast tumor is ER positive or ER negative, therapy may be customized to better treat the specific type of tumor. For example, if a tumor is ER positive, an agent which binds to an estrogen receptor or binds to an estrogen receptor substrate, thereby prohibiting binding between estrogen and the estrogen receptor, may be administered to the patient.

As described herein, breast cancer in patients is associated with levels of expression of one or more markers listed in Table 1. While, as discussed above, some of these changes in expression level result from occurrence of the breast cancer, others of these changes induce, maintain, and promote the cancerous state of breast cancer cells. Thus, breast cancer characterized by an alteration in the level of expression of one or more markers listed in Table 1 can be inhibited by hampering or increasing expression of those markers.

Expression of a marker listed in Table 1 can be inhibited in a number of ways generally known in the art. For example, an antisense oligonucleotide can be provided to the breast cancer cells in order to inhibit transcription, translation, or both, of the marker(s). Alternately, a polynucleotide encoding an antibody, an antibody derivative, or an antibody fragment, and operably linked with an appropriate promoter/regulator region, can be provided to the cell in order to generate intracellular antibodies which will inhibit the function or activity of the protein corresponding to the marker(s). Using the methods described herein, a variety of molecules, particularly including molecules sufficiently small that they are able to cross the cell membrane, can be screened in order to identify molecules which inhibit expression of the marker(s). The compound so identified can be provided to the patient in order to inhibit expression of the marker(s) in the breast cancer cells of the patient.

Expression of a marker listed within Table 1 can be enhanced in a number of ways generally known in the art. For example, a polynucleotide encoding the marker and operably linked with an appropriate promoter/regulator region can be provided to breast cancer cells of the patient in order to induce enhanced expression of the protein (and mRNA) corresponding to the marker therein. Alternatively, if the protein is capable of crossing the cell membrane, inserting itself in the cell membrane, or is normally a secreted protein, then expression of the protein can be enhanced by providing the protein (e.g. directly or by way of the bloodstream or another breast-associated fluid) to breast cancer cells in the patient.

As described above, the cancerous state of human breast cells is correlated with changes in the levels of expression of the markers of the invention. The invention thus includes a method for assessing the human breast cell carcinogenic potential of a test compound. This method comprises maintaining separate aliquots of human breast cells in the presence and absence of the test compound. Expression of a marker of the invention in each of the aliquots is compared. A significant increase in the level of expression of a marker listed in Table 1 in the aliquot maintained in the presence of the test compound (relative to the aliquot maintained in the absence of the test compound) may be an indication that the test compound possesses human breast cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

I. Isolated Nucleic Acid Molecules

One aspect of the invention pertains to isolated nucleic acid molecules that correspond to a marker of the invention, including nucleic acids which encode a polypeptide corresponding to a marker of the invention or a portion of such a polypeptide. Isolated nucleic acids of the invention also include nucleic acid molecules sufficient for use as hybridization probes to identify nucleic acid molecules that correspond to a marker of the invention, including nucleic acids which encode a polypeptide corresponding to a marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g. mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid encoding a protein corresponding to a marker listed in Table 1, can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A process for identifying a larger fragment or the full-length coding sequence of a marker of the present invention is thus also provided. Any conventional recombinant DNA techniques applicable for isolating polynucleotides may also be employed. One such method involves the 5'-RACE-PCR technique, in which the poly-A mRNA that contains the coding sequence of particular interest is first reverse transcribed with a 3'-primer comprising a sequence disclosed herein. The newly synthesized cDNA strand is then tagged with an anchor primer with a known sequence, which preferably contains a convenient cloning restriction site attached at the 5' end. The tagged cDNA is then amplified with the 3'-primer (or a nested primer sharing sequence homology to the internal sequences of the coding region) and the 5'-anchor primer. The amplification may be conducted under conditions of various levels of stringency to optimize the amplification specificity. 5'-RACE-PCR can be readily performed using commercial kits (available from, e.g., BRL Life Technologies Inc., Clontech) according to the manufacturer's instructions.

Isolating the complete coding sequence of a gene can also be carried out in a hybridization assay using a suitable probe. The probe preferably comprises at least 10 nucleotides, and more preferably exhibits sequence homology to the polynucleotides of the markers of the present invention. Other high throughput screens for cDNAs, such as those involving gene chip technology, can also be employed in obtaining the complete cDNA sequence.

In addition, databases exist that reduce the complexity of ESTs by assembling contiguous EST sequences into tentative genes. For example, TIGR has assembled human ESTs into a datable called THC for tentative human consensus sequences. The THC database allows for a more definitive assignment compared to ESTs alone. Software programs exist (TIGR assembler and TIGEM EST assembly machine and contig assembly program (see Huang, X., 1996, *Genomes* 33:21-23)) that allow for assembling ESTs into contiguous sequences from any organism.

Alternatively, mRNA from a sample preparation is used to construct cDNA library in the ZAP Express vector following the procedure described in Velculescu et al., 1997, *Science* 270:484. The ZAP Express cDNA synthesis kit (Stratagene) is used accordingly to the manufacturer's protocol. Plates containing 250 to 2000 plaques are hybridized as described in Rupert et al., 1988, *Mol. Cell. Bio.* 8:3104 to oligonucleotide probes with the same conditions previously described for standard probes except that the hybridization temperature is reduced to a room temperature. Washes are performed in 6×standard-saline-citrate 0.1% SDS for 30 minutes at room temperature. The probes are labeled with $^{32}$P-ATP trough use of T4 polynucleotide kinase.

A partial cDNA (3' fragment) can be isolated by 3' directed PCR reaction. This procedure is a modification of the protocol described in Polyak et al., 1997, *Nature* 389:300. Briefly, the procedure uses SAGE tags in PCR reaction such that the resultant PCR product contains the SAGE tag of interest as well as additional cDNA, the length of which is defined by the position of the tag with respect to the 3' end of the cDNA. The cDNA product derived from such a transcript driven PCR reaction can be used for many applications.

RNA from a source to express the cDNA corresponding to a given tag is first converted to double-stranded cDNA using any standard cDNA protocol. Similar conditions used to generate cDNA for SAGE library construction can be employed except that a modified oligo-dT primer is used to derive the first strand synthesis. For example, the oligonucleotide of composition 5'-B-TCC GGC GCG CCG TTT TCC CAG TCA CGA(30)-3', contains a poly-T stretch at the 3' end for hybridization and priming from poly-A tails, an M13 priming site for use in subsequent PCR steps, a 5' Biotin label (B) for capture to strepavidin-coated magnetic beads, and an AscI restriction endonuclease site for releasing the cDNA from the strepavidin-coated magnetic beads. Theoretically, any sufficiently-sized DNA region capable of hybridizing to a PCR primer can be used as well as any other 8 base pair recognizing endonuclease.

cDNA constructed utilizing this or similar modified oligo-dT primer is then processed exactly as described in U.S. Pat. No. 5,695,937 up until adapter ligation where only one adapter is ligated to the cDNA pool. After Adapter ligation, the cDNA is released from the streptavidin-coated magnetic beads and is then used as a template for cDNA amplification.

Various PCR protocols can be employed using PCR priming sites within the 3' modified oligo-dT primer and the SAGE tag. The SAGE tag-derived PCR primer employed can be of varying length dictated by 5' extension of the tag into the adaptor sequence. cDNA products are now available for a variety of applications.

This technique can be further modified by: (1) altering the length and/or content of the modified oligo-dT primer; (2) ligating adaptors other than that previously employed within the SAGE protocol; (3) performing PCR from template retained on the streptavidin-coated magnetic beads; and (4) priming first strand cDNA synthesis with non-oligo-dT based primers.

Gene trapper technology can also be used. The reagents and manufacturer's instructions for this technology are commercially available from Life Technologies, Inc., Gaithsburg, Md. Briefly, a complex population of single-stranded phagemid DNA containing directional cDNA inserts is enriched for the target sequence by hybridization in solution to a biotinylated oligonucleotide probe complementary to the target sequence. The hybrids are captured on streptavidin-coated paramagnetic beads. A magnet retrieves the paramagnetic beads from the solution, leaving nonhybridized single-stranded DNAs behind. Subsequently, the captured single-stranded DNA target is released from the biotinylated oligonucleotide. After release, the cDNA clone is further enriched by using a nonbiotinylated target oligonucleotide to specifically prime conversion of the single-stranded DNA. Following transformation and plating, typically 20% to 100% of the colonies represent the cDNA clone of interest. To identify the desired cDNA clone, the colonies may be screened by colony hybridization using the $^{32}$P-labeled oligonucleotide as described above for solution hybridization, or alternatively by DNA sequencing and alignment of all sequences obtained from numerous clones to determine a consensus sequence.

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a nucleic acid corresponding to a marker of the invention or to the nucleotide sequence of a nucleic acid encoding a protein which corresponds to a marker of the invention. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a protein which corresponds to a marker of the invention, and thus encode the same protein.

In addition to the nucleotide sequences described herein, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a nucleic acid corresponding to a marker of the invention or to a nucleic acid encoding a protein corresponding to a marker of the invention. As used herein, the term "hybridizes under stringent conditions" is intended to describe conditions for hybridization and washing under which nucleotide sequences at least 75% (80%, 85%, preferably 90%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions for annealing two single-stranded DNA each of which is at least about 100 bases in length and/or for annealing a single-stranded DNA and a single-stranded RNA each of which is at least about 100 bases in length, are hybridization in 6×sodium chloride/sodium citrate (SSC) at about 45° C., followed by one or more washes in 0.2×SSC, 0.1% SDS at 50-65° C. Further preferred hybridization conditions are taught in Lockhart, et al., Nature Biotechnology, Volume 14, 1996 August: 1675-1680; Breslauer, et al., Proc. Natl. Acad. Sci. USA, Volume 83, 1986 June: 3746-3750; Van Ness, et al., Nucleic Acids Research, Volume 19, No. 19, 1991 September: 5143-5151; McGraw, et al., BioTechniques, Volume 8, No. 6 1990: 674-678; and Milner, et al., Nature Biotechnology, Volume 15, 1997 June: 537-541, all expressly incorporated by reference.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, such a protein has an amino acid sequence that is at least about 40% identical, 50%, 60%, 70%, 80%, 90%, 95%, or 98% identical to the amino acid sequence of one of the proteins which correspond to the markers of the invention.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an breast-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res*. 15:6625-6641). The antisense nucleic acid molecule can also comprise a 2'-o-methylribonucleotide (Inoue et al., 1987, *Nucleic Acids Res*. 15:6131-6148) or a chimeric RNA-DNA analogue (Inoue et al., 1987, *FEBS Lett*. 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des*. 6(6):569-84; Helene (1992) *Ann. N.Y Acad. Sci*. 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

II. Isolated Proteins and Antibodies

One aspect of the invention pertains to isolated proteins which correspond to individual markers of the invention, and biologically active portions thereof, as well as polypeptide fragments suitable for use as immunogens to raise antibodies directed against a polypeptide corresponding to a marker of the invention. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide corresponding to a marker of the invention include polypeptides comprising amino acid sequences sufficiently identical to or derived from the amino acid sequence of the protein corresponding to the marker, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have amino acid sequences encoded by the nucleic acid sequences described herein. Other useful proteins are substantially identical (e.g., at least about 40%, preferably 50%, 60%, 70%, 80%, 90%, 95%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See world wide web.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a polypeptide corresponding to a marker of the invention can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide corresponding to a marker of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest.

Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the polypeptides corresponding to individual markers of the invention. Such variants have an altered amino acid sequence which can function as either agonists (mimetics) or as antagonists. Variants can be generated by mutagenesis, e.g., discrete point. mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al, 1983 *Nucleic Acid Res*. 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

An isolated polypeptide corresponding to a marker of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the polypeptides of the invention, and encompasses an epitope of the protein such that an antibody raised against the peptide forms a specific immune complex with a marker of the invention to which the protein corresponds. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i e., one that is substantially free of contaminating antibodies. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Antibodies of the invention may be used as therapeutic agents in treating cancers. In a preferred embodiment, completely human antibodies of the invention are used for therapeutic treatment of human cancer patients, particularly those having breast cancer. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol*. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

An antibody directed against a polypeptide corresponding to a marker of the invention (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g. in an ovary-associated body fluid) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980. Accordingly, in one aspect, the invention provides substantially purified antibodies or fragments thereof, and non-human antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to the amino acid sequence of the present invention (wherein the percent identity is determined using the ALIGN program of the GCG software package with a PAM120 weight residue table, a. gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of the present invention, an amino acid sequence encoded by the cDNA of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes a polypeptide of the present invention, the method comprising immunizing a mammal with a polypeptide. The polypeptide used as an immungen comprises an amino acid sequence selected from the group consisting of the amino acid sequence of the present invention, an amino acid sequence encoded by the cDNA of the nucleic acid molecules of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C.

After immunization, a sample is collected from the mammal that contains an antibody that specifically recognizes the polypeptide. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

III. Recombinant Expression Vectors and Host Cells

Another aspect of the invention pertains to vectors, preferably expression vectors, containing a nucleic acid encoding a polypeptide corresponding to a marker of the invention (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, Gene 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g.,. cells that have incorporated the selectable marker gene will survive, while the other cells die).

A host cell of the invention, such as a prokaryotic or eukaryotic host cell in culture, can be used to produce a polypeptide corresponding to a marker of the invention. Accordingly, the invention further provides methods for producing a polypeptide corresponding to a marker of the invention using the host cells of the invention. In one embodiment, the method comprises culturing the host cell of invention (into which a recombinant expression vector encoding a polypeptide of the invention has been introduced) in a suitable medium such that the marker is produced. In another embodiment, the method further comprises isolating the marker polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of the polypeptide corresponding to the marker and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a polypeptide corresponding to a marker of the invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector,.the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915).

The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") corresponding to a marker of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid corresponding to a marker of the invention. Such methods comprise formulating a pharmaceutically acceptable carrier with an agent which modulates expression or activity of a polypeptide or nucleic acid corresponding to a marker of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid corresponding to a marker of the invention and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a marker or biologically active portion thereof. In another embodiment, the invention provides assays for screening candidate or test compounds which bind to a marker or biologically active portion thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}$I, $^{35}$S, $^{14}$C, or $^{3}$H, either directly or indirectly, and the radioisotope detected by direct counting of radioemission or by scintillation counting. Alternatively, assay components can be enzymatically labeled with, for example, horseradish peroxidase, alkaline.

phosphatase, or luciferase, and the enzymatic label detected by determination of conversion of an appropriate substrate to product.

In another embodiment, the invention provides assays for screening candidate or test compounds which modulate the activity of a marker or a biologically active portion thereof. In all likelihood, the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of the marker to identify its natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker or downstream elements of a marker-mediated signaling pathway. Alternatively, such marker binding partners may also be found to be inhibitors of the marker.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an breast cancer marker identified herein, the known binding partner and/or substrate of same, and the test compound. Test compounds can be supplied from any source.

The basic principle of the assay systems used to identify compounds that interfere with the interaction between the marker and its binding partner involves preparing a reaction mixture containing the marker and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker and its binding partner. Control reaction mixtures are incubated without the test compound or with a placebo. The formation of any complexes between the marker and its binding partner is then detected. The formation of a complex in the control reaction, but less or no such formation in the reaction mixture containing the test compound, indicates that the compound interferes with the interaction of the marker and its binding partner. Conversely, the formation of more complex in the presence of compound than in the control reaction indicates that the compound may enhance interaction of the marker and its binding partner.

The assay for compounds that interfere with the interaction of the marker with its binding partner may be conducted in a heterogeneous or homogeneous format. Heterogeneous assays involve anchoring either the marker or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the markers and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker or a marker binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993Aug;18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J. Mol. Recognit.* 11: 141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, non-denaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker and its binding partner.

Also within the scope of the present invention are methods for direct detection of interactions between the marker and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of mRNA or protein, corresponding to a marker in the cell, is determined. The level of expression of mRNA or protein in the presence of the candidate compound is compared to the level of expression of mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the breast epithelium). A method for lipidation of antibodies is described by Cruikshank et al. (1997) *J. Acquired Immune Deficiency Syndromes and Human Retrovirology* 14:193.

The nucleic acid molecules corresponding to a marker of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Monitoring the Effectiveness of an Anti-Cancer Agent

As discussed above, the markers of the present invention can be used to assess whether a tumor has become refractory to an ongoing treatment (e.g., a chemotherapeutic treatment). This embodiment of the present invention relies on comparing two or more samples obtained from a patient undergoing anti-cancer treatment. In general, it is preferable to obtain a first sample from the patient prior to beginning therapy and one or more samples during treatment. In such a use, a baseline of expression prior to therapy is determined and then changes in the baseline state of expression is monitored during the course of therapy. Alternatively, two or more successive samples obtained during treatment can be used without the need of a pre-treatment baseline sample. In such a use, the first sample obtained from the subject is used as a baseline for determining whether the expression of a particular gene is increasing or decreasing.

In general, when monitoring the effectiveness of a therapeutic treatment, two or more samples from the patient are examined. Preferably, three or more successively obtained samples are used, including at least one pretreatment sample.

VI. Electronic Apparatus Readable Media and Arrays

Electronic apparatus readable media comprising a breast cancer marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the nucleic acid sequence corresponding to the markers can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any suitable datap-rocessor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has breast cancer or a pre-disposition to breast cancer, wherein the method comprises the steps of determining the presence or absence of a breast cancer marker and based on the presence or absence of the breast cancer marker, determining whether the subject has breast cancer or a pre-disposition to breast cancer and/or recommending a particular treatment for the breast cancer or pre-breast cancer condition.

The present invention further provides in an electronic system and/or in a network, a method for determining whether a subject has breast cancer or a pre-disposition to breast cancer associated with a breast cancer marker wherein the method comprises the steps of determining the presence or absence of the breast cancer marker, and based on the presence or absence of the breast cancer marker, determining whether the subject has breast cancer or a pre-disposition to breast cancer, and/or recommending a particular treatment for the breast cancer or pre-breast cancer condition. The method may further comprise the step of receiving phenotypic information associated with the subject and/or acquiring from a network phenotypic information associated with the subject.

The present invention also provides in a network, a method for determining whether a subject has breast cancer or a pre-disposition to breast cancer associated with a breast cancer marker, said method comprising the steps of receiving information associated with the breast cancer marker receiving phenotypic information associated with the subject, acquiring information from the network corresponding to the breast cancer marker and/or breast cancer, and based on one or more of the phenotypic information, the breast cancer marker, and the acquired information, determining whether the subject has breast cancer or a pre-disposition to breast cancer. The method may further comprise the step of recommending a particular treatment for the breast cancer or pre-breast cancer condition The present invention also provides a business method for determining whether a subject has breast cancer or a pre-disposition to breast cancer, said method comprising the steps of receiving information associated with the breast cancer marker, receiving phenotypic information associated with the subject, acquiring information from the network corresponding to the breast cancer marker and/or breast cancer, and based on one or more of the phenotypic information, the breast cancer marker, and the acquired information, determining whether the subject has breast cancer or a pre-disposition to breast cancer. The method may further comprise the step of recommending a particular treatment for the breast cancer or pre-breast cancer condition.

The invention also includes an array comprising a breast cancer marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of breast cancer, progression of breast cancer, and processes, such a cellular transformation associated with breast cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

VII. Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of polypeptides or nucleic acids corresponding to one or more markers of the invention, in order to determine whether an individual is at risk of developing breast cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit breast cancer or to treat or prevent any other disorder {i.e. in order to understand any breast carcinogenic effects that such treatment may have}) on the expression or activity of a marker of the invention in clinical trials. These and other agents are described in further detail in the following sections.

A. Diagnostic Assays

An exemplary method for detecting the presence or absence of a polypeptide or nucleic acid corresponding to a marker of the invention in a biological sample involves obtaining a biological sample (e.g. a breast-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general-principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of. the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci*. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit*. Winter 11(1-6):141-8; Hage, D. S., and Tweed, S. A. *J Chromatogr B Biomed Sci Appl* 1997 October. 10;699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from breast cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the breast cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-breast cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from breast cancer or from non-breast cancer cells of breast tissue. The choice of the cell source is dependent on the use of the relative expression level. Using expression found in normal tissues as a mean expression score aids in validating whether the marker assayed is breast specific (versus normal cells). In addition, as more data is accumulated, the mean expression value can be revised, providing improved relative expression values based on accumulated data. Expression data from breast cells provides a means for grading the severity of the breast cancer state.

In another embodiment of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from breast cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether breast cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from breast cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a polypeptide or nucleic acid corresponding to a marker of the invention in a biological sample (e.g. an breast-associated body fluid). Such kits can be used to determine if a subject is suffering from or is at increased risk of developing breast cancer. For example, the kit can comprise a labeled compound or agent capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

B. Pharmacogenomics

Agents or modulators which have a stimulatory or inhibitory effect on expression of a marker of the invention can be administered to individuals to treat (prophylactically or therapeutically) breast cancer in the patient. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the level of expression of a marker of the invention in an individual can be determined to thereby select appropriate agent (s) for therapeutic or prophylactic treatment of the individual.

It has been shown that cancer can be treated by agents, which work by blocking the interaction between estrogen and the estrogen receptor. The blocked interaction is believed to prevent the growth stimulation effects that estrogens would cause, should they bind to the breast cancer cells. The present invention provides a method for detecting the presence, over- and/or under-expression of a marker from Table 2 in a patient sample of estrogen receptor positive breast tumor cells. In one embodiment of the present invention, an agent, e.g., tamoxifen binds to an estrogen receptor of an estrogen receptor positive breast cancer tumor cell, thereby prohibiting binding between estrogen and the estrogen receptor.

Pharmacogenomics deals with clinically significant variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

This invention also provides a process for preparing a database comprising at least one of the markers set forth in Table 1. For example, the polynucleotide sequences are stored in a digital storage medium such that a data processing system for standardized representation of the genes that identify a breast cancer cell is compiled. The data processing system is useful to analyze gene expression between two cells by first selecting a cell suspected of being of a neoplastic phenotype or genotype and then isolating polynucleotides from the cell. The isolated polynucleotides are sequenced. The sequences from the sample are compared with the sequence(s) present in the database using homology search techniques. Greater than 90%, more preferably greater than 95% and more preferably, greater than or equal to 97% sequence identity between the test sequence and the polynucleotides of the present invention is a positive indication that the polynucleotide has been isolated from a breast cancer cell as defined above.

In an alternative embodiment, the polynucleotides of this invention are sequenced and the information regarding sequence and in some embodiments, relative expression, is stored in any functionally relevant program, e.g., in Compare Report using the SAGE software (available though Dr. Ken Kinzler at John Hopkins University). The Compare Report provides a tabulation of the polynucleotide sequences and their abundance for the samples normalized to a defined number of polynucleotides per library (say 25,000). This is then imported into MS-ACCESS either directly or via copying the data into an Excel spreadsheet first and then from there into MS-ACCESS for additional manipulations. Other programs such as SYBASE or Oracle that permit the comparison of polynucleotide numbers could be used as alternatives to MS-ACCESS. Enhancements to the software can be designed to incorporate these additional functions. These functions consist in standard Boolean, algebraic, and text search operations, applied in various combinations to reduce a large input set of polynucleotides to a manageable subset of a polynucleotide of specifically defined interest.

One skilled in the art may create groups containing one or more project(s) by combining the counts of specific polynucleotides within a group (e.g., GroupNormal=Normal1+Normal2, GroupTumor1+TumorCellLine). Additional characteristic values are also calculated for each tag in the group (e.g., average count, minimum count, maximum count). One skilled in the art may calculate individual tag count ratios between groups, for example the ratio of the average GroupNormal count to the average GroupTumor count for each polynucleotide. A statistical measure of the significance of observed differences in tag counts between groups may be calculated.

C. Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for breast cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased administration of the agent can be desirable to increase expression of the marker(s) to higher levels than detected, i.e., to increase the effectiveness of the agent. Alternatively, decreased administration of the agent can be desirable to decrease expression of the marker(s) to lower levels than detected, i.e., to decrease the effectiveness of the agent.

D. Surrogate Markers

The markers of the invention may serve as surrogate markers for one or more disorders or disease states or for conditions leading up to disease states, and in particular, breast cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom*. 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect*. 90: 229-238; Schentag (1999) *Am, J. Health-Syst. Pharm*. 56 Suppl. 3: S21-S24; and Nicolau (1999) *Am, J. Health-Syst. Pharm*. 56 Suppl. 3: S16-S20.

The markers of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA or protein for specific tumor markers in a subject, a drug or course of treatment may be selected that is optimized for the treatment of the specific tumor likely to be present in the subject. Similarly, the presence or absence of a specific sequence mutation in marker DNA may correlate with drug response. The use of pharmacogenomic markers therefore permits the application of the most appropriate treatment for each subject without having to administer the therapy.

EXAMPLE 1

Patients and Methods

Fine needle aspirations (FNA) were collected for transcriptional profiling from 56 patients with breast cancer before undergoing further therapy. All patients were female and had clinically palpable lump in their breast, 3-4 FNA passages were performed using a 25-gauge aspiration needle after numbing the skin with Ethyl Chloride spray. Cells from each pass were collected into separate vials containing either RNAlater (Ambion, Austin Tex.) solution to preserve RNA or were snap frozen and stored at −80° C. Ten to fourteen cytologic smears were also prepared from one passage. The cellularity and cellular composition of each aspirate which was processed for transcriptional profiling was assessed in matching smears by an experienced cytopathologist. Separate tissue samples, usually, a 14-gauge core biopsy, were also obtained for diagnostic purposes. Estrogen, progesterone and HER-2 receptor status were assessed on the diagnostic core biopsies by routine clinical pathology independent of the microarray experiments. ER and PR were assessed by immunohistochemistry using 1D5 and 1A6 antibodies from Zymed (San Francisco, Calif.). Tumors were considered hormone receptor positive if ≧10% of cells showed nuclear staining for ER or PR. HER-2 receptor status was determined by immunohistochemistry using an anti-HER2 monoclonal antibody AB8 (Neomarker, Fremont, Calif.). Patients with unequivocal staining (1+ or 2+) were also tested for gene amplification by fluorescent in situ hybridization (FISH) using the PathVision kit (Vysis, Dovners Grove, Ill.). Tumors with gene copy number >2,0 or IHC staining intensity of 3+ were considered to have HER-2 overexpression.

RNA Isolation and cDNA Microarray Hybridization

RNA was extracted from single pass FNA specimens with RNAeasy Kit (Qiagen, Valencia Calif.). The amount and quality of RNA was assessed with Agilent 2100 Bioanalyzer RNA 6000 LabChip kit (Agilent Technologies, Paolo Alto, Calif.). This system calculates the ratio of ribosomal bands in total RNA samples and shows the percentage of ribosomal impurities as well as provides concentration estimation using as little as 5 ng of total RNA. First strand cDNA synthesis was performed with Superscript II (Invitrogen, Carlsbad, Calif.) in the presence of $^{33}$P-dCTP (100 mCi/ml, Amersham, Little Chalfont, UK) from 1-2 ug total RNA. The generated cDNA probes without further amplification were hybridized to high-density cDNA microarray membranes. The membranes contain 30,000 human sequence clones, including 10,890 expressed sequence tags (EST).

Data Analysis

Expression results were normalized to the median expression value of each membrane and filtered for gene sequences with known Alu-repeats. Alu repeats are transposon-derived short interspersed repetitive sequences that preferentially insert in regions with high GC content. The repeats range from 100 to 400 base pairs and harbor an internal polymerase III promoter but encode no proteins. Genes and ESTs with "Alu" repeats were removed because of the possibility of cross hybridization between various Alu-containing gene sequences. After removal of sequences with known Alu-repeats 27,159 sequences remained for further analysis. In general, genes with low absolute expression values produce less reliable results due to interference from background "noise" of experiments. To screen out genes with unreliable low signal and genes that do not contribute to molecular differences between individual samples, several approaches were used. In one approach genes whose normalized expression value fall within the first decile was removed which left 19,387 genes. To identify genes whose expression was similar across all specimens and therefore provide little value to define differences between tumors, the standard deviation (SD) of normalized expression values was calculated for each gene across all specimens. Genes with a SD<0.17, were removed which left 13,924 genes for further analysis. To restrict analysis to highly expressed genes only, genes with normalized expression value >4,0 in at least 5 of the 18 cases were selected which resulted in 5110 genes. The value of 4.0 was chosen because it is just above the average expression intensity of approximately 3,0 across all membranes. The most stringent analysis combined all filtering criteria including only genes with no Alu-repeats, large expression differences across specimens and normalized expression value of ≧4.0 which resulted in 2695 genes. Multiple analysis was performed with different sets of genes identified with the above screening methods to explore the data set and test for robustness of an observation. Multidimensional scaling of logarithmic data and cluster analysis were used to demonstrate similarities between expression profiles. Supervised and unsupervised single and complete linkage clustering were performed and multidimensional scaling plots were generated by using the rank correlation coefficient subtracted from 1 as the distance metric. Several techniques were used to identify individual genes that contribute to gene expression signatures that define groups of patients with different clinical characteristics. Genes whose expression is associated with ER status were studied by identifying genes whose expression correlated closely with the ER gene itself and also by looking for differentially expressed genes between clinically ER negative versus ER positive tumors and calculating two-sample T-scores for each gene with and without log transformation. Using a hieristical metric derived from 2 methods for distinguishing two populations, we selected genes that had a value ≧0.5 which represented 2.5% of the total genes examined.

RNA Yields from FNA Biopsies

Fifty four of 56 FNAs yielded sufficient cells to attempt RNA extraction. RNA was successfully extracted from 36 (67%) of the 54 FNAs, in 18 cases sufficient quality RNA for further experiments was not obtained. Median total RNA yield of the 36 cases was 2 ug per FNA passage (range from 25 ug to 1 ug).

ER and HER-2 Receptor Status Determined by Routine Clinical Methods Correspond to Receptor Status Assessed by cDNA Mircoarrays The first 18 samples, including 9 ER negative, 9 ER positive cases were used as a training set to assess correspondence between clinical hormone receptor status and receptor status assessed by transcriptional profiling. The next 9 cases were used to assess the validity of findings observed in the first 18. PR was not represented on the array, therefore correlation for this hormone receptor could not be assessed. There was a remarkable correlation between ER status determined by routine immunohistochemistry (IHC) and transcriptional profiling. Transcriptional profiling identified 8 of the 9 ER positive cancers and identified all 9 ER negative cancers correctly when a cut off value of 2,0 for normalized ER gene expression was chosen to divide cancers into ER negative or ER positive groups. This cut off point was determined by inspecting the relationship between clinical ER status and transcription results. The subsequent 9 samples (3 ER positive, 6 ER negative) were used to validate this empirically identified cut off point prospectively. The profiling results using the cut off value of 2 correctly identified all 3 clinically ER positive cases and 5 of the 6 ER negative cases.

Similar analysis was performed to assess correlation between HER-2 expression measured by routine clinical methods (IHC or FISH) and transcriptional profiling. In the training set of the first 18 cases, when a cut off value of 18 for normalized HER-2 gene expression was used profiling identified all 4 patients with 3+ HER-2 overexpression or gene amplification. Cases where IHC indicated 1+ or 2+ staining with or without gene amplification showed significantly lower mRNA expression compared to cases with 3+staining. The retrospectively fitted cut off value 18 was prospectively tested in the next 9 cases.

ER Positive and ER Negative Cancers have Fundamentally Distinct Gene Expression Profiles Unsupervised complete linkage clustering and multidimensional scaling were used to identify gene expression similarities between the first 18 tumors. Multiple analyses were performed using various filtering criteria to remove genes with low signal intensity or uniform expression across specimens. Cluster diagrams generated with 13962 genes, 5110 genes and 2695 genes all revealed some separation of ER negative tumors from ER positive ones indicating large-scale gene expression differences. The best separation between these two types of breast cancer was achieved when 2695 genes were used. The first split of the unsupervised complete linkage clustering separated patients into two groups, one included 7 ER negative and 3 ER positive cases and the second 6 ER positives and 2 ER negatives. Other commonly used clinical parameters such as tumor size, nodal status, HER-2 status or age did not correlate with the two large clusters. However, blacks modified nuclear grade was inversely correlated with ER status. Multidimensional scaling produced similar results, the first principal coordinate of plots generated from the same 2695 genes have also separated patients into 2 groups, one with 7 ER negatives and another with 9 ER positives and 2 ER negatives.

Next, genes that define ER positive versus ER negative tumors were studied based on prior knowledge of clinical ER status. Using the most stringently filtered 2695 genes from the first 18 cases, two-sample t-scores were calculated for each gene where negative scores indicated a higher mean expression in ER negative tumors whereas positive scores indicated higher expression in ER positive tumors. A score of 2.120 was significant at the 5% level, and 2.921 at a 1% level (two-sided testing with 16 degrees of freedom). At the 5% significance level, 108 genes were positively associated and 249 negatively associated with ER status. At the 1% level, 42 genes were positively and 64 negatively associated with ER. If none of the genes were differentially expressed between the two groups, then one would expect to see, by chance alone, 135 genes significant at the 5% level and about 27 at the 1% level. When cluster analysis or MDS were performed using only the 106 genes that had t-scores at the 1% significance level in the first 18 cases, a perfect separation of cases based on clinical ER status were achieved in the entire specimens of 27 cases. Of particular interest were the individual genes associated with ER negative status. Several genes were identified whose expression correlated highly with ER negative status, including the "homolog of mouse quaking QKI", "HSPC182 protein", "interleukin 1 receptor-associated kinase", "interleukin-10 receptor", "platelet phosphofructokinase", "ataxia-telangiectasia group D-associated protein" and "LIM domain only 4." Remarkably, several of the genes that were differentially expressed were also identified by Gruvberger et al. using a different transcriptional profiling technique in surgical tissue. Eleven of the top 50 ER associated genes published by that group were also identified at the 10% significance level. These genes included "trefoil factor 3", "serine/cysteine proteinase inhibitor clad I", "insulin-like growth factor binding protein 2", "cytochrome C oxidase subunit VI c", cysteine-rich protein 1 (up in ER positive cancers), and "serum constituent protein (H74163)", "solute carrier family 7 member 5", "N-myc downstream regulated (AA489266)", platelet phosphofructokinase, ataxia-telangiectasia group D-associated protein", and "LIM domain only 4" (up in ER negative cancers).

Results

Tables 1-3 list the markers identified by the above-referenced protocol. The marker found to be most significantly associated with ER negative status, the "human homolog of mouth quaking gene" is a KH domain RNA binding protein that regulates intracellular RNA trafficking and RNA stability. Nonhistone chromosomal protein high mobility group isoforms I and Y and nuclear autoantigenic sperm protein (NASP) participate in histone remodeling and influence gene transcription. Similarly, spermidine a polyamine product of spermidine synthase, another gene closely associated with ER negativity, has a profound affect on cell proliferation and differentiation. Two nuclear matrix proteins, exportin 1 (CRM1) and Ser/Arg-related nuclear matrix protein that regulate protein transport between the nucleus and cytoplasm were also highly expressed in ER negative tumors. Interleukin -1 receptor-associated kinase 1 (IRAK-1) and Interleukin 10 receptor were also among the genes associated with ER negativity. It appears the metabolic activity of ER negative tumors is also different suggested by high expression of the glycolitic enzyme phosphofructokinase, phosphoglucomutase and NADH-Coenzyme Q reductase.

The contents of all references, patents, published patent applications, and database records cited throughout this application are hereby incorporated by reference.

OTHER EMBODIMENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of assessing whether a patient is afflicted with breast cancer, the method comprising comparing:
   (a) the level of expression of the marker consisting of SEQ ID NO:2 in a patient sample; and
   (b) the level of expression of the marker consisting of SEQ ID NO:2 in a control non-breast cancer sample,
   wherein the patient sample is a breast associated body fluid, a breast tissue or a portion of a breast tissue,
   wherein an increase in the level of expression of the marker consisting of SEQ ID NO:2 in the patient sample as compared to the level of expression of the marker consisting of SEQ ID NO:2 in the control sample is an indication that the patient is afflicted with breast cancer, thereby assessing whether a patient is afflicted with breast cancer.

2. A method of assessing whether a patient is afflicted with estrogen receptor negative breast cancer, the method comprising comparing:
   (a) the level of expression of the marker consisting of SEQ ID NO:2 in a patient sample; and
   (b) the level of expression of the marker consisting of SEQ ID NO:2 in an estrogen receptor (ER) positive breast cancer sample,
   wherein the patient sample is a breast associated body fluid, a breast tissue or a portion of a breast tissue,
   wherein a difference between the level of expression of the marker consisting of SEQ ID NO:2 in the patient sample as compared to the level of expression of the marker consisting of SEQ ID NO:2 in the ER positive breast cancer sample is an indication that the patient is afflicted with estrogen receptor negative breast cancer, thereby assessing whether a patient is afflicted with estrogen receptor negative breast cancer.

3. The method of claim 1, wherein the marker is detected using an antibody or antigen binding fragment thereof which specifically binds the marker.

4. The method of claim 3, wherein the antibody or fragment thereof is a monoclonal antibody or a fragment thereof.

5. The method of claim 3, wherein the antibody or fragment thereof is a polyclonal antibody or a fragment thereof.

6. The method of claim 3, wherein the antibody or a fragment thereof is labeled.

7. The method of claim 6, wherein the antibody or fragment thereof is radio-labeled.

8. The method of claim 6, wherein the antibody or fragment thereof is biotin-labeled.

9. The method of claim 6, wherein the antibody or fragment thereof is labeled with a label selected from the group consisting of a chromophore label, a fluorophore label, and an enzyme label.

10. The method of claim 1, wherein the level of expression of the marker consisting of SEQ ID NO:2 in the patient sample differs from the level of expression of the marker consisting of SEQ ID NO:2 in the control sample by a factor of at least about 2.

11. The method of claim 1, wherein the level of expression of the marker consisting of SEQ ID NO:2 in the patient sample differs from the level of expression of the marker consisting of SEQ ID NO:2 the control sample by a factor of at least about 5.

12. The method of claim 1, wherein the patient sample is a breast-associated body fluid.

13. The method of claim 12, wherein the breast-associated body fluid is selected from the group consisting of blood, breast fluid, lymph fluid, cystic fluid, nipple aspirates, and fluid collected from a lump biopsy.

14. The method of claim 1, wherein the patient sample comprises cells obtained from a breast tissue sample.

15. A method of assessing whether a patient is afflicted with estrogen receptor negative breast cancer, the method comprising comparing:
   (a) the level of expression of the marker of SEQ ID NO:2 in a patient sample; and
   (b) the level of expression of the marker of SEQ ID NO:2 in an estrogen receptor (ER) positive breast cancer sample,
   wherein the patient sample is a breast associated body fluid, a breast tissue or a portion of a breast tissue,
   wherein an increase in the level of expression of the marker of SEQ ID NO:2 in the patient sample as compared to the level of expression of the marker of SEQ ID NO:2 in the ER positive breast cancer sample is an indication that the patient is afflicted with estrogen receptor negative breast cancer, thereby assessing whether a patient is afflicted with estrogen receptor negative breast cancer.

\* \* \* \* \*

UNITED STATES PATENT AND TRADEMARK OFFICE
CERTIFICATE OF CORRECTION

PATENT NO.         : 7,504,222 B2                                    Page 1 of 1
APPLICATION NO.    : 10/285393
DATED              : March 17, 2009
INVENTOR(S)        : Mark D. Ayers et al.

It is certified that error appears in the above-identified patent and that said Letters Patent is hereby corrected as shown below:

In claim 1, at column 151, line 16, replace "non-breast cancer" with --non-cancerous patient--.

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,504,222 B2
APPLICATION NO. : 10/285393
DATED : May 17, 2010
INVENTOR(S) : Ayers et al.

Page 1 of 1

It is certified that error appears in the above-identified patent and that said Letters Patent is hereby corrected as shown below:

Title Page, Should read (*) Notice: Subject to any disclaimers, the term of this patent is extended or adjusted under 35 U.S.C. 154(b) by 1515 days.

Signed and Sealed this

Seventeenth Day of August, 2010

David J. Kappos
*Director of the United States Patent and Trademark Office*